(12) United States Patent
Xia et al.

(10) Patent No.: US 12,191,911 B2
(45) Date of Patent: Jan. 7, 2025

(54) APPARATUS AND METHOD FOR SPATIAL LIGHT MODULATION

(71) Applicant: KING'S COLLEGE LONDON, London (GB)

(72) Inventors: Wenfeng Xia, London (GB); Tianrui Zhao, London (GB); Tom Vercauteren, London (GB); Sebastien Ourselin, London (GB)

(73) Assignee: KING'S COLLEGE LONDON (GB)

( * ) Notice: Subject to any disclaimer, the term of this patent is extended or adjusted under 35 U.S.C. 154(b) by 112 days.

(21) Appl. No.: 17/792,914

(22) PCT Filed: Jan. 15, 2021

(86) PCT No.: PCT/GB2021/050099
§ 371 (c)(1),
(2) Date: Jul. 14, 2022

(87) PCT Pub. No.: WO2021/144588
PCT Pub. Date: Jul. 22, 2021

(65) Prior Publication Data
US 2023/0239053 A1    Jul. 27, 2023

(30) Foreign Application Priority Data

Jan. 17, 2020    (GB) .................................. 2000752

(51) Int. Cl.
*H04B 10/50*    (2013.01)
*A61F 9/008*    (2006.01)
*H04B 10/61*    (2013.01)

(52) U.S. Cl.
CPC ........... *H04B 10/504* (2013.01); *A61F 9/008* (2013.01); *H04B 10/61* (2013.01)

(58) Field of Classification Search
CPC .... H04B 10/504; H04B 10/54; H04B 10/541; H04B 10/508
See application file for complete search history.

(56) References Cited

U.S. PATENT DOCUMENTS

2015/0015879 A1* 1/2015 Papadopoulos ......... G02F 1/011
356/301
2018/0034556 A1* 2/2018 Willner ................ H04B 7/0413
(Continued)

FOREIGN PATENT DOCUMENTS

CN    201811589195 A    3/2019

OTHER PUBLICATIONS

Sharma et al.; Inverse Scattering via Transmission Matrices: Broadband Illumination and Fast Phase Retrieval Algorithms, IEEE Transactions on Computational Imaging, IEEE, vol. 6, May 27, 2019, pp. 95-108, XP011769659, ISSN: 2573-0436, DOI: 10.1109/TCI.2019.2919257. (Year: 2019).*
(Continued)

*Primary Examiner* — Nathan M Cors
(74) *Attorney, Agent, or Firm* — Parsons Behle & Latimer

(57) ABSTRACT

A computer-implemented method of transmitting through a disordered medium from a transmitter to a receiver an image represented as input coherent electromagnetic radiation, the disordered medium having a transmission matrix comprising a plurality of complex-valued transmission constants that relate said input coherent electromagnetic radiation to output electromagnetic radiation at said receiver, which method comprises the steps of:
performing a characterising process on said disordered medium to determine said transmission matrix;
using said transmitter to transmit said image through said disordered medium;
(Continued)

performing a reconstruction process using said transmission matrix to generate a reconstructed image from the output electromagnetic radiation at said receiver;
wherein in said characterisation process the step of determining said transmission matrix comprises:
  determining said complex-valued transmission constants as real-valued transmission constants by using an approximately linear relationship between said input electromagnetic radiation and said output electromagnetic radiation; and
  using said real-valued transmission constants to generate and store a version of the transmission matrix;
and said reconstruction process comprises the steps of:
  generating an output signal comprising intensity or amplitude values of said output electromagnetic radiation;
  generating said reconstructed image by combining said output signal and said version of the transmission matrix in a way that effects a matrix multiplication of an inverse of said transmission matrix and said output signal; and
  outputting said reconstructed image from said receiver.

16 Claims, 35 Drawing Sheets

(56) References Cited

U.S. PATENT DOCUMENTS

2018/0107157 A1    4/2018  Park et al.
2018/0266917 A1*   9/2018  Chen ................. G01M 11/3118
2020/0407082 A1*  12/2020  Ashrafi ............... H04B 10/508

OTHER PUBLICATIONS

Popoff et al., "Controlling Light Through Optical Disordered Media : Transmission Matrix Approach"; Nov. 15, 2011; arXiv: 1107.5285; https://doi.org/10.48550/arXiv.1107.5285 (Year: 2011).*

Jian Wei Tay, Jinyang Liang and Lihong V. Wang; Amplitude-masked photoacoustic wavefront shaping and application in flowmetry; Optical Imaging Laboratory, Department of Biomedical Engineering, Washington University in St Louis; Oct. 1, 2014; 39(19): 5499-5502.

Sharma Manoj Kumar et al, "Inverse Scattering via Transmission Matrices: Broadband Illumination and Fast Phase Retrieval Algorithms", May 27, 2019 (May 27, 2019), vol. 6, p. 95-108.

European Patent Office, "International Search Report and Written Opinion"; PCT/GB2021/050099; May 6, 2021 (May 6, 2021).

* cited by examiner

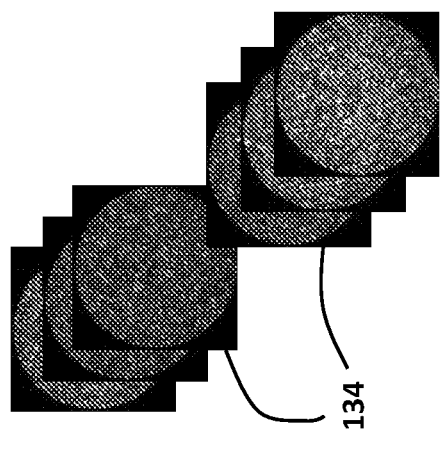
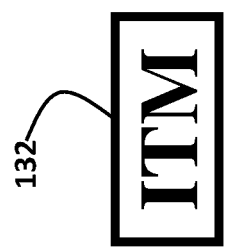
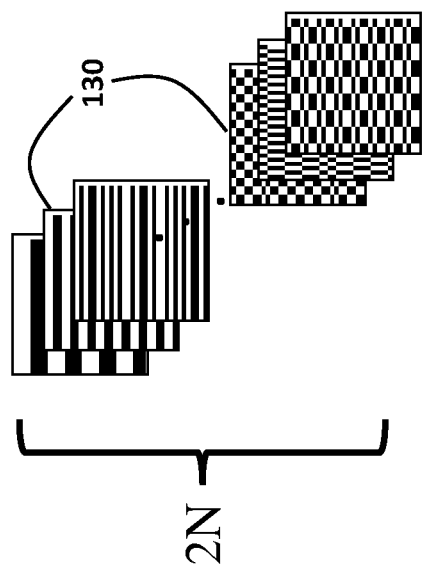
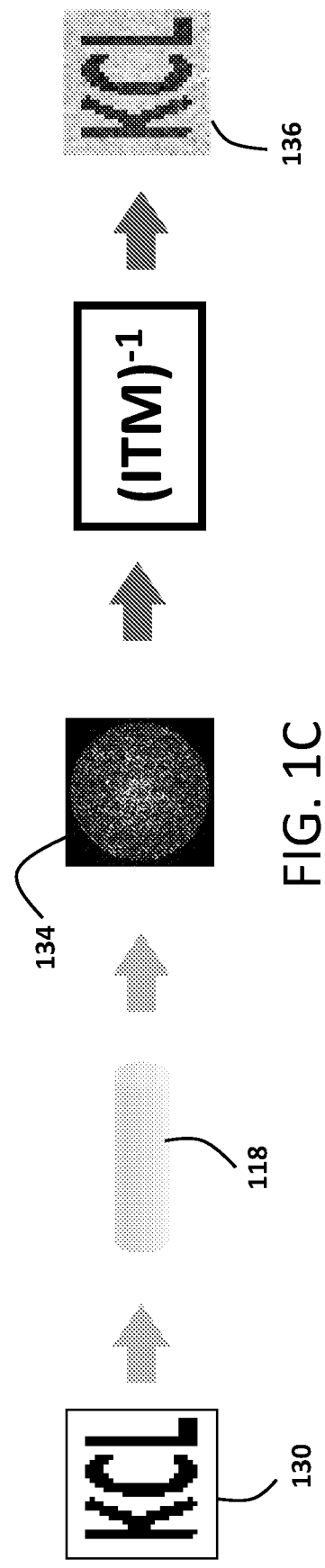
FIG. 1B
FIG. 1C

| Fiber | Diameter (μm) | Numerical aperture | Mode count | Output pixels count |
|---|---|---|---|---|
| Fiber-105-0.22 | 105 | 0.22 | 9304 | 200×200 |
| Fiber-200-0.22 | 200 | 0.22 | 33756 | 360×360 |
| Fiber-200-0.50 | 200 | 0.50 | 174360 | 500×500 |

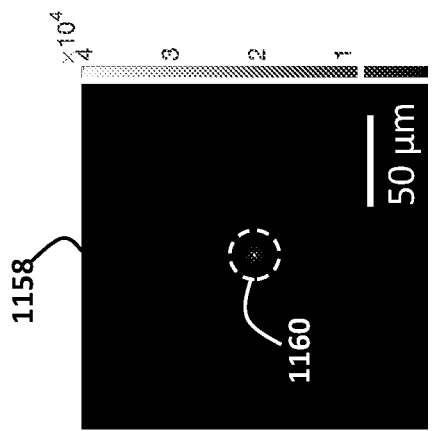
FIG. 16A
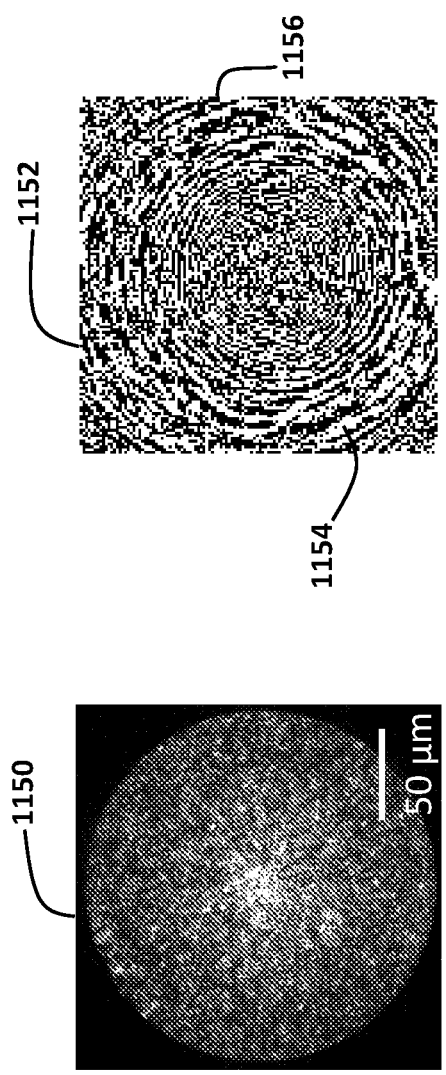
FIG. 16B
FIG. 16C
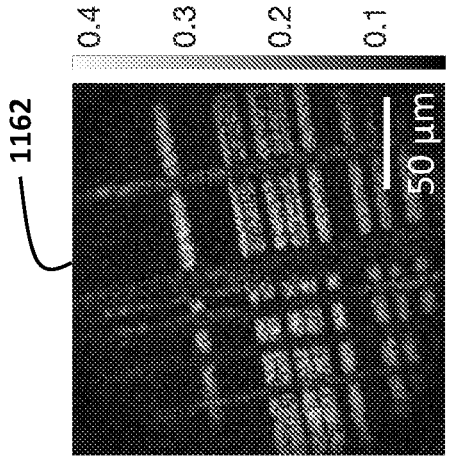
FIG. 16F
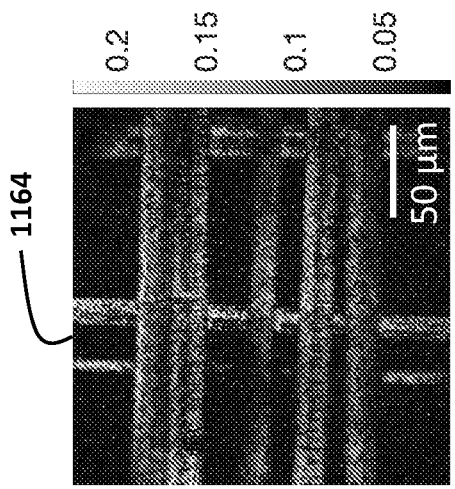
FIG. 16G
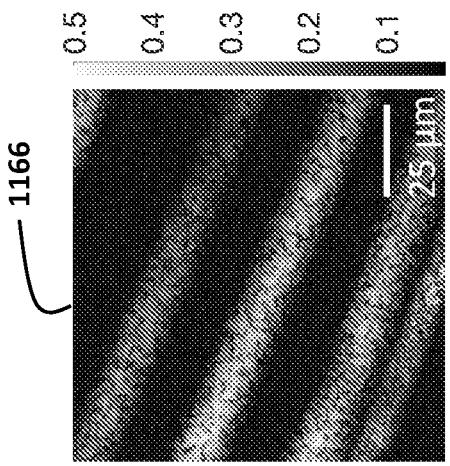
FIG. 16H

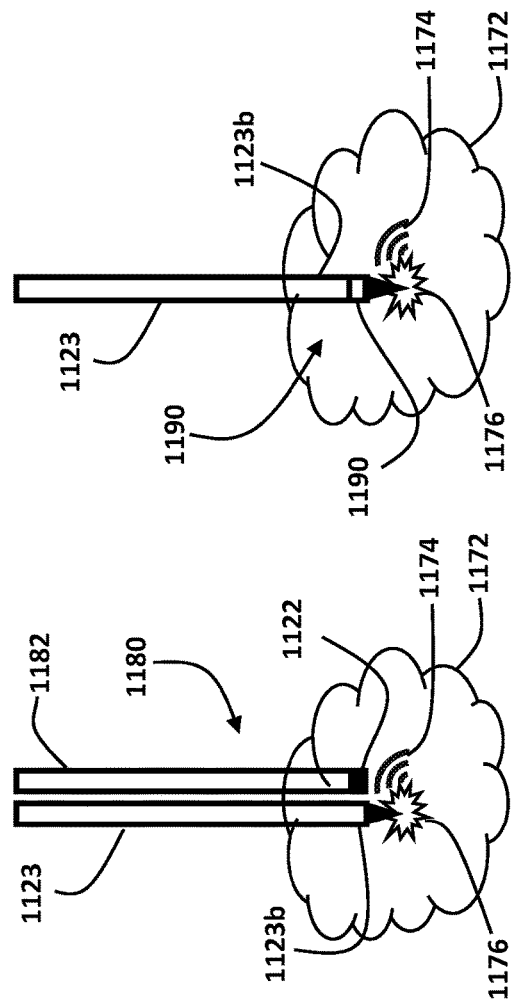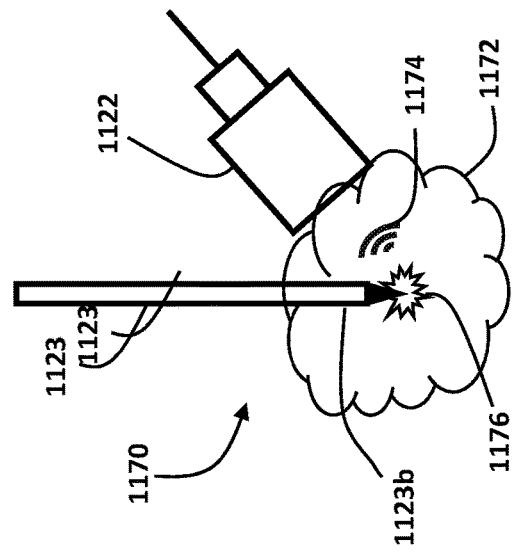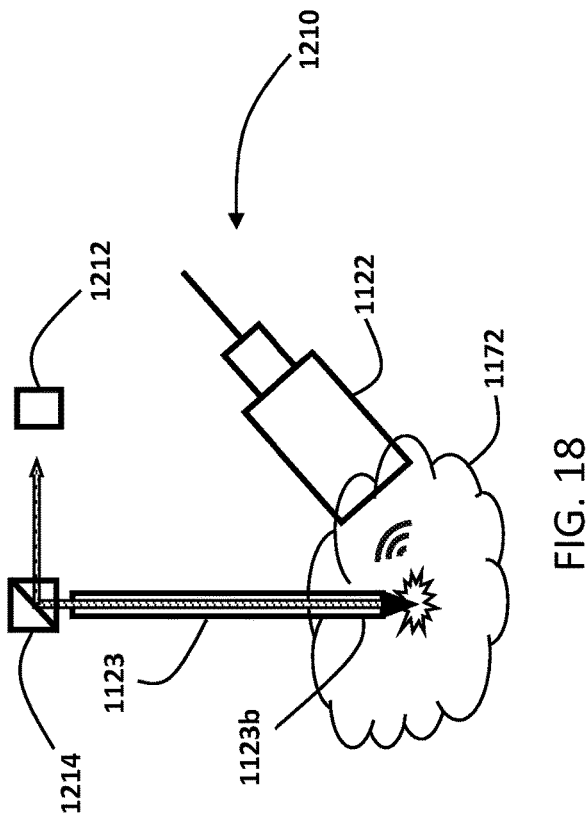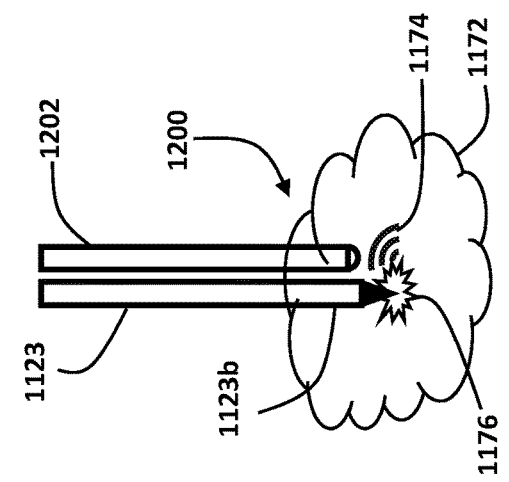

| Algorithm | PBR (S) | Time (S) | PBR (E) | Time (E)[d] | No. of input modes |
|---|---|---|---|---|---|
| Reference TM[a] | 183.0 | - | - | - | 1024 |
| | 208.4 | | | | |
| Estimated TM[b] | 170.4 | 15 s | 58.5 | 46 s | 1024 |
| | 190.3 | | 64.2 | | |
| RVITM[c] | 183.0 | 0.00075 s | 79.9 | 10.3 s | 1024 |
| | 228.2 | | 89.4 | | |
| GA | 239.7 | 400 s | 91 | 7920 s | 1024 |
| CPA | 156.7 | 4 s | 36 | 36 s | 1024 |

FIG. 22

APPARATUS AND METHOD FOR SPATIAL LIGHT MODULATION

FIELD OF THE INVENTION

The present invention relates to a computer-implemented method of focusing electromagnetic radiation at a target, the electromagnetic radiation travelling to the target by reflection from a disordered medium. The present invention also relates to a method of optical wireless communication using the focusing method, and to a method of seeing or detecting an object behind an obstruction.

The present invention also relates to computer-implemented method of focusing electromagnetic radiation at a target with an improved peak-to-background ratio (or equivalent), the electromagnetic radiation travelling to the target via a disordered medium. The present invention also relates to a method of using the method in deep tissue optical microscopy, optogenetics, micro-manipulation, laser microsurgery, laser-induced thermal therapy and photoacoustic imaging. The present invention also relates to a method of non-line-of sight optical wireless communication in free space. The present invention also relates to a transmitter and a receiver for use in the computer-implemented method, to a network interface module comprising the transmitter or the receiver, to an optical communication system comprising the transmitter or the receiver, and to an optical communication system comprising the transmitter and the receiver.

The present invention relates to a computer-implemented method for transmitting and receiving an image through a disordered medium. The present invention also relates to a transmitter and a receiver for use in the computer-implemented method, to a network interface module comprising the transmitter or the receiver, to an optical communication system comprising the transmitter or the receiver, and to an optical communication system comprising the transmitter and the receiver.

BACKGROUND OF THE INVENTION

Multimode optical fibers (MMFs) have been increasingly attractive for applications in biomedical endoscopy and telecommunications, owing to their capability to transport light via a large number of transverse optical modes. For biomedical endoscopy, the number of transverse modes in a MMF can be considered equivalent to the number of informative pixels or voxels in the images. Compared to multicore coherent fibre bundles that are commonly used in biomedical endoscopy. MMFs are significantly more cost-effective, and the effective pixel density in an MMF can be 1-2 orders of magnitudes greater. For telecommunications, MMFs are attractive as they have the potential to multiplex data signals within the large number of modes. However, since the light-propagation material of MMFs suffers from modal dispersion and mode coupling. For example when projecting an input image pattern onto the proximal end of a MMF, the light field inside the MMF couples into different modes with different propagation constants and causes a seemingly random output speckle pattern at the distal end. Therefore, the propagation characteristics of a MMF are required for reconstructing input image patterns from measured output speckle patterns.

In the last decade, wavefront shaping has been an emerging method for controlling light transport through a disordered medium. Recently, a number of research groups have studied the transmission matrix (TM) theory and validated it for image transmission through disordered medium such as MMFs. In TM theory, the optical system of a disordered medium is characterized by a complex-valued transmission matrix, which connects the input and output light fields with transmission constants that have amplitude and phase information. Based on this TM, both the input and output light fields are divided into orthogonal or spatial frequency modes, whilst a transmission constant linking an input mode to an output mode represents the change of light field during the transport between these two modes. Therefore, the input light field and hence the input intensity pattern can be calculated when both the TM and the phase and amplitude of output light field are known. However, conventional cameras are only able to capture light intensity (square of amplitude), and as such the phase information is usually obtained with holographical methods, which requires the use of a complicated optical reference arm that can degrade the system stability.

Recently, reconstruction of input images transmitted through a disordered medium using only the intensity information of the output light field was achieved with deep learning and model-based methods, allowing a simpler optical system for image retrieval compared to TM methods. With deep learning, a set of images were projected onto the proximal end of an MMF as inputs, whilst the intensity-only speckles were captured by a camera from the distal fibre tip. The large set of input-output pairs were then used to train a multi-layer neural network for predicting the input images from the output speckles. After training, the multi-layer neural network was able to predict input images such as handwritten digits and letters, and Quickdraw objects from the intensity-only speckles. However, the training of multi-layer neural network requires large datasets and iterative optimisation processes, leading to prolonged time for data acquisition and training. Further, the performance of the trained neural network is likely to depend on the similarities between the testing and training datasets.

Most recently, a model-based method was used to characterise a MMF. With this method, a set of input images were projected onto one end of a MMF whilst the intensity-only outputs at the other end were captured by a camera and converted into amplitude (square root of the intensity) information with zero phase. With these amplitude-only input-output pairs, an iterative optimisation algorithm was used to calculate a complex-valued matrix as the inverse TM of the fibre. In contrast to the deep learning methods, this algorithm explicitly linked the input images with the output speckles with a physically informed model and hence allowed the retrieval of images of complex natural scenes. However, this method requires large datasets and a time-consuming iterative optimisation progress, which limit its applicability.

Other aspects of the invention relate to focusing light at a target via a disordered medium, the focusing having an improved peak-to-background ratio (PBR). Focusing light through biological tissue (one example of a disordered medium) is of great significance for applications in a broad spectrum of life sciences including deep tissue optical microscopy, optogenetics, micro-manipulation, and laser microsurgery. Over the last decade, wavefront shaping (WS) emerged as an effective approach for focusing light at a target inside or through a disordered medium. The basic principle of WS is to modulate the incident light field to match the microscopic scattering properties of the medium so that the scattering-induced phase distortion is corrected. In this way the scattered waves interfere constructively at the target position behind a scattering layer to form a sharp focus. Conventional methods for optical WS usually require a detector to be placed behind the scattering medium to measure the light intensity at the target position, which restricts their practical uses in biological tissues. Various non-invasive methods have been proposed that provide feedback with internal "guide-stars" so that the light intensity at the target location can be maximised. These guide-stars include exogenous fluorescence particles, ultrasound-tagged light based on acousto-optics and light-generated ultrasound waves based on the photoacoustic effect.

Photoacoustic-guided WS has attracted significant research interest in recent years since it avoids the use of a complex optical reference arm as used for example in phase conjugation based WS and with the use of exogenous particles as guide-stars. With photoacoustic-guided WS, a focused ultrasound transducer measures the light-generated ultrasound/photoacoustic waves at the acoustic focus. By iteratively optimising the wavefront of the incident light with a liquid-crystal spatial light modulator (LC-SLM) or a digital micromirror device (DMD), the intensity of the acoustic pressure is maximised, leading to an intense optical focus with its size defined by the focus size of the ultrasound transducer. Several methods have been proposed to reduce the size of the optical focal spot. However, although these methods have proven effective for light focusing through a diffuser with non-invasive guidance, it usually took between approximately 15 minutes and several hours to form a light focus due to the use of time-consuming iterative algorithms such as a genetic algorithm. A problem with focusing light through biological tissue is the rapid speckle decorrelation caused by the dynamic nature of the tissue (e.g. blood flow). It was be useful to reduce the time taken to form a light focus with photoacoustic guidance, especially for in vivo applications, and to improve the PBR of light at the focus.

More recently, WS has been proposed for beam-steering in optical wireless communications (see Cao Z, Zhang X, Osnabrugge G, Li J, Vellekoop I M, Koonen A M. Reconfigurable beam system for non-line-of-sight free-space optical communication. Light: Science & Applications, 2019 Jul. 24:8(1):1-9). Light is transmitted via a phase only spatial light modulator ('PO-SLM') toward a receiver by reflection from a diffuse reflecting surface. By spatially modulating the phases of the incident light field using the PO-SLM it is possible to compensate for the diffuse reflection and improve the focus of light at the receiver. However, it is acknowledged in the Cao paper that light intensity at the receiver decreases as the distance of the receiver from the reflecting surface increases. It is suggested that this decrease can be compensated by increasing the number of segments of the PO-SLM, but this is not always practical. Furthermore, owing to the low frame rate of the PO-SLM (60 Hz) the focusing process is time consuming, limiting its practical application.

SUMMARY

Some embodiments are based on our discovery that the real number transmission constants (as determined by the at least some of the methods described herein) of a real-valued transmission matrix encode (or represent or approximate) both phase and amplitude information of the corresponding complex-valued transmission matrix. The complex-valued transmission matrix provides a relationship between the amplitude and phase of coherent electromagnetic radiation at the input and the amplitude and phase of electromagnetic radiation at an output (or target) travelling via a disordered medium. We have discovered that, in some embodiments, it is not necessary to measure both the amplitude and phase of electromagnetic radiation at the input and output electromagnetic radiation (which tends to be difficult and slow), but that the relationship between intensities at the input and the output them can be approximated by determination of the real-valued transmission constants. Furthermore, we have discovered that in some embodiments by switching on a group of electromagnetic radiation sources (e.g. DMD micromirrors) for which the real-valued transmission constants have the highest real number values in the real-valued transmission matrix, and switching off electromagnetic sources having lower valued real number transmission constants, it is possible to increase the ratio of peak light intensity at the target to the intensity of background light at the target (as distinct from simply increasing both the peak light intensity at the target and the background light intensity). By using the size of the real number of the real-valued transmission constants to select electromagnetic radiation sources to switch on or off, account is taken of both the amplitude and phase contributed to the output by that source. In some embodiments this may result in a different selection of on/off electromagnetic radiation sources than selection according to phase of each source only.

According to some embodiments there is provided a computer-implemented method of focusing electromagnetic radiation at a target, the electromagnetic radiation travelling to the target by reflection from a disordered medium, which method comprises a characterising process and a focusing process:

the characterising process comprising the steps of:
(a) controlling a transmitter to:
generate first input coherent electromagnetic radiation using a plurality of electromagnetic radiation sources;
apply a sequence of spatial modulation patterns to said first input coherent electromagnetic radiation, each spatial modulation pattern setting each one of plurality of electromagnetic radiation sources to an on state or an off state; and
direct the first input coherent electromagnetic radiation toward the target by reflection from the disordered medium;
(b) controlling a receiver to:
receive a signal representing an intensity of output electromagnetic radiation at the target, and generate a corresponding output signal;
store output data representing each output signal whereby, once the sequence of spatial modulation patterns has concluded, said output data comprises a plurality of output signals, each output signal corresponding to one of the spatial modulation patterns;
wherein a complex-valued transmission matrix comprising a plurality of complex-valued transmission constants approximates a relationship between the first input coherent electromagnetic radiation and the output electromagnetic radiation, the characterising process determining a real-valued transmission matrix comprising a plurality of real-valued transmission constants which approximate a relationship between the intensities of the first input coherent electromagnetic radiation and the output electromagnetic radiation, each real-valued transmission constant associated with one of said plurality of electromagnetic radiation sources, the method further comprising the step of:
(c) for each electromagnetic radiation source of the plurality of electromagnetic radiation sources determining the associated real-valued transmission constant as a function of said output data and the on and off states of that electromagnetic radiation source over the sequence of spatial modulation patterns;
(d) storing said plurality of real-valued transmissions constants;
(e) determining a focusing spatial modulation pattern of said plurality of electromagnetic radiation sources by:
determining if each real-valued transmission constant represents a positive value and thereby an increase in output intensity of the electromagnetic radiation at the target when that electromagnetic radiation source is on; and
setting a state indicator for electromagnetic radiation source for causing the electromagnetic radiation source to be in said on state if the associated real-valued transmission constant represents a positive value and in said off state if not, the state indicators for said plurality of electromagnetic sources forming said focusing spatial modulation pattern;
the focusing process comprising the steps of:
(f) generating second input coherent electromagnetic radiation and applying a spatial modulation to said second input coherent electromagnetic radiation using said focusing spatial modulation pattern; and
(g) directing said second input coherent electromagnetic radiation toward the target by reflection from the disordered medium.

In an embodiment said disordered medium may cause a diffuse reflection and/or scattering of said electromagnetic radiation.

In an embodiment said step of directing the first input coherent electromagnetic radiation toward the target via the disordered medium may comprise transmitting said first input coherent electromagnetic radiation for reflection from an external surface of said disordered medium before being received by said receiver.

In an embodiment said external surface may comprise a surface of a building.

In an embodiment said surface of a building may comprise an optical reflecting surface such as an external or internal wall, floor or ceiling.

In an embodiment said transmitter and receiver may be arranged in a non-line of sight configuration.

In an embodiment said receiver comprises said target.

In an embodiment each real-valued transmission constant may comprise a real number, and wherein in step (e):
the determining step may comprise:
determining a group of real-valued transmission constants from the plurality of real-valued transmission constants by examining the real number of each real-valued transmission constant and including the real-valued transmission constant in the group so that the group comprises real-valued transmission constants which have real numbers greater than the real numbers of real-valued transmission constants not in said group
the setting step may comprise:
setting said state indicator for electromagnetic radiation source for causing the electromagnetic radiation source to be in said on state if the associated real-valued transmission constant is in said group and in said off state if not.

In an embodiment there is provided a computer-implemented method of focusing electromagnetic radiation at a target, the electromagnetic radiation travelling to the target via a disordered medium, which method comprises a characterising process and a focusing process:
the characterising process comprising the steps of:
(a) controlling a transmitter to:
generate first input coherent electromagnetic radiation using a plurality of electromagnetic radiation sources;
apply a sequence of spatial modulation patterns to said first input coherent electromagnetic radiation, each spatial modulation pattern setting each one of plurality of electromagnetic radiation sources to an on state or to an off state; and
direct the first input coherent electromagnetic radiation toward the target via the disordered medium;
(b) controlling a receiver to:
receive a signal representing an intensity of output electromagnetic radiation at the target, and generate a corresponding output signal;
store output data representing each output signal whereby, once the sequence of spatial modulation patterns has concluded, said output data comprises a plurality of output signals, each output signal corresponding to one of the spatial modulation patterns;
wherein a complex-valued transmission matrix comprising a plurality of complex-valued transmission constants approximates a relationship between the first input coherent electromagnetic radiation and the output electromagnetic radiation, the characterising process determining a real-valued transmission matrix comprising a plurality of real-valued transmission constants which approximate a relationship between the intensities of the first input coherent electromagnetic radiation and the output electromagnetic radiation, each real-valued transmission constant associated with one of said plurality of electromagnetic radiation sources, the method further comprising the steps of:
(c) for each electromagnetic radiation source of the plurality of electromagnetic radiation sources determining the associated real-valued transmission constant as a function of said output data and the on and off states of that electromagnetic radiation source over the sequence of spatial modulation patterns;
(d) storing said plurality of real-valued transmissions constants, each real-valued transmission constant comprising a real number.
(e) determining a focusing spatial modulation pattern of said plurality of electromagnetic radiation sources by:
determining a group of real-valued transmission constants from the plurality of real-valued transmission constants by examining the real number of each real-valued transmission constant and including the real-valued transmission constant in the group so that the group comprises real-valued transmission constants which have real numbers greater than the real numbers of real-valued transmission constants not in said group;
and
setting a state indicator for each electromagnetic radiation source for causing the electromagnetic radiation source to be in said on state if the associated real-valued transmission constant is in said group and in said off state if not, the state indicators for said plurality of electromagnetic sources forming said focusing spatial modulation pattern;
the focusing process comprising the steps of:
(f) generating second input coherent electromagnetic radiation and applying a spatial modulation to said second input coherent electromagnetic radiation using said focusing spatial modulation pattern; and
(g) directing said second input coherent electromagnetic radiation toward the target via the disordered medium.

In an embodiment said group may comprise real-valued transmission constants which cause a peak-to-background ratio of said second electromagnetic radiation at said target to be greater than one.

In an embodiment said group may comprise a predetermined percentage of the real-valued transmission constants when ranked by the real numbers.

In an embodiment said predetermined percentage may comprise the top n % of the real-valued transmission constants.

In an embodiment n is within one of the following ranges: $15\% \leq n \leq 50\%$, $20\% \leq n \leq 45\%$, $22\% \leq n \leq 40\%$, $25\% \leq n \leq 35\%$, $25\% \leq n \leq 33\%$, and $29\% \leq n \leq 31\%$.

In an embodiment n may be within one of the following ranges: $30\% \leq n \leq 50\%$, $30\% \leq n \leq 45\%$, $30\% \leq n \leq 40\%$, $30\% \leq n \leq 35\%$, $30\% \leq n \leq 33\%$, $30\% \leq n \leq 31\%$.

In an embodiment n may be approximately 30%.

In an embodiment in step (c) said determining of the associated real-valued transmission constant may comprise performing a computer-implemented operation that represents a product of the output data of each output signal and the corresponding on or off state of the electromagnetic radiation source of the spatial modulation associated with that output signal respectively.

In an embodiment said computer-implemented operation may further comprise a summation of said products to for each associated real-valued transmission constant.

In an embodiment said on state and said off state may be represented in said computer-implemented operation as positive and negative values respectively or vice-versa.

In an embodiment step (e) may further comprise the step storing said focusing spatial modulation pattern as a plurality of binary values, a first binary value type indicating that electromagnetic radiation sources should be on and a second binary value type indicating that the electromagnetic radiation sources should be off.

In an embodiment said plurality of binary values may be stored as an array whereby a position of each binary value in the array indicates the associated electromagnetic radiation source.

In an embodiment, step (e) may be performed by said receiver, the method further comprising the step of the receiver sending said focusing spatial modulation pattern to said transmitter using a data communication system.

In an embodiment steps (a) to (c) may be completed in less than 500 ms, and preferably less than 300 ms.

In an embodiment steps (a) to (e) may be non-iterative.

In an embodiment steps (a) to (g) may effect a wavefront shaping of said first and second input coherent electromagnetic radiation by said sequence of spatial modulation patterns and said focusing spatial modulation pattern respectively.

In an embodiment said receiver may have a receiver focus and said wherein wavefront shaping is guided by said receiver focus.

In an embodiment in step (b) said receiving the signal representing an intensity of output electromagnetic radiation at the receiver may comprise a direct detection of the electromagnetic radiation intensity at the receiver.

In an embodiment said direct detection may comprise the steps of:
providing a plurality of electromagnetic radiation detectors at said receiver;
performing steps (a) to (e) for different electromagnetic radiation detectors, whereby a respective focusing spatial modulation pattern is generated for each different electromagnetic radiation detector;
combining said respective focusing spatial modulation patterns into a single multi-focusing spatial modulation pattern; and
performing steps (f) and (g) using the multi-focusing spatial modulation pattern whereby electromagnetic radiation is focused simultaneously onto said different electromagnetic radiation detectors.

In an embodiment, each different electromagnetic detector may comprise a single electromagnetic radiation detector or a group of electromagnetic radiation detectors selected from the plurality of electromagnetic radiation detectors.

In an embodiment, the step of combining may comprise averaging corresponding state indicators in each respective spatial modulation pattern to produce an average state indicator, and subjecting said average state indicator to a state threshold, the outcome determining whether the corresponding state indicator of said multi-focusing spatial modulation pattern is set to said on state or said off state.

In an embodiment said direct detection may comprise the steps of:
providing a plurality of electromagnetic radiation detectors at said receiver;
performing steps (a) to (e) for each electromagnetic radiation detector, whereby a respective focusing spatial modulation pattern is generated for each electromagnetic radiation detector;
performing steps (f) and (g) for each electromagnetic radiation detector using the respective focusing spatial modulation pattern and recording an output intensity signal for each electromagnetic radiation detector.

In an embodiment said plurality of electromagnetic detectors may be arranged in a 2D array.

In an embodiment said plurality of electromagnetic radiation detectors may comprise a plurality of digital image sensors.

In an embodiment said step of recording said output intensity signals may comprise recording with a single receiver.

In an embodiment said single receiver may indirectly detect said electromagnetic radiation at said target, said receiver generating said output intensity signals for each respective focusing spatial modulation pattern.

In an embodiment said indirect detection may comprise detection of ultrasound waves generated by the photoacoustic effect when said output electromagnetic radiation reaches said target.

In an embodiment said single receiver may comprise an ultrasonic detector.

In an embodiment, the method may further comprise the step of generating a digital image from said output intensity signals.

In an embodiment in step (b) said receiving the signal representing an intensity of output electromagnetic radiation at the receiver comprises an indirect detection of the electromagnetic radiation intensity.

In an embodiment said indirect detection may comprise detection of ultrasound waves generated by the photoacoustic effect when said output electromagnetic radiation reaches said target.

In an embodiment said indirect detection may comprise detection of fluorescence generated by said output electromagnetic radiation when it reaches said target.

In an embodiment said single receiver may comprise an electromagnetic radiation detector adapted to detect said fluorescence.

In an embodiment in step (a) each electromagnetic radiation source may be on within said sequence of spatial modulations the same number of times that it is off.

In an embodiment in step (a) the number of electromagnetic radiation sources that are on within each spatial modulation of said sequence of spatial modulation patterns may be the same as the number of electromagnetic radiation sources that are off.

In an embodiment each spatial modulation of said sequence of spatial modulations may be generated from a generating matrix that ensures that each spatial modulation is orthogonal to each other spatial modulation.

In an embodiment the generating matrix may comprise a Hadamard matrix.

In an embodiment the method may further comprise the step of repeating steps (a) to (e) to generate a new focusing spatial modulation pattern.

In an embodiment said repeating may be performed periodically, non-periodically or in response to an instruction received from a user.

In an embodiment said plurality of electromagnetic sources may be arranged in a 2D array.

In an embodiment said plurality of electromagnetic radiation sources may comprise a plurality of individually controllable electromagnetic radiation sources.

In an embodiment said plurality of electromagnetic radiation sources may comprise a plurality of individually controllable mirrors, for example in the form of a digital micromirror device.

In an embodiment said step of directing the first input coherent electromagnetic radiation toward the target via the disordered medium may comprise transmitting said first input coherent electromagnetic radiation through said disordered medium before being received by said receiver.

In an embodiment in step (a) said first coherent electromagnetic radiation may have a first wavelength and in said step (f) said second coherent electromagnetic radiation may have a second wavelength, and wherein:

(i) said first wavelength may be the same as said second wavelength; or (ii) said first wavelength may be different, but close to, to said second wavelength.

In an embodiment the method may further comprise the step of repeating steps (a) to (c) for a plurality of different wavelengths or small range of wavelengths, and storing one or more focusing spatial modulation pattern for each wavelength or each small range of wavelengths.

In an embodiment said first input coherent electromagnetic radiation may have a wavelength between about 100 nm and about 10,000 nm.

In an embodiment said second input coherent electromagnetic radiation may have a wavelength between about 100 nm and about 10,000 nm.

In an embodiment in step (a) said first input coherent electromagnetic radiation may have one of pulsed and intensity-modulated continuous wave to cause the photoacoustic effect at said target.

In an embodiment said second input coherent electromagnetic radiation may be one of continuous wave, pulsed and intensity-modulated.

In an embodiment, said first input coherent electromagnetic radiation may have a high degree of temporal and spatial coherence.

In an embodiment said disordered medium may comprise one of a biological tissue and an optical waveguide.

In an embodiment the real-valued transmission matrix may comprise:

(i) the real-valued transmission constants stored as a matrix processable by a computer;

(ii) any computer-processable equivalent representation of (i); or (iii) any computer-processable representation the inverse of (i).

According to some embodiments there is provided a method of non-line-of sight optical wireless communication in free space, which method comprises performing a computer-implemented method of focusing electromagnetic radiation at a target as set out herein, the disordered medium being a surface of a building from which the electromagnetic radiation is scattered and reflected toward the receiver, whereby using the focusing spatial modulation pattern to transmit data to the receiver increases a signal to noise ratio of electromagnetic radiation at the receiver.

According to some embodiments there is provided a method of detecting an object behind an obstruction, which method comprises performing a computer-implemented method of focusing electromagnetic radiation at a target as set out herein, the disordered medium being a surface of a building from which the electromagnetic radiation is scattered and reflected toward the object, whereby using the focusing spatial modulation pattern to transmit data to the receiver increases a signal to noise ratio of electromagnetic radiation at the receiver.

According to some embodiments there is provided an apparatus for performing a computer-implemented method of focusing electromagnetic radiation at a target, the electromagnetic radiation travelling to the target by reflection from a disordered medium, which apparatus comprises:
  a transmitter comprising:
  a computer processor, and
  a memory, the memory storing computer-executable instructions that, when executed, cause the transmitter to perform steps (a), (g) and (h) as set out above.

In an embodiment said memory stores computer-executable instructions that, when executed, cause the transmitter to perform steps (c). (d) and (c) as set out above.

According to some embodiments there is provided an apparatus for performing a computer-implemented method of focusing electromagnetic radiation at a target, the electromagnetic radiation travelling to the target by reflection from a disordered medium, which apparatus comprises:
  a receiver comprising:
  a computer processor, and
  a memory, the memory storing computer-executable instructions that, when executed, cause the transmitter to perform steps (b), (c). (d) and (e) as set out above.

According to some embodiments there is provided a kit for performing a computer-implemented method of focusing electromagnetic radiation at a target, the electromagnetic radiation travelling to the target by reflection from a disordered medium, which apparatus comprises the transmitter apparatus set out above and the receiver apparatus set out above.

According to some embodiments there is provided a method of performing one of deep tissue optical microscopy, optogenetics, micro-manipulation, laser microsurgery, laser-induced thermal therapy and photoacoustic imaging, which method comprises performing a computer-implemented method of focusing electromagnetic radiation at a target as set out herein, the disordered medium being an in vivo or in vitro human or animal or plant biological tissue.

An apparatus for performing a computer-implemented method of focusing electromagnetic radiation at a target, which apparatus comprises:

a transmitter comprising:
  a computer processor; and
  a memory, the memory storing computer-executable instructions that, when executed, cause the transmitter to perform steps (a), (g) and (h) as set out above.

In an embodiment said memory may store computer-executable instructions that, when executed, cause the transmitter to perform steps (c). (d) and (e) set out above.

According to some embodiments there is provided an apparatus for performing a computer-implemented method of focusing electromagnetic radiation at a target, which apparatus comprises:
  a receiver comprising:
  a computer processor: and
  a memory, the memory storing computer-executable instructions that, when executed, cause the transmitter to perform steps (b). (c), (d) and (e) set out above.

Some embodiments are based on our realisation that there is a pseudo-linearity, or approximate linearity, between the intensity of an input image transmitted through a disordered medium, such as a multi-mode optical fibre, and the intensity of an output image received from the disordered medium. The disordered medium may have an intensity transmission matrix that describes the relationship between the electromagnetic field input to the disordered medium and electromagnetic field output from the disordered medium.

This pseudo-linearity can be exploited to (i) characterize, or quantify, the intensity transmission matrix significantly faster than previous methods (e.g. model-based, or deep-learning), but with sufficient quality or precision to (ii) ensure that input images can be recovered accurately at a receiver. For example, we have characterized the intensity transmission matrix on the timescale of seconds, whereas use of deep-learning to determine a complex-valued transmission matrix may take several hours.

We have further discovered that this pseudo-linearity enables a computer to characterize the intensity transmission matrix (ITM) using real-valued constants, rather than complex-valued constants. This brings about the reduction in timescale for the disordered medium to be characterized.

It may be that this characterising process is performed by the computer using a data processing technique for acquiring and reconstructing the real-valued constants of the ITM from the output images. The output images may correspond to a series of known input images. The data processing technique may comprise use of a forward model linking the known input images to the output images with a series of linear equations, and using an algorithm to obtain the real-valued constants of the ITM by solving the series of linear of equations. The algorithm may be a linear inverse problem algorithm. In an embodiment the data processing technique may use compressive sensing to determine the real-valued constants.

An advantage of this is that the real-valued constants of the ITM can be obtained by matrix multiplication (for example using linear operators or other equivalent computer-implemented technique) which can be performed readily by the computer. This avoids any time-consuming iterative process of some prior methods. In embodiments characterisation of a MMF was performed within ~16 s (~8 s for data acquisition and ~8 s for processing) using input images having 1.024 pixels.

Once the ITM is determined by the computer, either the ITM itself or an equivalent representation of it, can be used to retrieve or reconstruct subsequent unknown input images from intensity-only output speckles received at a receiver from the disordered medium.

A further realization is that these subsequent input images may be reconstructed with accuracy provided their intensity distribution falls within or near the aforementioned region of pseudo-linearity. Accuracy may be indicated in a number of different ways, such as using a correlation coefficient between the input image and reconstructed image. Reconstructed images may have a high correlation with the input image compared to regions outside the region of pseudo-linearity. The acceptable level of accuracy may be application dependent. For example, the percentage of correctly reconstructed intensity values in the pixels of a reconstructed image may be 90% or more. If the input image comprises a pattern of binary values, a reconstructed image that is then binarized may have a percentage of correctly reconstructed binary values that is between 99% and 100%. This may be advantageous for digital data transmission for example. It may also be possible to increase reconstructed image accuracy using error correction techniques, such as those used in telecommunication that introduce a redundancy in the form of an error correcting code.

In some embodiments the intensity distribution may be quantified in terms of the number of 'on' (or light-transmitting) or 'off' (non-light transmitting) pixels in the input image relative to the total number of pixels. It may be that the pseudo-linearity is achieved when the number of 'on' pixels is high enough (or conversely when the number of 'off' pixels is low enough). In some embodiments high enough means that the ratio of 'on' pixels to 'off' pixels may be dependent on a desired correlation coefficient (or other accuracy parameter) between a reconstructed image and the input image. The correlation coefficient may indicate the number of correctly determined output pixels in the reconstructed image, and may be a value be 0 and 1 or a percentage. For example, the ratio may be set so that the correlation coefficient has a value of greater than 0.7 or 0.9 or 0.95 or 0.99. The particular lower threshold value for the correlation coefficient may be determined by the depending on the application.

It may be that the intensity distribution of an input image that does not have an intensity distribution falling within the pseudo-linear region, is manipulated so that it has a manipulated intensity distribution falling within the pseudo-linear region. For example, it might be possible to invert an intensity distribution of input image to achieve this (e.g. in a binary image inverting the 1s and 0s respectively).

It is noted that, after the characterizing process and the ITM has been determined, it is not essential for a subsequent input image to be within the region of pseudo-linearity between the input and output intensity. For example, it may be that reconstructed images do not need a high correlation with the input image.

A disordered medium may be a multi-mode optical fibre, a multi-core optical fibre bundle, an Anderson localization fibre, an optical diffuser, a biological tissue, an air-core multi-mode core fibre, or a diffuser such as a lens with an opaque diffuser, and thin papers. The disordered medium may be quasi-static, by which is meant that the disordered medium has a substantially stable transmission matrix for a given period of time or whilst present physical parameters prevail (e.g. temperature, bending). If the transmission matrix changes after a period of time, the characterization process may be repeated to determine a new ITM.

Some advantages of embodiments of the invention may include, but may not be limited to high-speed characterisation of the disordered medium. Both the training process of neural network and the model-based algorithm rely on iterative optimization that is very time-consuming. Furthermore, they required a large training dataset and hence a relatively long data acquisition time. On contrary, embodiments described herein may only require simple matrix manipulation (or any computational equivalent) to determine the TIM, saving data acquisition and computation time. Furthermore the real-valued transmission constants of the ITM are not dependent on the known input images and therefore the types of input images subsequently transmitted is not limited to images that are similar to the training dataset.

In an embodiment there is provided a computer-implemented method of transmitting through a disordered medium from a transmitter to a receiver an image represented as input electromagnetic radiation. The disordered medium may have a transmission matrix comprising a plurality of complex-valued transmission constants that relate said input electromagnetic radiation to output electromagnetic radiation at said receiver. The method may comprise the steps of:

performing a characterising process on said disordered medium to determine said transmission matrix;
said transmitter may be used to transmit said image through said disordered medium;
a reconstruction process may be performed using said transmission matrix to generate a reconstructed image from the output electromagnetic radiation at said receiver;
in said characterisation process the step of determining said transmission matrix may comprise:
determining said complex-valued transmission constants as real-valued transmission constants by using an approximately linear, or pseudo-linear, relationship between said input electromagnetic radiation and said output electromagnetic radiation; and
said real-valued transmission constants may be used to generate and store a version of the transmission matrix;
and said reconstruction process may comprise the steps of:
generating an output signal comprising intensity or amplitude values of said output electromagnetic radiation;
said reconstructed image may be generated by combining said output signal and said version of the transmission matrix in a way that effects a matrix multiplication of an inverse of said transmission matrix and said output signal; and
said reconstructed image may be output from said receiver.

In an embodiment the step of determining said transmission matrix may comprise the step of using a data processing technique having a forward model that links the image to the output signal with a series of linear equations. An algorithm may be used to obtain the real-valued transmission constants of the transmission matrix by solving the series of linear of equations.

In an embodiment the step of determining said transmission matrix may comprise the step of using a compressive sensing technique to determine said real-valued transmission constants.

In an embodiment the compressive sensing technique may use a measurement matrix that satisfies the restricted isometry property such as a Hadamard matrix, a random matrix having a Gaussian or Bernoulli distribution, a random Fourier ensemble matrix, a deterministic matrix such as a second-order Reed-Muller code matrix, a Chirp sensing matrix, a binary Bose-Chaudhuri-Hocquenghem code matrix, or a quasi-cyclic low-density parity-check code matrix.

In an embodiment said characterising process may comprise the step of:
at said transmitter:
providing a plurality of controllable electromagnetic radiation sources for transmitting said image.

In an embodiment said characterising process may further comprise the step of transmitting into said disordered medium a plurality of known input images, the plurality of known input images known to the receiver without being received through said disordered medium. Each known input image may comprise an intensity pattern so that each controllable electromagnetic radiation source of said plurality of controllable electromagnetic radiation sources is either on or off during the transmitting step.

In an embodiment said intensity pattern comprises a binary or grayscale intensity pattern.

In an embodiment the method may comprise the step of generating said intensity pattern from a generating matrix that ensures that each intensity pattern generated is orthogonal to each other intensity pattern.

In an embodiment said characterising process may further comprise the steps of, at said receiver, providing a plurality of electromagnetic radiation detectors. A plurality of output images may be received from said disordered medium with said plurality of electromagnetic radiation detectors, and each output image may comprise said output electromagnetic radiation field in the form of an intensity speckle pattern corresponding to one of said plurality of known input images. Said known input images and said output images may be processed to determine said real-valued transmission constants.

In an embodiment the step of determining said real-valued transmission constants may comprise:

for a first pair, mn, of electromagnetic radiation detector in (m=1, 2, . . . . m) and electromagnetic radiation source n (n=1, 2, . . . N):
take the first input and output image pair (p=1) and determine the product of (i) the measured output electromagnetic intensity or amplitude at electromagnetic radiation detector in and (ii) a binary value indicating whether the corresponding electromagnetic radiation source n of the pair mn was on or off for that input and output image pair p (p=1);
repeat step (a) for each input and output image pair p (p=2, 3, . . . , P);
sum the products obtained in steps (a) and (b);
divide said sum by the number of electromagnetic radiation sources N and store the result as the mnth real-valued transmission constant in said transmission matrix;
repeat steps (a) to (d) for each other pair of electromagnetic radiation detector m and electromagnetic radiation source n to generate m×n real-valued transmission constants.

In an embodiment an accuracy parameter, that represents a similarity of said reconstructed image to said image, may be a function of the intensity of said input electromagnetic radiation. The approximately linear relationship may exist as a portion or range of said function. The method may further comprise the step of transmitting said image with an input electromagnetic radiation intensity so that the accuracy parameter of said reconstructed image has a value within or outside said portion or range.

In an embodiment the step of transmitting said input image with an input electromagnetic radiation intensity may be by controlling an intensity distribution of said input image. In an embodiment the intensity distribution may comprise an intensity pattern.

In an embodiment said portion or range may exist above a threshold of said input electromagnetic radiation intensity. The accuracy parameter may have a value that is close to a maximum above said threshold. The method may further comprise the step of:
(i) transmitting said input image with input electromagnetic radiation intensity above said threshold to obtain said reconstructed image with an accuracy parameter close to or at said maximum; or
(ii) transmitting said input image with input electromagnetic radiation intensity below said threshold to obtain said reconstructed image with an accuracy parameter that is lower than said maximum.

In an embodiment said image may comprise a binary pattern and said reconstructed image comprises a grayscale image. The reconstruction process may further comprise the step of binarizing said grayscale image to generate a binarized reconstructed image. Alternatively said image may comprise a grayscale pattern and said reconstructed image comprises a grayscale image.

In an embodiment the method may comprise the step of repeating said characterising process to determine a new transmission matrix.

In an embodiment said image may comprise a binary pattern or grayscale pattern indicating at least two bits. The transmission of different binary patterns or grayscale patterns from image to image may facilitate digital communication through said disordered medium.

In an embodiment each controllable electromagnetic radiation source of said plurality of controllable electromagnetic radiation sources may be an input pixel or input voxel usable for transmitting a portion of said image into said disordered medium.

In an embodiment each electromagnetic radiation detector of said plurality of electromagnetic radiation detectors may be an output pixel usable for receiving a portion of said intensity speckle pattern from said disordered medium.

In an embodiment there may be multiple output pixels for each input pixel. For example, there may be three output pixels for each input pixel.

In an embodiment said image may be generated by illuminating a target with electromagnetic radiation, the electromagnetic radiation being scattered and reflected from said target. The disordered medium may be positioned to receive a portion of said scattered and reflected electromagnetic radiation as said image. The target may be a tissue or organ within the human or animal body.

In an embodiment the method may comprise the step of determining said transmission matrix for a plane behind said disordered medium, whereby said reconstructed image is a 2D image of said target.

In an embodiment said transmission matrix may be determined for a plurality of substantially parallel planes behind said disordered medium, whereby each reconstructed image may be a 2D image of said target in a different plane. The reconstructed images may be combined to generate a 3D image of said target.

In an embodiment the step of illuminating the target with electromagnetic radiation may comprise illuminating the target with a plurality of wavelengths. The step of receiving may comprise receiving a portion of said scattered and reflected electromagnetic radiation at each wavelength of said plurality of wavelengths.

In an embodiment said electromagnetic radiation may be coherent. In an embodiment said electromagnetic radiation may comprise one or more wavelength within, but not limited to, the ultraviolet (about 10 nm to about 400 nm), visible (about 400 nm to about 700 nm) or near-infrared (about 0.75 μm to 1.4 μm or 1.7 μm, including any one of the O-, E-, S-, C-, and L-bands in optical communications) portions of the electromagnetic spectrum.

In an embodiment said disordered medium comprises a quasi-static disordered medium. Quasi-static may mean that the disordered medium has a transmission matrix that is approximately stable for a short period of time (e.g. minutes, hours or days) but which may not be stable over a longer period of time (e.g. days or weeks). Quasi-static may mean that the disordered medium has a transmission matrix that is stable under conditions at the time. If those conditions change, then then transmission matrix may change. Such conditions may include temperature and physical properties (e.g. bending).

In an embodiment said disordered medium may comprise a multi-mode optical waveguide, such as a graded-index or step-index multi-mode optical fibre, or a multicore optical fibre. These waveguides or fibres may have core diameters greater than about 50 μm and lengths in any of the ranges: centimetre, metre, tens of metres, hundreds of metres and kilometres.

In an embodiment said version of the transmission matrix may comprise:
(i) the real-valued transmission constants stored as a matrix processable by a computer;
(ii) any computer-processable equivalent representation of (i); or
(iii) any computer-processable representation the inverse of (i).

In an embodiment there may be provided an apparatus for use in the computer-implemented method as set out above or described herein. The apparatus may comprise a plurality of controllable electromagnetic radiation sources for transmitting said image. There may be a computer processor. There may be a memory that may store computer-executable instructions that, when executed, cause said transmitter to transmit into said disordered medium a plurality of known input images, and the plurality of known input images may be known to the receiver without being received through said disordered medium. Each known input image may comprise an intensity pattern so that each controllable electromagnetic radiation source of said plurality of controllable electromagnetic radiation sources is either on or off during the transmitting step.

In an embodiment the computer-executable instructions may be adapted to cause said transmitter to perform the transmitter steps as set out above or as described anywhere herein.

In an embodiment said plurality of controllable electromagnetic radiation sources may be arranged in a 1D or 2D array.

In an embodiment said plurality of controllable electromagnetic radiation sources may comprise a light transmitter array unit.

In an embodiment said light transmitter array unit may comprise a plurality of sources of coherent laser light. In an embodiment each source of laser light may be individually controllable by said computer processor to be either on or off, or to vary the transmitted intensity over time.

In an embodiment each source of said plurality of sources of coherent laser light may comprise a laser diode, a solid-state laser such as a neodymium-doped yttrium aluminium garnet (Nd:YAG) laser, a neodymium-doped glass (Nd:glass) laser, a Ruby laser, a neodymium-doped yttrium lithium fluoride (Nd:YLF) laser, a ytterbium-doped yttrium aluminum garnet (Yb:YAG) laser, a ytterbium-doped fibre (Yb:fibre) laser, a titanium-sapphire (Ti:sapphire) laser, or a vertical-cavity surface emitting laser (VCSEL).

In an embodiment the apparatus may further comprise a light modulator array unit for modulating electromagnetic radiation from said plurality of controllable electromagnetic radiation sources.

In an embodiment said plurality of controllable electromagnetic radiation sources may always be on during use and said light modulator array unit may be controllable by said computer processor to generate said intensity pattern in said image.

In an embodiment said light modulator array unit may comprise a spatial light modulator. In an embodiment said spatial light modulator may comprise a digital micromirror device comprising an array of micromirrors. Each micromirror may be one controllable electromagnetic radiation source of said plurality of controllable electromagnetic radiation sources.

In an embodiment the apparatus may further comprise a single laser for producing coherent laser light. In an embodiment said spatial light modulator may be arranged to modulate discrete portions of said coherent light thereby acting as said plurality of controllable electromagnetic radiation sources.

In an embodiment each controllable electromagnetic radiation source of said plurality of controllable electromagnetic radiation sources may be an input pixel or input voxel usable for transmitting a portion, such as one bit, of said image into said disordered medium.

In an embodiment said disordered medium may comprise an optical waveguide, and said transmitter may be adapted to transmit light at an optical wavelength into said optical waveguide.

In an embodiment there is provided a network interface module, such as a small form-factor pluggable transceiver (SPF), a photonic integrated circuit (PIC), an application-specific integrated circuit (ASIC), or system-on-a-chip comprising a transmitter as set out above or as described anywhere herein.

In an embodiment there is provided an optical communication system comprising a transmitter as set out above or as described anywhere herein or a network interface module as set out above or as described herein.

In an embodiment there is provided an apparatus for use in the computer-implemented method which apparatus may comprise a receiver for receiving said output electromagnetic radiation from said disordered medium. Them may be a computer processor. There may be a memory, the memory storing computer-executable instructions that, when executed, cause said receiver to perform the characterisation process as set out above or as described herein. Said complex-valued transmission constants may be determined as real-valued transmission constants by using an approximately linear relationship between said input electromagnetic radiation and said output electromagnetic radiation. Said real-valued transmission constants may be used to generate and store a version of the transmission matrix. The reconstruction process may comprise generating an output signal comprising intensity or amplitude values of said output electromagnetic radiation. The reconstructed image may be generated by combining said output signal and said version of the transmission matrix in a way that effects a matrix multiplication of an inverse of said transmission matrix and said output signal. The reconstructed image may be output from said receiver.

In an embodiment the computer-executable instructions are adapted to cause the receiver to perform the receiver steps as set out above or as described anywhere herein.

In an embodiment said receiver may comprise a plurality of electromagnetic radiation detectors.

In an embodiment said plurality of electromagnetic radiation detectors may comprise a light detector array unit, such as a charge-coupled device (CCD) array or a complementary metal-oxide-semiconductor (CMOS) array.

In an embodiment each electromagnetic radiation detector of said plurality of electromagnetic radiation detectors may comprise a photodetector, such as a photodiode.

In an embodiment each electromagnetic radiation detector of said plurality of electromagnetic radiation detectors may be an output pixel usable for receiving a portion of said intensity speckle pattern from said disordered medium.

In an embodiment, the apparatus may further comprise an analogue-to-digital converter (ADC) for converting said output electromagnetic radiation to into a plurality of digital values representing electromagnetic radiation intensity at said receiver.

In an embodiment said disordered medium may comprises an optical waveguide. The receiver may be adapted to receive light at an optical wavelength from said optical waveguide.

In an embodiment there is provide a network interface module, such as a small form-factor pluggable transceiver (SPF), a photonic integrated circuit (PIC), an application-specific integrated circuit (ASIC), or system-on-a-chip comprising a receiver as set out above or as described anywhere herein.

In an embodiment there is provided an optical communication system comprising a receiver set out above or as described anywhere herein, or a network interface module as set out above or as described anywhere herein.

In an embodiment there is provided an optical communication system comprising a transmitter as set out above or as described anywhere herein, a receiver as set out above or as described anywhere herein and an optical waveguide between the transmitter and the receiver.

In an embodiment there is provided an apparatus for performing an endoscopy, which apparatus may comprise a tube adapted to be inserted into a body. The tube may have a proximal end and a distal end. There may be a first optical waveguide, having a first end and a second end. A portion of the first optical waveguide may be housed in said tube so that said first end is adjacent said distal end of said tube. There may be a receiver as set out above or as described anywhere herein, said second end of said first optical waveguide connected to said receiver. There may be a light source. There may be a second optical waveguide connected to said light source. The second optical waveguide may have a portion housed in said tube so that in use light is guided from said light source to said distal end of said tube. There may be a transmitter as set out above or as described anywhere herein for characterising said first optical fibre prior to use.

BRIEF DESCRIPTION OF THE DRAWINGS

FIG. 1B is a schematic diagram of a characterisation process to characterise a disordered medium;

FIG. 1C is a schematic diagram of an image reconstruction process using the apparatus of FIG. 1A;

FIG. 16A is an image of a speckle pattern at the end of a multi-mode optic fibre before any characterisation process and spatial modulation;

FIG. 16B is an example of focusing spatial modulation pattern determined according to a method in accordance with the present invention:

FIG. 16C is an image of light focused onto a first region of a CCD camera when light is spatially modulated using the pattern of FIG. 16B;

FIGS. 16F-16H are photoacoustic images constructed using a method according to the present invention;

FIGS. 17A-17D are schematic diagrams various tip arrangements for optical fibres for use in methods of photoacoustic imaging;

FIG. 18 is a schematic diagram of an apparatus providing a dual imaging modality;

FIG. 22 is a table showing results of comparison of various different algorithms of spatial light modulation;

DETAILED DESCRIPTION OF THE PREFERRED EMBODIMENTS

Figure 1A:
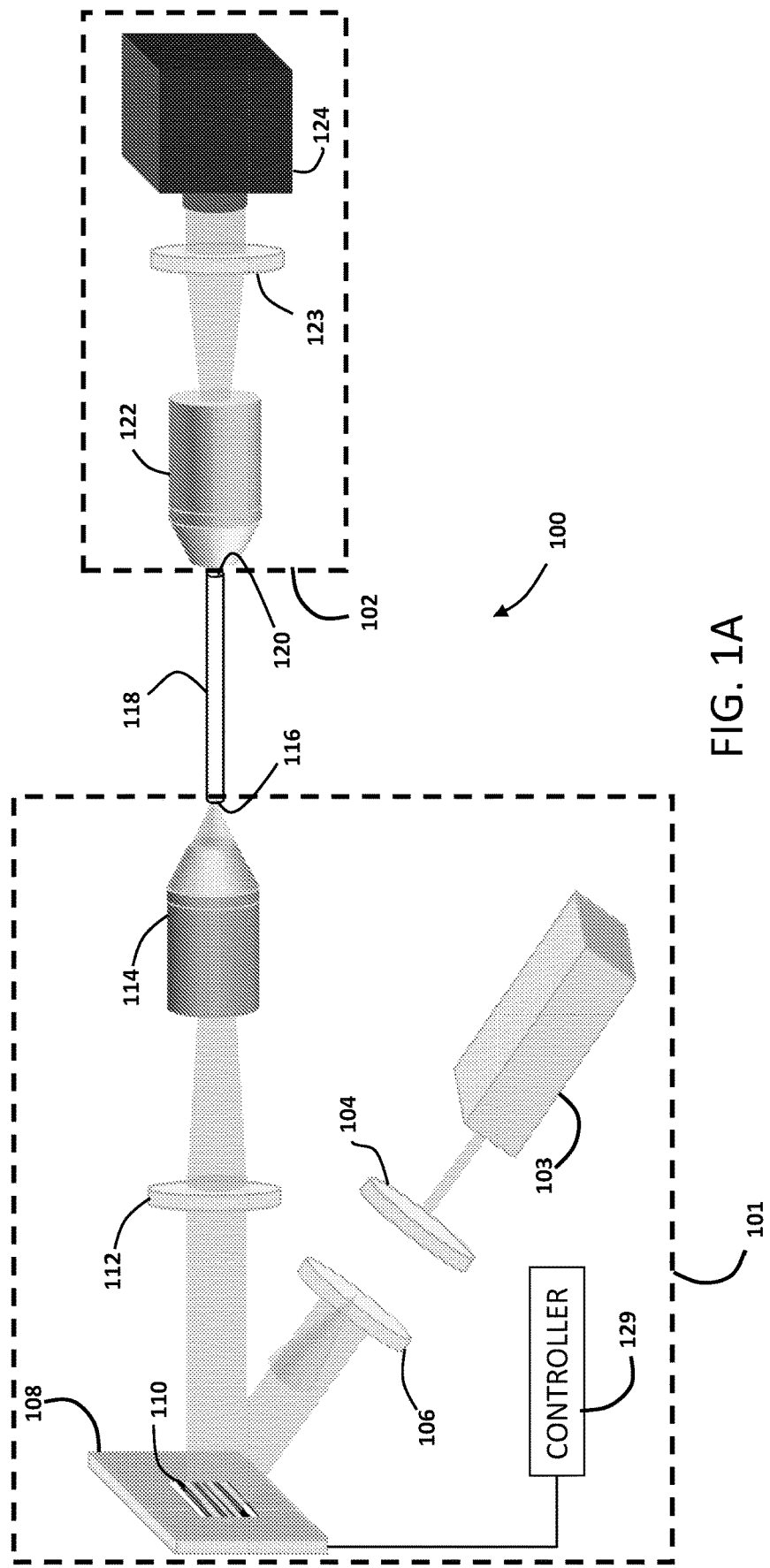
FIG. 1A is a schematic diagram of an apparatus according to an embodiment of the present invention.

Referring to FIG. 1A an apparatus for transmission and reception of an image through a disordered medium is generally identified by reference numeral 100. The image may represent a binary sequence of data (such as a digital bit stream or byte stream for example) and the apparatus may be adapted to transmit a plurality of different images over time whereby the apparatus is useful for parallel communication; that is to say two or more binary digits bits of data may be transmitted simultaneously in each image. The image transmission may take place through a disordered medium such as an optical fibre, and may be through a multi-mode optical fibre.

As used herein a disordered medium may be any quasi-static medium in which light is scattered multiple times as it passes through the medium. The disordered medium may be any medium that comprises a heterogenous spatial distribution of optical refractive index or speed of light in the medium. Examples of such disordered medium include, but are not limited to, multi-mode optical fibres (both graded and step-index), optical diffusers, and tissues of the human or animal body.

The apparatus comprises a transmitter 101 and a receiver 102. The transmitter 101 may be adapted for inputting, or projecting, coherent light into one end a multi-mode optical fibre 118. As such the transmitter may comprise a plurality of controllable electromagnetic radiation sources. The receiver 103 may be adapted receive light leaving the opposite end of the multi-mode optic fibre 118. As such it may comprise a plurality of electromagnetic radiation detectors.

The transmitter 101 may comprise a laser 103. The laser 103 may be an actively Q switched diode pumped solid state laser such as the SPOT-10-200-532 laser available from Elforlight. The SPOT-10-200-532 is adapted to produce a beam of coherent light at 532 nm with a minimum pulse width of <1.8 ns and a maximum pulse energy of 10 µJ (at ≤10 kHz). The spatial mode of the laser is $TEM_{00}$ with a beam diameter ~1 mm.

A first tube lens 104 may be positioned to receive the beam of light from the laser 103. The first lens 104 may be an achromatic doublet-type having a focal length of 30 mm, a diameter of 25.4 mm, SM1-threaded mount and anti-reflective coating for the range 400-700 nm. A suitable lens is available from Thorlabs. Inc. under code AC254-030-A-ML. A second tube lens 106 may be positioned after the first tube lens 104. The second tube lens 104 may be an achromatic doublet-type having a focal length of 75 mm, a diameter of 25.4 mm SM1-threaded mount and anti-reflective coating for the range 400-700 nm. A suitable lens is available from Thorlabs. Inc. under code AC254-075-A-ML.

The transmitter 101 may further comprise a digital micromirror device (DMD) 108 that may be arranged to receive light from the lens 106. The DMD 108 comprises an array of micromirrors 110 for spatially modulating the laser light from the laser 103, and which may act as the aforementioned a plurality of sources of electromagnetic radiation. The DMD 108 may be a DLP7000 available from Texas Instruments. Inc. The DMD 108 comprises an array of 1024×768 micromirrors. Other array sizes are possible.

The transmitter 101 may further comprise a third tube lens 112 that may be positioned to receive spatially modulated light from the DMD 108 and pass the beam of light to a first objective lens 114. The third tube lens 112 may be an achromatic doublet such as an AC254-050-A-ML available from Thorlabs which has a focal length of 50 mm. The purpose of the third tube lens 112 is to focus the spatially modulated light onto the first objective lens 114. The first objective lens 114 may be an infinity-corrected plan achromat such as an RMS20X available from Thorlabs. The purpose of the first objective lens is to focus the beam of light onto the proximal end 116 of a multi-mode fibre ('MMF') 118. As explained in greater detail below, three different MMFs were tested in the apparatus 100.

A distal end 120 of the MMF 118 may be positioned to guide the laser light to the receiver 102. The receiver 102 may comprise a second objective lens 124 which receives the laser light from the distal end 120. The second objective lens 122 may be the same type of lens as the first objective lens 114, such as the RMS20X. The second objective lens may be positioned to improve the collimation of the laser light leaving the MMF 118. A second tube lens 123 may be positioned to receive laser light from the second objective lens 122 and to further collimate the laser light. The second tube lens may be an achromatic doublet such as an AC254-100-A-ML available from Thorlabs which has a focal length of 100 mm.

The receiver 101 may further comprise a CCD camera 124 that may be positioned to capture laser light from the second objective lens 122. The CCD camera comprises a plurality of output pixels which may act as the aforementioned plurality of electromagnetic radiation detectors. The CCD camera may be a CMOS device such as model C11440-22CU01 available from Hamamatsu. The C1440-22CU01 provides 4.0 megapixels resolution at 100 frame/s with 37,000:1 dynamic range. Output data from the CCD camera 124 may be captured and stored by a computer processor 126 and a memory 127.

In use an input image representing a binary sequence of data may be transmitted from the DMD 108 to the CCD camera 124 via the MMF 118. In particular, the laser 103 may generate a beam of coherent light 128 having a wavelength of 532 nm. The lenses 104 and 106 may spread and collimate the beam 128 so that its diameter increases from 1.0 mm to 2.5 mm.

Each micromirror of the DMD 108 may controlled by a controller 129 (which may comprise a computer processor and memory) so that a portion of the beam 128 is either reflected toward or away from the third tube lens 112. By reflecting a portion of the beam 128 toward or away from the third tube lens 112, the DMD 108 may be used to send a binary sequence of data through the MMF 118. For example, it may be that reflecting a portion of the beam 128 toward the third tube lens 112 indicates a '1' and reflecting a portion of the light away from the third tube lens 112 indicates a '0', or vice-versa. As each micromirror of the array 110 is independently controllable in this way, parallel communication of the binary sequence is possible.

However, the MMF 118 supports a number of propagation modes that cause the image to become spread in time as the beam 128 travels along the MMF 118. This modal dispersion affects the beam 128 so that a speckle pattern is seen by the CCD camera 124 rather than the image transmitted by the DMD 108. The speckle pattern is a seemingly random variation in the intensity of the beam 128 across its diameter, and it appears that the modulation applied by the DMD 108 to the beam 128 is lost by the time the beam 128 is received by the CCD camera 128.

The electric field component $E_m$ of the coherent light field at the $m^{th}$ output pixel of the CCD camera 124 received from the distal end 120 of the MMF 118 can be expressed as:

$$E_m = \Sigma_{n=N} t_{mn} \cdot E_n \quad (1)$$

where $E_n$ is the electric field component of the light field at the $n^{th}$ input pixel of the DMD 108, with a total of N input pixels. In other words, the electric field $E_m$ at the $m^{th}$ output pixel is the sum of the electric field $E_n$ from each of the N input pixels. However the electric field from each input pixel is modified by a complex-valued intensity transmission constant, $t_{mn} = A_{mn} e^{i\Theta_{mn}}$, that links $E_n$ with $E_m$. In this way there are N complex-valued transmission constants for each output pixel m.

$E_m$ and $E_n$ can be expressed as $E_m = A_m e^{i\Theta_m}$ and $E_n = A_n e^{i\Theta_n}$ with amplitude A and phase θ. As explained above, in binary modulation each micromirror of the DMD 108 can be switched between two states ('ON' or 'OFF') independently, with the 'ON' micromirrors deflecting a portion of the beam 128 onto the proximal end 116 of the MMF 118. Since the beam 128 is coherent, the light fields at all input pixels of the DMD 108 are assumed to have the same phase and amplitude. Thus, the phase $\theta_n$ is 0 whilst the amplitude $A_n$ is either 1 ('ON') or 0 ('OFF'). Hence, the light intensity at then $n^{th}$ input pixel is also either 1 ('ON') or 0 ('OFF'), and the light intensity $I_m$ at the $m^{th}$ output pixel can be expressed as:

$$I_m = |\Sigma_{n=N} t_{mn} \cdot I_n|^2 \quad (2)$$

When all the micromirrors are switched 'ON' ($I_n=1$), each micromirror appears to the receiver (CCD camera 124) to produce a specific output light field with the same phase and amplitude as those of $t_{mn}$. FIG. 2A shows a schematic illustration of the CCD camera 124 having an array of output pixels 127. It will be recalled that each micromirror of the DMD 108 is 'ON' and is therefore directing a portion of the light, beam 128 toward the MMF 118. The electric field $E_m$ received by each output pixel 127*a* is schematically shown as a phasor 127*b*. It can be seen that the phase of $E_m$ is variable from output pixel to output pixel, even though each micromirror (input pixels) of the DMD 108 has the same phase. This difference is due to the modal dispersion in the MMF 118, and is approximated by the complex-valued intensity transmission constants described above.

Figure 2B:
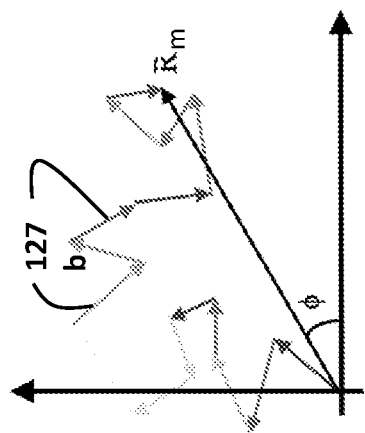
FIG. 2B is a schematic diagram of a phasor representing the total output light field from the output pixel array of FIG. 2A.

Referring to FIG. 2B the contributions 127*b* from all the micromirrors of the DMD 108 form a total output light field $R_m$ with phase $\emptyset_m$ and amplitude $A_{R_m}$ at the distal end 120 of the MMF 118. The amplitude $A_{R_m}$ can be considered as the superposition of all of the transmission constants $t_{mn}$ that are projected on $R_m$, and the intensity $I_{R_m}$ can also be expressed as:

$$I_{R_m}=A_{R_m}^2=A_{R_m}|\Sigma_{n=N}A_{mn}\cos(\theta_{mn}-\emptyset_{mn})|\cdot I_n \quad (3)$$

Figure 2D:
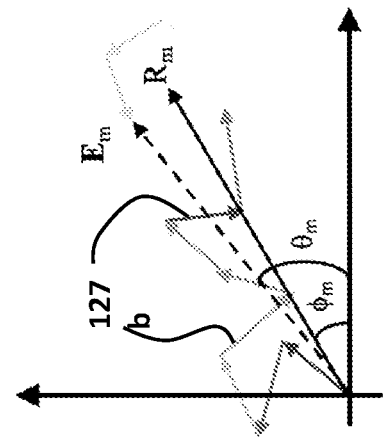
FIG. 2D is a schematic diagram of a phasor representing the total output light field from the output pixel array of FIG. 2A and a phasor representing the total output light field from the output pixel array of FIG. 2C.
Figure 2A:
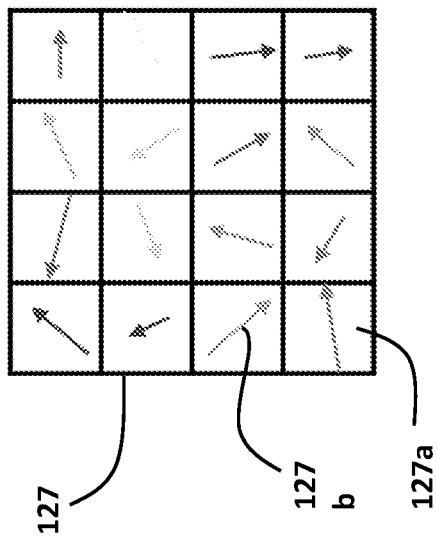
FIG. 2A is a schematic diagram of an output pixel array illustrating magnitude and phase of light at each output pixel when all output pixels are 'on'.
Figure 2C:
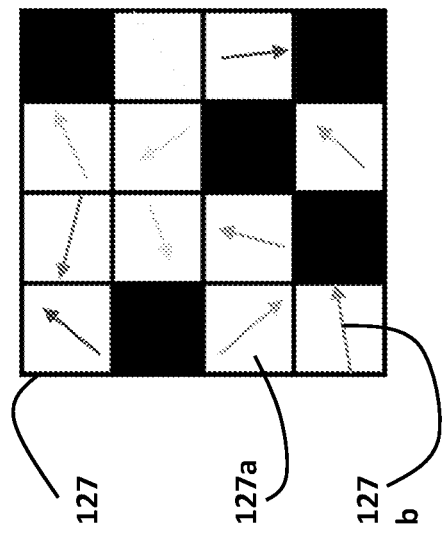
FIG. 2C is a schematic diagram of an output pixel array illustrating magnitude and phase of light at each output pixel when only some output pixels are 'on'.

Now considering the case when a binary pattern is input to the DMD 108 (see FIG. 2C), only a portion of the micromirrors of the DMD 108 are 'ON'. The total output field $E_m$ at the $m_{th}$ output pixel is generated with a phase $\theta_m$ and an amplitude $A_m$ (see FIG. 2D). The intensity, $I_m$, of the total output field can be expressed as:

$$I_m=A_m\Sigma_m|\Sigma_{n=N}A_{mn}\cos(\theta_{mn}-\theta_m)|\cdot I_n \quad (4)$$

We can define a ratio, $\alpha_m$, of the amplitude of the total light field when all micromirrors are 'ON' on the DMD 108 to the amplitude of the total light field when fewer than all micromirrors are 'ON' as:

$$\alpha_m = \frac{A_{R_m}}{A_m} \quad (5)$$

A ratio, $\beta_m$, of the phase difference of the total light field when all micromirrors are 'ON' on the DMD 108 to the phase difference of the total light field when fewer than all micromirrors are 'ON' can be expressed as:

$$\beta_m = \frac{\left|\sum_{n=N}A_{mn}\cos(\theta_{mn}-\emptyset_{mn})\right|}{\left|\sum_{n=N}A_{mn}\cos(\theta_{mn}-\theta_m)\right|} \quad (6)$$

Finally a parameter, $\theta_m$, which represents the ratio of the intensity of total light field when all micromirrors are 'ON' on the DMD 108 to the intensity of the total light field when fewer than all micromirrors are 'ON' can be expressed as can be defined as $\theta_m=\alpha_m\beta_m$. Following that, the intensity of the total output field when some fraction of the micromirrors is on can be re-written as:

$$I_m = \frac{1}{\eta_m}A_{R_m}\left|\sum_{n=N}A_{mn}\cos(\theta_{mn}-\emptyset_{mn})\right|\cdot I_n \quad (7)$$

Interestingly, it was found that when the number of input pixels that are switched 'ON' (J) is sufficiently large compared to the total number of input pixels (N), the value of the parameter $\eta_m$ remained mostly consistent across all output pixels m, with a mean value of $\eta$ and a small standard deviation (described in greater detail below).

In other words, when J is sufficiently large, there is a pseudo-linear (or approximately linear) relationship between the intensity of the input image and the intensity of the output image. This pseudo-linearity enables the system (i.e. input image, disordered medium and output image) to be approximated with a set of linear equations, and the constants of the intensity transmission matrix may be determined using a compressive sensing technique. A particular advantage of this is that the intensity transmission constants become real-valued, rather than complex-valued. Another particular advantage is that the real-valued intensity transmission constants may be determined quickly and with low computational overhead compared to the model-based and deep-learning methods mentioned elsewhere herein.

As such it is possible to approximate the output intensity at each pixel m from the input intensities due to the number of 'ON' input pixels, J, using a matrix containing real-values of the intensity transmission constants $t_{mn}$. This matrix is herein called an intensity transmission matrix (ITM) and the output light intensity, $I_m$, at the m° $^i$ output pixel may be approximated as:

$$I_m \approx |\Sigma_{n=N}itm_{mn}|\cdot I_n \quad (8)$$

where $$itm_{mn} = \left(\frac{1}{\eta}\right)A_{R_m}A_{mn}\cos(\theta_{mn}-\emptyset_{mn}) \quad (9)$$

are the real-valued intensity transmission constants (the elements in the ITM) linking $I_n$ with $I_m$. Hereinafter the real-valued intensity transmission constants will be called the 'RVITCs'.

As the variation (e.g. expressed in terms of standard deviation) of $\eta$ across all output pixels decreases as J increases, when the variation of $\eta$ is sufficiently small compared to the mean value of $\eta$, an input intensity pattern (i.e. image 130). $I_{in}$, may be reconstructed from the output intensity pattern 134. $I_{out}$, by inverting the ITM as:

$$I_{in} \approx (ITM)^{-1}*I_{out} \quad (10)$$

In some embodiments the ITM may be inverted using other equivalent techniques, such as solving for the inverse linear problem using any available method including through matrix factorisations or iterative (potentially matrix-free) solvers.

By 'high quality' it is meant that the reconstructed image has a correlation coefficient with the input image of 90% or higher.

As described above, we have realised that it is possible to recover the image generated by the DMD 108 from the intensity speckle pattern at the CCD camera 124.

In this way a receiver may determine the image sent by a transmitter through a MMF 118 (or other disordered medium) whereby the binary sequence of data may be determined. In order to recover the binary sequence, a characterization process is performed on the MMF 118 to determine the RVITCs $itm_{mn}$.

The characterization process may comprise the use of compressive sensing to determine the RVITCs. In particular the characterization process may comprise steps of generating a series of known input images, each input image comprising a pattern representing a plurality of binary values. Each input image may be independent of each other input image (for example, the input images may be such that no input image is a linear combination of any other image). The pattern may be stored as an input matrix (or other computer-processable equivalent). Each input image may be transmitted from the transmitter 101 into the disordered medium (e.g. MMF 118). An output image may be received at the receiver 102 (e.g. CCD camera 124) from the disordered medium in the form of an intensity-only output speckle pattern (i.e. with no phase information). The values of each output intensity pattern may be stored in the computer memory 126 as an output matrix (or other computer-processable equivalent). The values of each intensity pattern may for one column of the output matrix. Each value may correspond to a pixel of the receiver 102 or may be derived from a plurality of pixels of the receiver 102. The input and output matrices may be used as a system of linear equations to determine an intensity transmission matrix comprising a plurality of intensity transmission constants. The intensity transmission matrix may be stored in a computer memory for later use. Alternatively an equivalent representation or any representation of its inverse may be stored in a computer memory for later use.

The system of linear equations to be solved may be expressed as:

$$\begin{bmatrix} I_1^1 & \cdots & I_1^p \\ \vdots & \ddots & \vdots \\ I_m^1 & \cdots & I_m^p \end{bmatrix} = ITM \cdot [H_1, H_2] \quad (11)$$

In terms of compressive sensing, the left-hand side of this equation represents the measurements. The ITM 132 is the sparse matrix and the measurement matrix is $[H_1, H_2]$, which is generated from a Hadamard matrix. The generation of $[H_1, H_2]$ is explained in greater detail below.

Although the matrix on the left-hand side of Eq. (11) may appear to have a large number of values, it is in fact a small number of the possible measurements of the system (i.e. transmitter, multi-mode fibre 118, and receiver). If the ITM 132 were to be found using traditional linear algebra techniques, it would be necessary to input all possible binary input patterns and record all corresponding output images. This is not possible for binary patterns of any appreciable size. For example, an 8×8 binary pattern has $2^{64}$ possible images. In contrast, by using compressive sensing, 2N input images can be used and the RVITCs determined in seconds. Recalling that N is the number of input pixels of the DMD 108, in this example 2N=2×(32×32)=2048 images) which is a much smaller number. As mentioned elsewhere, it is not essential 2N images are used, and this number could be smaller or larger.

Other measurement matrices that are used in compressive sensing can be used to determine the ITM 132, as long as these matrices have the restricted isometry property. Examples of other measurement matrices include random matrices that are generated to follow a certain type of distributions such as Gaussian. Bernoulli. and random Fourier ensembles, and deterministic matrices such as second-order Reed-Muller codes. Chirp sensing matrices, binary Bose-Chaudhuri-Hocquenghem codes, and quasi-cyclic low-density parity-check code matrix. Particular reference is made to Arjoune Y, Kaabouch N. El Ghazi H, Tamtaoui A. *A performance comparison of measurement matrices in compressive sensing*, International Journal of Communication Systems. 2018 Jul. 10; 31(10):e3576, which is herein incorporated by reference.

Figure 1D:
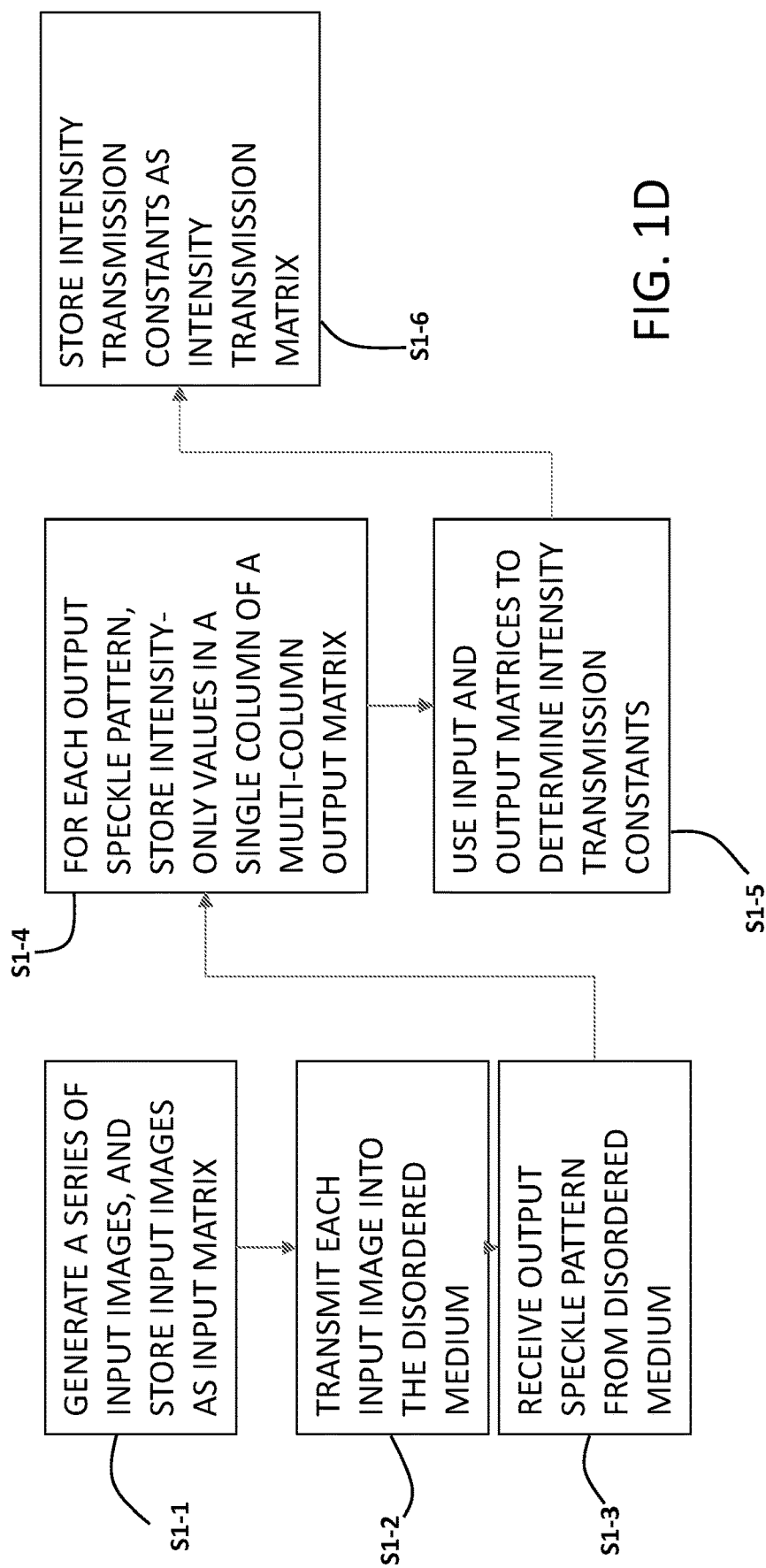
FIG. 1D is a schematic diagram of steps of the characterisation process of FIG. 1B.

An embodiment of the characterization process is illustrated in FIGS. 1B and 1D. At step S1-1 a plurality of input images 130 may be generated as described above. In this embodiment there may be 2N input images 130. At step S1-2 the 2N input images 130 may be transmitted sequentially into the disordered medium, such as the MMF 118. Each input image 130 is affected by modal dispersion within the MMF 118, and as described above, this is approximated by multiplication between each input image and the ITM 132. At step S1-3 a corresponding plurality of output images 134 is received by the CCD camera 124. Each output image 134 may comprise an intensity-only speckle pattern in which the corresponding input image 130 cannot be recognized by the human eye. Phase information is not captured by the CCD camera 124.

To construct the input images 130, a generating matrix such as a Hadamard matrix $H \in (-1, +1)$ was constructed with dimension N×N using Sylvester's method (for further details attention is directed to J. J. Sylvester. *Thoughts on inverse orthogonal matrices, simultaneous sign successions, and tessellated pavements in two or more colours, with applications to Newton's rule, ornamental tile-work, and the theory of numbers*. Philosophical Magazine, 34:461-475, 1867, and which is incorporated herein by reference). Using this method, a first binary matrix $H_1$ was generated by replacing '−1' with '0', and then H was used to generate a second binary matrix $H_2$ by changing '−1' to '1' and '+1' to '0'. A new matrix was generated from these two matrices as $[H_1, H_2]$. Since each matrix $H_1$ and $H_2$ has a size N×N, the matrix $[H_1, H_2]$ has a size N×2N. i.e. N rows and 2N columns. The input images 130 were generated using the columns of the matrix $[H_1, H_2]$. In particular, the first input image 130 was generated using the first column of the matrix, the second input image using the second column, and so on to generate 2N input images. Each column of the matrix $[H_1, H_2]$ was converted into a square matrix of sire $\sqrt{N} \times \sqrt{N}$ (recalling that each column of $[H_1, H_2]$ has N elements. Each column of a binary matrix $[H_1, H_2]$ was displayed as a square pattern on the DMD.

An advantage of generating the input images in this way is that the input images are independent of one another, so that no input image is a linear combination of any other image. This helps to ensure that the maximum information is obtained about the transmission matrix of the MMF 118, and that there are no repeat measurements with the same input image.

As mentioned above, the output intensities may be expressed as:

$$\begin{bmatrix} I_1^1 & \cdots & I_1^p \\ \vdots & \ddots & \vdots \\ I_m^1 & \cdots & I_m^p \end{bmatrix} = ITM \cdot [H_1, H_2] \quad (12)$$

where $I_m^p$ represents the intensity value at the $m^{th}$ output pixel in the $p^{th}$ output image 134, where p=1, 2, . . . , 2N. In other words, in the matrix on the left-hand side of this equation, the intensity values for each output image are placed in a respective column of the matrix. The number p of input images 130 may be lower or higher than 2N (recalling that in an embodiment N is the number of input pixels of the DMD 108). At step S1-4, the output intensity values are stored in a multi-column output matrix (or other computer-processable equivalent), where each column of the matrix contains intensity values from one output speckle pattern.

As all micromirrors were switched 'ON' for the first input pattern, a standard Hadamard matrix [H, –H] was constructed as:

$$\begin{bmatrix} 2I_1^1 - I_1^1 & \cdots & 2I_1^p - I_1^1 \\ \vdots & \ddots & \vdots \\ 2I_m^1 - I_m^1 & \cdots & 2I_m^p - I_m^1 \end{bmatrix} = ITM \cdot [2H_1 - 1, 2H_2 - 1] = ITM \cdot [H, -H] \quad (13)$$

In this equation, the measurement matrix [$H_1$, $H_2$] has been expressed in terms of the original matrix H and the remaining terms adjusted accordingly. According to the properties of Hadamard matrices, the RVITCs $itm_{mn}$ a of the ITM 132 can be obtained by multiplying both sides of this equation by $[H, -H]^T$ (the transpose of the matrix) to yield:

$$itm_{mn} = \left(\frac{1}{2N}\right)[2I_m^1 - I_m^1, 2I_m^2 - I_m^1, \ldots, 2I_m^p - I_m^1, 2I_m^p - I_m^1, 2I_m^{2N} - I_m^1] * \quad (14)$$

$$[h_n^1, h_n^2, \ldots, h_n^p, \ldots, h_n^{2N}]^T$$

$$itm_{mn} = \left(\frac{1}{2N}\right)\sum_{p=2N}(2I_m^p - I_m^1)h_n^p$$

$$itm_{mn} = \left(\frac{1}{N}\right)\sum_{p=2N} I_m^p h_n^p$$

where $h_n^p \in (-1, +1)$ represents the values at the $n^{th}$ input pixel of the $p^{th}$ input image 130 in the Hadamard matrix [H, –H].

Thus each RVITC of the ITM 132 may be found as follows:

for a first pair, mn, of output pixel m (n=1, 2 . . . m) and input pixel n (n=1, 2, . . . N):
(a) take the first input and output image pair (p=1) and determine the product of (i) the measured output intensity or amplitude at output pixel m, ($I_m^p$), and (ii) a binary value, ($h_n^p$), indicating whether the corresponding input pixel n of the pair nm was on or off for that input and output image pair p (p=1);
(b) repeat step (a) for each input and output image pair p (p=2, 3, . . . , P);
(c) sum the products obtained in steps (a) and (b);
(d) divide said sum by the number of input pixels N and store the result as the $mn^{th}$ RVITC in the ITM 132;
repeat steps (a) to (d) for each other pair of output pixel n and input pixel n to generate m×n RVITCs and store as the ITM 132.

This process may be performed at step S1-5, and the RVITCs stored in step S1-6. It is possible to further process the RVITCs into another equivalent form or version (e.g. an inverse of the ITM 132) and to store such equivalent version instead of the ITM 132 itself.

An advantage of this is that the ITM 132 can be calculated comparatively quickly by a processor (since it involves only multiplication and addition of real-valued numbers).

It is noted that it is not essential to use binary patterns based on Hadamard matrices to generate the input images. Although Hadamard matrices provide some computational advantages (for example, the RVITCs of the ITM 132 may be obtained using the transpose of the original Hadamard matrix which is equivalent to the inverse), it may be that random binary pattern % are used as the input images for the characterization process. In that case, the Hadamard matrices. H, above would be replaced with a random binary matrix, B. and the inverse of B would be used to determine the RVITCs of the ITM 132.

Figures 1E, 3:
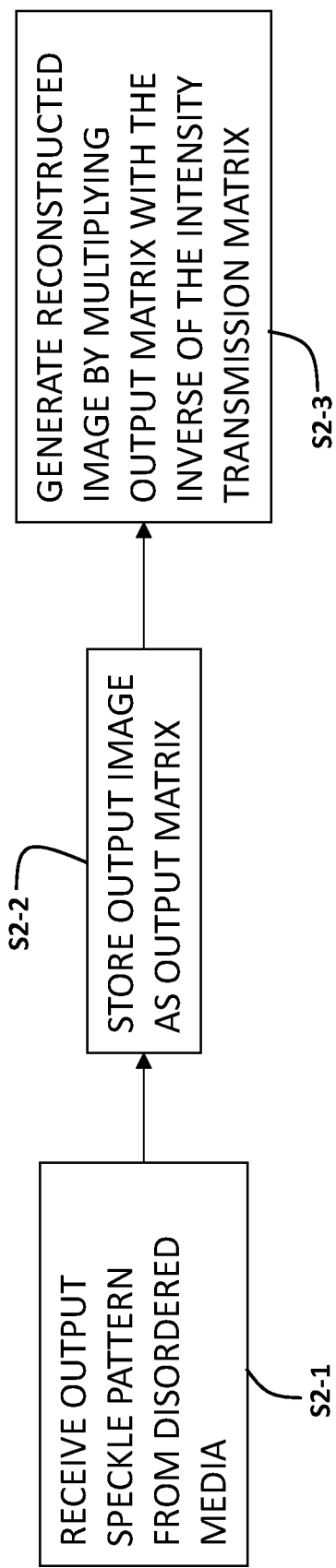
FIG. 3 is a table showing properties of different multi-mode optical fibres tested with the apparatus of FIG. 1A.

Once the ITM 132 has been generated and stored (either directly or in some other equivalent version or form), it is possible to use it to generate a reconstructed image 136 from an output speckle pattern 134. FIGS. 1C and 1E illustrate the reconstruction process. An input image 130 is transmitted by the DMD 108 into the MMF 118. At step S2-4 an output image 134 in the form of an intensity-only speckle pattern is received by the CCD camera 124. At step S2-2 the intensity values of the output image are stored in the memory 126 as an output matrix. At step S2-3 the computer processor 125 processes the intensity-only values of the output image 134 by multiplying it with an inverse of the ITM 132 to generate the reconstructed image 136. It is noted that the step of matrix multiplication may be performed using any equivalent computer-implemented operation (e.g. with a combination of linear operators) to achieve the same result.

To study the relationship between the intensities of input images 130 and output speckle patterns 134, numerical simulations were performed with a custom MATLAB program. In order to generate the output speckle patterns 134, a complex-valued transmission matrix TM with 8192 output pixels and 1024 input pixels was generated. The phases and amplitudes of the TM were randomly generated to obey uniform and Gaussian distributions between 0 and 2×, and 0 and 1, respectively. The characterization process described above was used to obtain the ITM 132. In this case the ITM 132 has m×n=8192×1024=8,388,608 elements.

To investigate the effect of the number of switched 'ON' input pixels, a series of binary images with varying J (from 32, 64, 96 . . . to 1024) were generated as input images 130. With each J, 64 different input patterns were generated by setting the values at J random pixel positions as '1' and the rest of pixels with '0'. For each J 64 reconstructed images were determined from the output intensity speckle patterns. The standard deviations of $\alpha_m$, $\beta_m$ and $\eta_m$ across all output pixels were calculated and compared when J was varied. Correlation coefficients between reconstructed images and their corresponding input images (also called 'ground truths') were calculated for the evaluation of the image reconstruction performance. The correlation coefficients were calculated as a percentage of the reconstructed pixels correctly determined. It is worth noting that the correlation coefficients for the input and output images with all the mirrors switched 'ON' were calculated by changing the value of the first pixel of the ground truth from 1 to 0.999999 so that it is not undefined.

Several physical experiments were also performed to study the impact of a variety of fibre parameters on the performance of the image reconstruction retrieval algorithm. Firstly, to study the impact of input pixel counts (N) of the input images 130, the number of input pixels on the DMD 108 used to generate each binary Hadamard pattern (used in each set 2N) was varied from 8×8, 16×16, 32×32 to 64×64, thereby producing ITMs 132 based on varying input pixel count. In other words, whilst the number of pixels in the binary pattern was kept constant (8×8), the number of illuminated micromirrors on the DMD 108 used the generate that binary pattern was varied.

After the characterisation process and the RVITCs were stored in the ITM 132, a set of random binary patterns of 8×8 size were projected onto the DMD 108 as the input images 130, or ground truths. As such, although the same set of binary patterns were used as ground truths, the input pixel count (N) of the DMD 108 varied and the reconstructed images 136 were based on different values of N. Correlation coefficients between the reconstructed images and their ground truths were calculated to evaluate the image reconstruction.

Secondly, to study the impact of the number of supported transverse modes of the MMF 118, three fibres with different core diameters and numerical apertures (NA) were tested (see table 300 in FIG. 3). Each fibre was 1 m in length. The mode count shown in the table of FIG. 3 is calculated by:

$$M_{fibre} = \frac{1}{2}\left(\frac{\pi \cdot D \cdot NA}{\lambda}\right)^2$$

where D is the diameter of fibre, NA is the numerical aperture and $\lambda$ is the wavelength of light beam 128 from laser 103.

Thirdly, to study the impact of variability of the input patterns, binary images of different types, including handwritten figures, schematic plants, animals. Chinese characters and random patterns, were used as ground truths for image reconstruction with a step-index multimode fiber (diameter 200 µm. NA=0.22, length=1 m). In addition, the reconstructed images were binarized with the Otsu threshold method, which is available in Matlab. The accuracies of reconstructed binary images, which represented the percentages of pixels with correct values, were calculated.

Finally, to study the impact of the fibre length, three step-index fibres with the same diameter (Ø200 µm) and NA (NA=0.22), but different lengths 0.1 m, 1 m and 10 m) were used for the retrieval of the same input image. After the fibre characterisation process, the input image 130 (ground truth) was displayed on the DMD 108 while output speckle patterns 134 were captured at different times. In order to evaluate the output decorrelation over time caused by fibre drift, correlation coefficients were calculated between (i) each output speckle pattern 134 and the first output speckle pattern, and (ii) between each reconstructed image 136 and the input image 130 (ground truth).

Results

Pseudo-Linearity

Figure 4B:
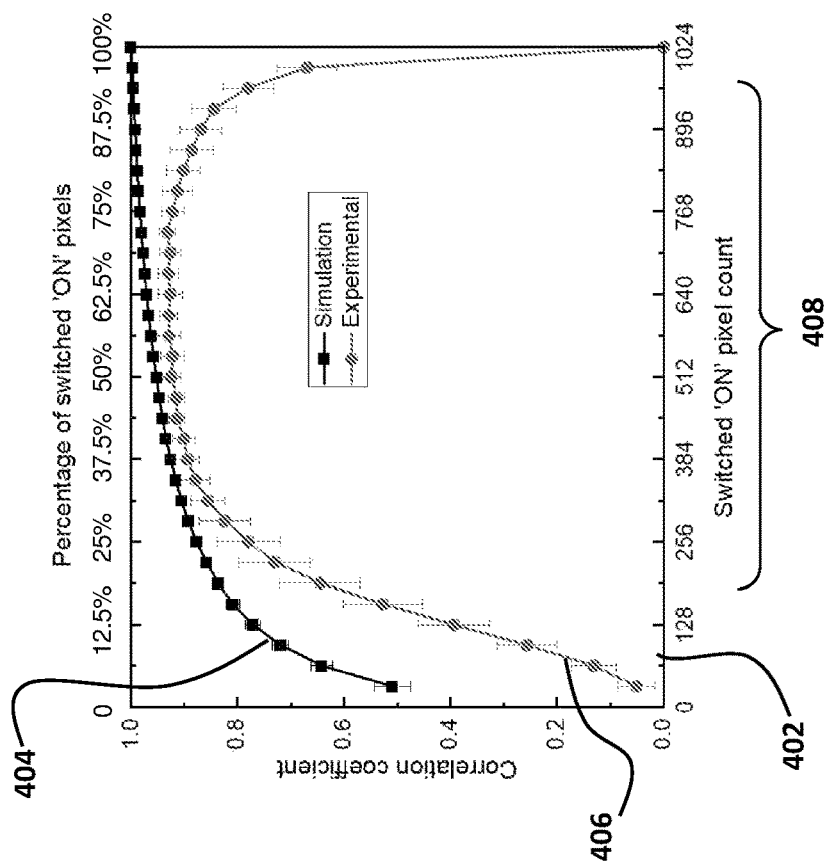
FIGS. 4A and 4B are graphs of numerical simulation and experimental results which illustrate a pseudo-linearity between input and output light intensity.
Figure 4A:
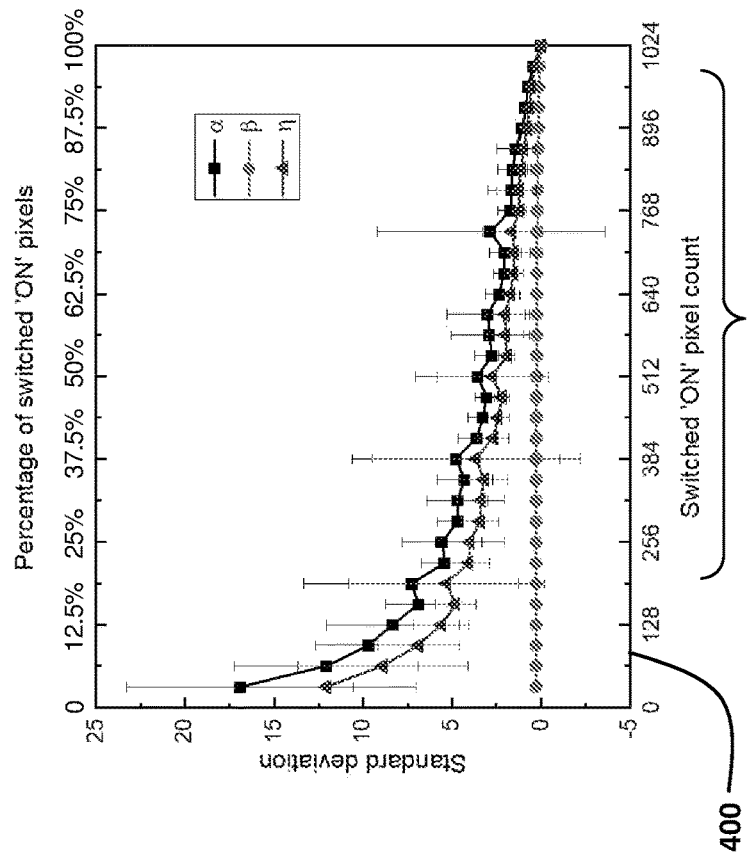

FIG. 4A is a graph 400 of the number of 'ON' input pixels J (x-axis) versus the standard deviation (y-axis) of the parameters $\alpha_m$, $\beta_m$ and $\eta_m$ as determined in the numerical simulation described above. As the number of 'ON' input pixels J increases from 32 to 1024, the standard deviations of both $\alpha_m$ and $\eta_m$ declined rapidly, while the change in the standard deviation of $\beta_m$ was much smaller. It is recalled that $\alpha_m$ is the ratio of the amplitude of the total light field when all micromirrors are 'ON' on the DMD 108 to the amplitude of the total light field when fewer than all micromirrors are 'ON', whilst $\eta_m$ is the same ratio in terms of intensity of the light field. The decline in the standard deviation of $\alpha_m$ and $\eta_m$ indicates that the amplitude and intensity of the light field at each output pixel 127a tends to a more constant value as J increases (i.e. the number of input pixels switch 'ON' increases). The standard deviation of the parameter $\beta_m$ (the ratio of the phase of the output light field to the input light field) is a much smaller value, ranging from about 0.3 when J=32 to about 0.25 when J=640. This indicates that there is a very small effect on the ratio of the output and input light fields J increases.

FIG. 4B is a graph 402 of the number of 'ON' input pixels J (x-axis) versus the correlation coefficient (y-axis) determined by comparing each reconstructed image 136 to its corresponding input image 130. As such the graph 402 indicates the performance of the image reconstruction algorithm. Two trends are shown: a first trend 404 indicating performance of the image reconstruction algorithm when performed in the numerical simulation environment, and a second trend 406 indicated the performance of the image reconstruction algorithm in the physical experiments. A correlation coefficient of 1.0 indicates that all output pixels match the input pixel values (0 or 1), whereas a correlation coefficient of 0.0 indicates that none of the output pixel values match the input pixel values.

With reference to the first trend 404 (numerical simulation) the correlation coefficients between reconstructed images 136 and their corresponding input images 130 rapidly increased from 0.5 to 0.9 as J increased from 32 to 320 and then gradually increased from 0.9 to 1 as J increased from 320 to 1024. With reference to second trend 406 (physical experiments), the correlation coefficient also increased rapidly from 0.051 to 0.89 as J increases from 32 to 384, and remained largely consistent as J increases from 384 to 896. As J increased from about 986 to about 1024, the correlation coefficient decreased rapidly from 0.85 to 0.1. This discrepancy between the simulations and measurement results may be attributed to the loss of low-spatial-frequency information in the input images 130 due to diffraction of light from the micromirror array 110 of the DMD.

Referring to both FIGS. 4A and 4B it can be seen that the ratio between the light intensity of the input image and the output speckle pattern (indicated by $\alpha_m$ and $\eta_m$) becomes roughly constant, or pseudo-linear, in region 408 when Nis greater than about 30% of the total number of input pixels. An alternative way of expressing this is that the correlation coefficient becomes roughly constant when N is greater than about 30% of the total number of input pixels. The starting point of this pseudo-linearity is not precisely defined, and could be said to start somewhere in the range 25%-40%. The starting point may also be dependent on the acceptable level of correlation coefficient. For example, some methods may need only a lower correlation coefficient compared to some other methods. e.g. in biomedical endoscopy, lower correlation coefficients can be tolerated if the user can see the necessary detail of the target in the reconstructed image.

Input Pixel Count and Number of Transverse Modes

Figure 5A:
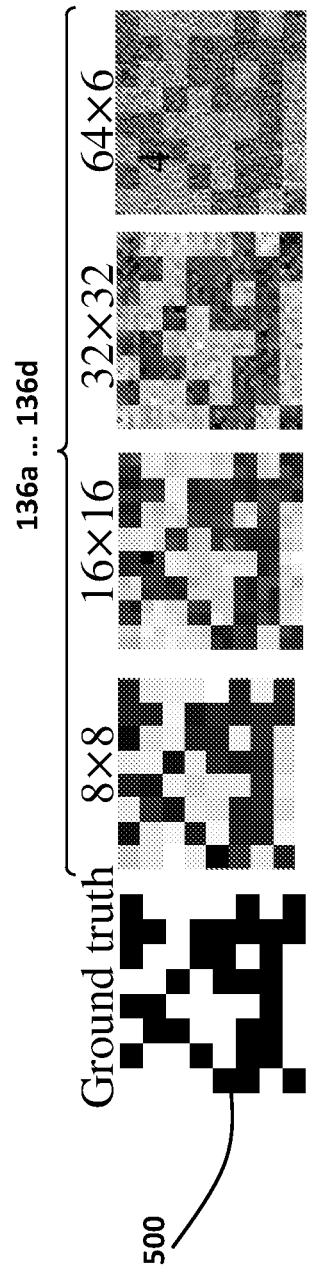
FIGS. 5A and 5B illustrate how correlation coefficient varies according to number of input pixels for the fibres shown in FIG. 3.

Turning now to the physical experiments, three different multi-mode fibres were tested. FIG. 3 shows properties of those multi-mode fibres. Each multi-mode fibre took the position of the MMF 118 in FIG. 1, and the fibre characterisation and image reconstruction methods described above were used to assess the effect of the different fibres. Prior to transmission of any input image 130, each fibre was characterised and a corresponding ITM 132 stored in memory. After characterisation of each fibre, a series of input images were transmitted into the fibre and received as output speckle patterns 134 at the CCD camera 124. FIG. 5A illustrates the binary pattern 500 that was passed through each a fibre. However, it is noted that the number of pixels (on the micromirror array 11 of the DMD 108) making up the binary pattern 500 was 8×8, 16×16, 32×32 and 64×64. Thus a series of four input images was transmitted, with each input image constructed with a different number of input pixels on the DMD 108.

Once each output speckle pattern was received by the CCD 126, a corresponding reconstructed image was generated from each output speckle pattern. An example of the reconstructed images is shown in FIG. 5A: reconstructed images 136a-136d were generated from the output speckle patterns 134 received at the CCD camera 124 from the fibre called "Fiber-200-0.22" in FIG. 3.

Figure 5B:
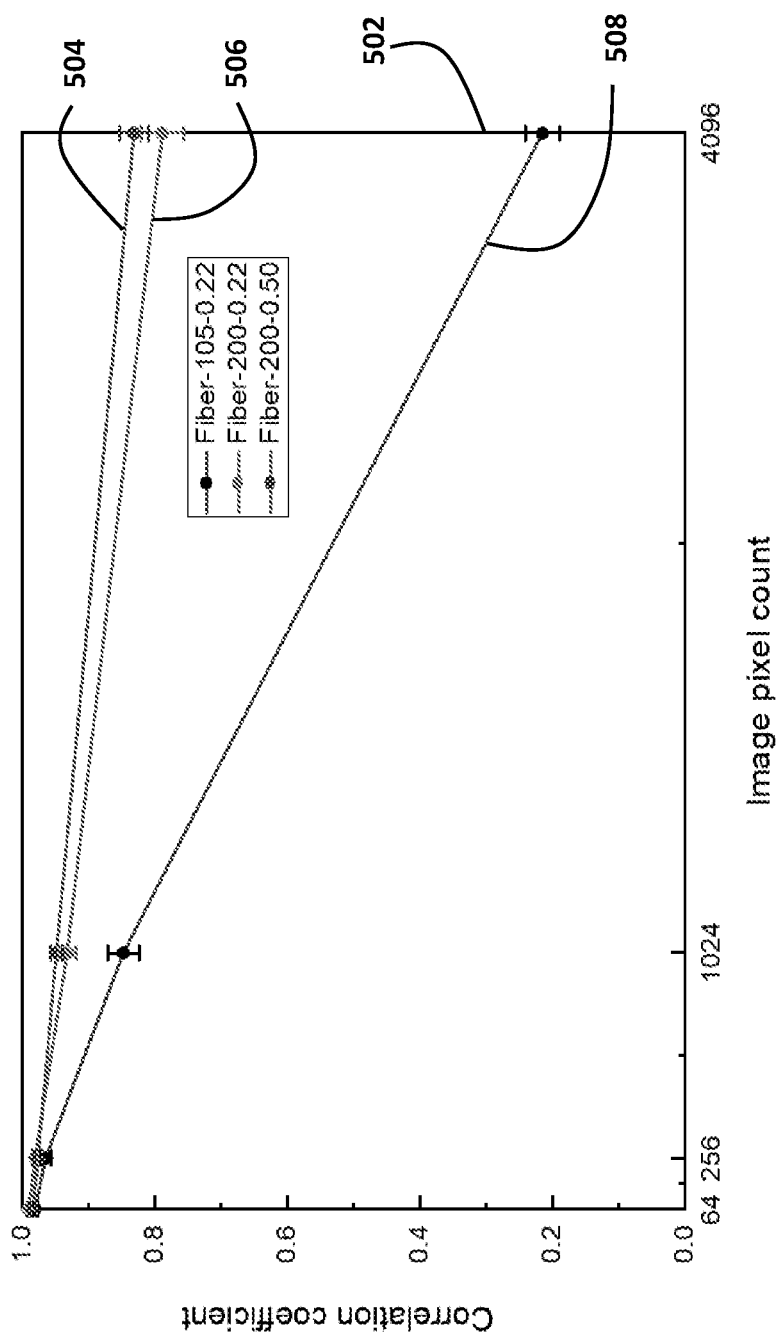

FIG. 5B is a graph 502 of the number of input pixels used to form the binary input pattern 500 (x-axis) versus the correlation coefficient between the input image 130 and the reconstructed image 136. It is noted that the number of input pixels in FIG. 5B is the total number of input pixels (e.g. 8×8, 16×16, etc.) used on the DMD 108 to transmit the binary input pattern 500, and is not the same as the number of 'ON' pixels, J, mentioned above. First trend 504 indicates the results for the "Fiber-200-0.50", second trend 506 indicates the results for the "Fiber-200-0.22", and third trend 508 indicates the results for the "Fiber-105-0.22". It can be seen that as the number of input pixels increases, the quality of the reconstructed image (defined by the correlation coefficients) decreased. For example, second trend 506 shows that the correlation coefficient declined from 99.44% to 76.81% as input pixel count increased from 8×8 to 64×64.

The core diameter and NA of each MMF had significant impact on the quality of the reconstructed image. This can be explained by the varying number of supported transverse modes in the fibres (see FIG. 3). The fibres with larger numbers of supported transverse modes (Fiber-200-0.22. Fiber-200-0.50) were able to transmit images with higher input pixel counts.

The computation time for the characterisation process (in order to estimate the RVITCs of the ITM 132) increased with the increase of both the input and output pixel counts (N and M). For example, with a desktop PC (Intel i7 8700, 3.2 GHz, 16 GB RAM), when N and M increased from 32×32 and 360×360 to 64×64 and 500×500, respectively, the computation time for ITM estimation increased from ~8 s and ~240 s, respectively.

Variability of Binary Input Patterns

The apparatus of FIG. 1 was also used to investigate the impact of changes to the binary input pattern used to generate the input image 130. In this part of the experiment the MMF 118 was the optical fibre "Fiber-200-0.22" (see FIG. 3). The characterisation process was used to generate and store an ITM 132 for the optical fibre.

Figure 6A:
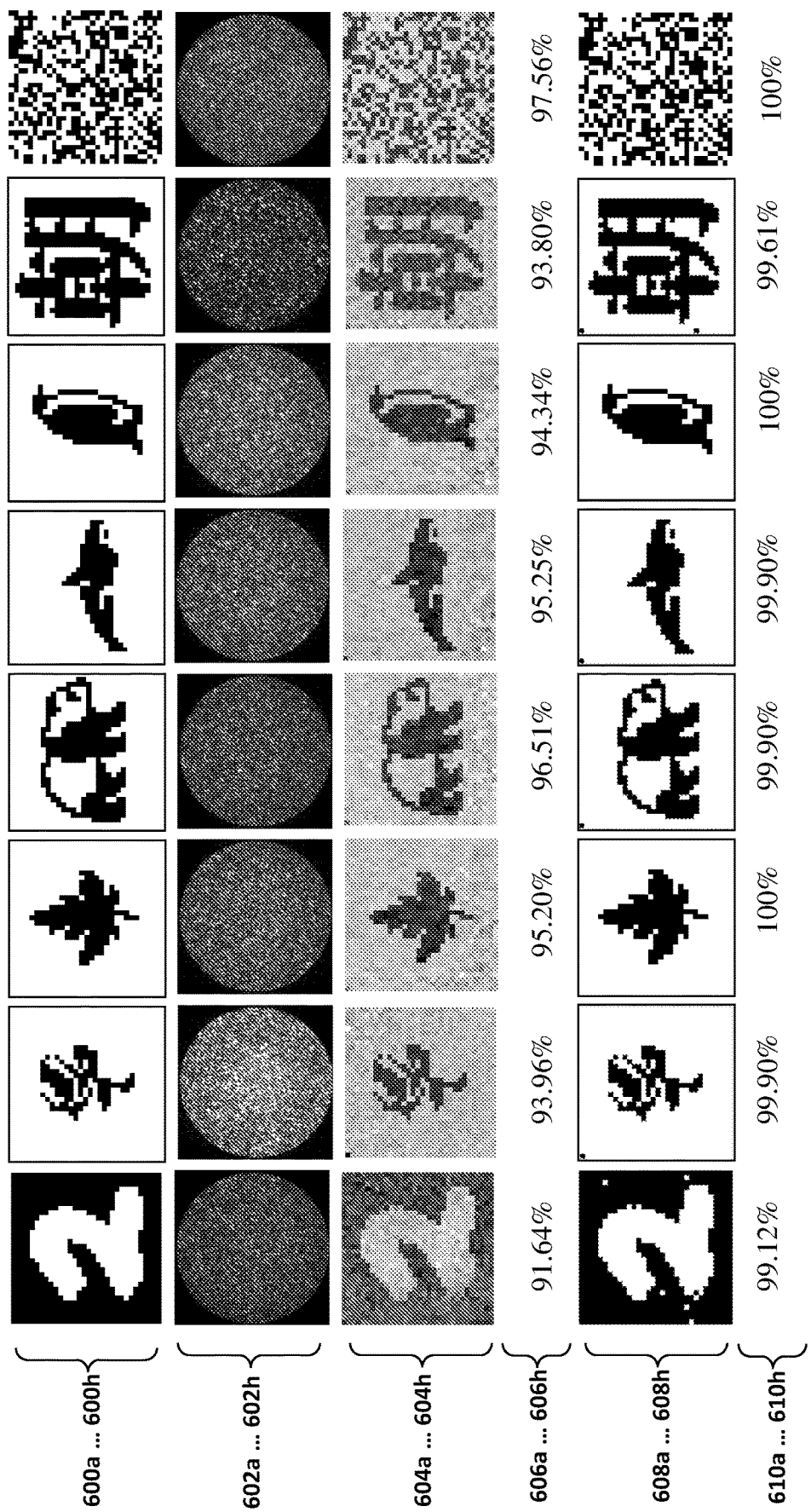
FIG. 6A shows various input and output images, speckle patterns, reconstructed images and binary reconstructed images obtained using the apparatus of FIG. 1.

After the characterisation process was completed, a series of input images were transmitted through the MMF 118. FIG. 6A shows different input images 600a-600h (also called ground truths) that were generated using 32×32 input pixels of the DMD 108. Each input image 600a-600h was transmitted into the multi-mode fibre and corresponding output speckle patterns 602a-602h were received at the CCD camera 124. The image reconstruction process was used to generated reconstructed images 604a-604h from the output speckle patterns. Correlation coefficients 606a-606h were calculated for each pair of input image 600a-600h and reconstructed image 604a-604h. Finally, the reconstructed images 604a-604h were binarized to generate binary output images 608a-608h.

The quality of the reconstructed images 604a-604h was weakly dependent on the binary input patterns in the input images 600a-600h. In particular the correlation coefficients between the reconstructed images 604a-604h and the input images 600a-600h varied from 91.64% for a handwritten digit (600a/604a) to 97.56% for a random binary pattern (600h/604h). A further experiment was performed with the same set up, except that a higher number of input pixels (64×64) was used on the DMD 108 for each input image 600a-600h. In that case the correlation coefficient varied from 76.22% for the handwritten digit (600a/604a) to 90.43% for the random binary pattern (600h/604h), respectively.

The accuracy 610a-610h of the binary output images 608a-608h demonstrates that there is a weak dependency on quality of the reconstructed images 604a-604h (as defined by the correlation coefficient 606a-606h). In particular, the accuracy 610a-610h of each binary output image 608a-608h was almost 100% irrespective of the correlation coefficient. This indicates that the apparatus and methods described herein would be especially useful for transmission and reception of binary data across a disordered medium, such as a multi-mode optical fibre.

Figure 6B:
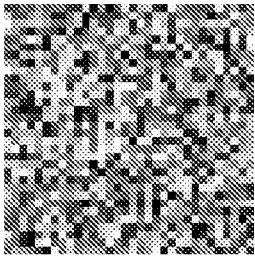
FIG. 6B shows various grayscale images, speckle patterns, reconstructed images obtained using numerical simulations.

FIG. 6B shows the results of a further numerical simulation (similar to that reported with reference to FIG. 4B) to investigate whether the methods described herein can be used to reconstruct grayscale input images, rather than binary input images. The input images had 32×32 input pixels and each pixel was randomly assigned a value between 0 and 255. As can be seen, grayscale input images may be reconstructed with an accuracy of greater than 98%. This demonstrates the plausibility of the methods described herein for transmitting grayscale input images.

Fibre Length

The apparatus of FIG. 1 was used to investigate the effect of optical fibres of different lengths. Three MMFs 118 of length 0.1 m, 1.0 m and 10 m were investigated. Each MMF 118 had a diameter 200 μm and numerical aperture 0.22. Prior to transmission of an input image through each MMF 118, the characterisation process was used to generate and store an ITM 132 for that optical fibre.

Figure 7B:
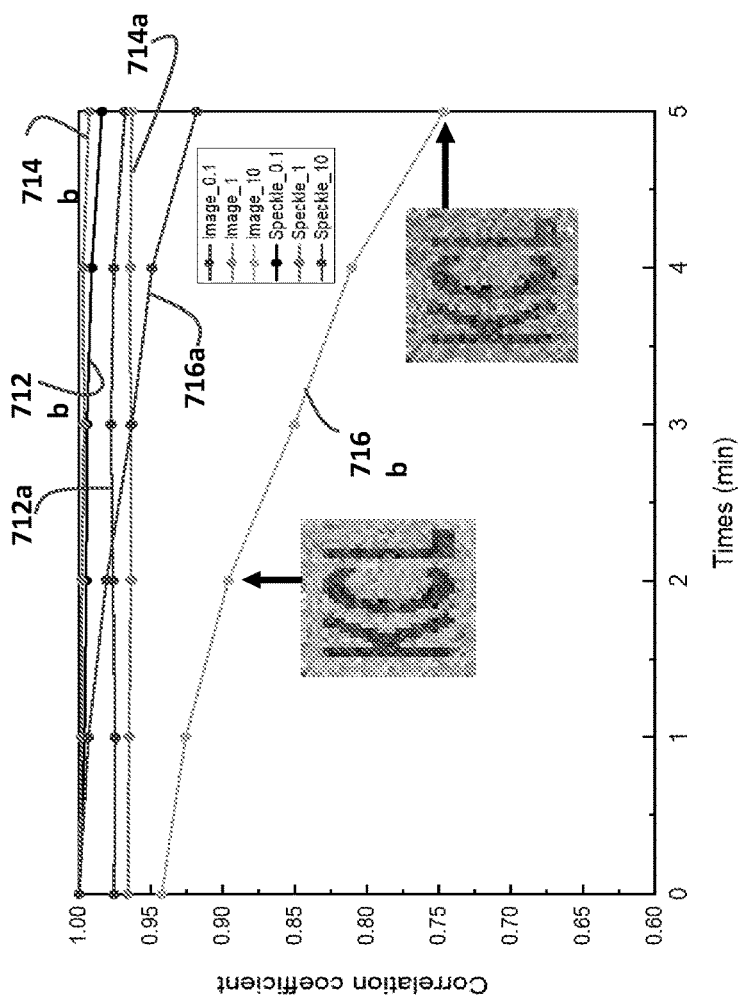
FIGS. 7A and 7B are diagrams indicating how the correlation coefficient changed with time for the fibres shown in FIG. 3.
Figure 7A:
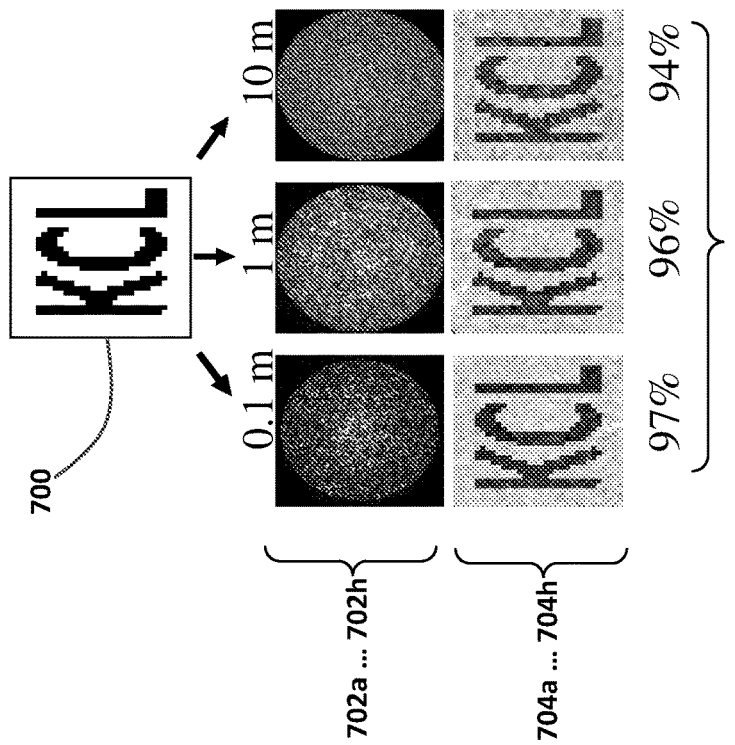

Referring to FIG. 7A the input image 700 was a binary pattern of the letters 'KCL'. 32×32 input pixels of the DMD 108 were used to transmit the input image into the MMF 118. The CCD camera 124 received output speckle patterns 702a, 702b and 702c corresponding to the 0.1 m, 1.0 m and 10 m MMFs 118 respectively. Reconstructed images 704a, 704b, 704c were determined for each input image 700 and correlation coefficients 706a, 706b, 706c were determined between each reconstructed image and the input image. As shown in FIG. 7A, all MMFs 118 produced high correlation coefficients of 97%, 96% and 94%, respectively. These results suggest that the characterisation and image reconstructions processes are insensitive to fibre length.

However, it was found that the 10 m fibre suffered from fibre drift (causing decorrelation of the output speckle patterns). Referring to FIG. 7B a graph 710 of time (x-axis) versus correlation coefficient (y-axis). In this particular part of the experiment, the correlation coefficient of both the output speckle pattern and the reconstructed image (each compared to the input image) was monitored over time. First trends 712a and 712b show the change in correlation coefficient of the reconstructed image and output speckle pattern using the 0.1 m fibre. Second trends 714a and 714b show the change in correlation coefficient of the reconstructed image and output speckle pattern using the 1.0 m fibre. Third trends 716a and 716b show the change in correlation coefficient of the reconstructed image and output speckle pattern using the 10 m fibre.

The first trends 712b and second trends 714b show that the correlation coefficients of the output speckle patterns using the 0.1, m and 1.0 m length fibres remained relatively stable (~99%) over a 5-minute period. Accordingly the first trends 712a and 714a of the correlation coefficient of the reconstructed images also remained at a stable level (~97% and ~96% respectively). However, for the 10 m fibre, the output speckle pattern captured 5 minutes after fibre characterization process had degraded from 100% to ~92%, whilst the correlation coefficient of image retrieval degraded from ~94% to ~75%. The faster degradation of the output speckle pattern from the 10 m fibre was mainly caused by two factors: first, the longer length suffered more serious fibre drift; and second, both 0.1 and 1.0 m fibres were in cable suits and fixed on an optical table, whilst the 10 m fibre was twined on a mount and hence suffered more vibration.

Figure 8:
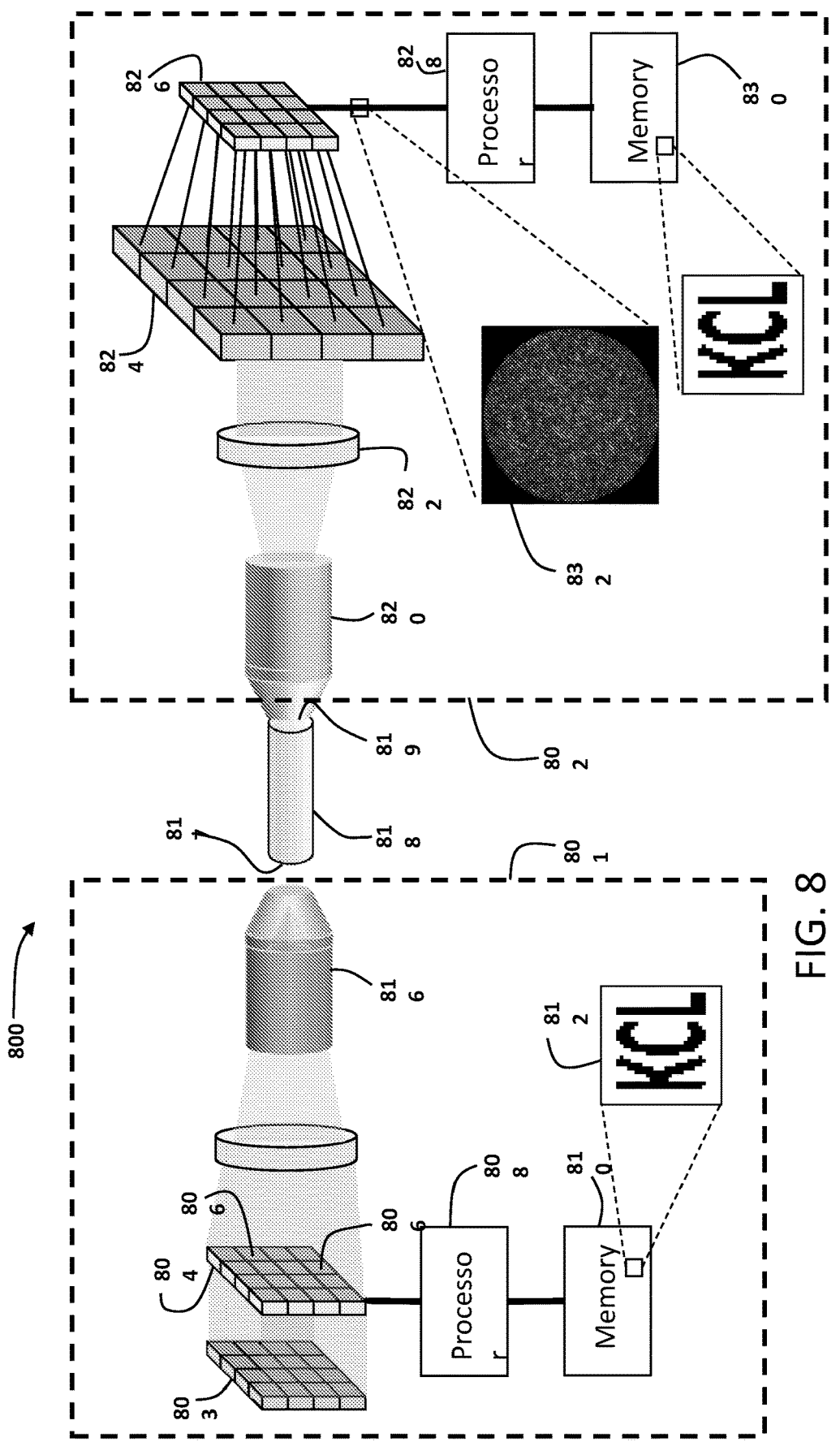
FIG. 8 is a schematic diagram of another apparatus according to an embodiment of the present invention.

Referring to FIG. 8 an apparatus for transmission and reception of an image through a disordered medium is generally identified by reference numeral 800. The apparatus may comprise a transmitter 801 and a receiver.

The image may represent a binary sequence of data (such as a digital bit stream or byte stream for example) and the apparatus may be adapted to transmit a plurality of different images over time whereby the apparatus is useful for parallel communication; that is to say two or more binary digits bits of data may be transmitted simultaneously in each image. The image transmission may take place through a disordered medium such as an optical fibre, and may be through a multi-mode optical fibre.

The transmitter 801 may comprise a plurality of controllable electromagnetic radiation sources. In an embodiment the plurality of controllable electromagnetic radiation sources may comprise a light transmitter array unit 803 optically coupled with a light modulator array unit 804. The light transmitter array unit 803 may comprise a plurality of coherent light sources that are optically coupled via respective a bundle of optical fibres (not shown) to the light modulator array unit 803. These coherent light sources may be laser diodes, or solid-state lasers. The light transmitter array unit 803 may be a 2D array of vertical-cavity surface-emitting lasers (VCSEL).

The light modulator array unit 804 comprises a plurality of input pixels 806. In an embodiment the light modulator array unit 804 may be a spatial light modulator. In an embodiment the light modulator array unit 804 may be an array of electrical circuits that modulate the current or voltage supply for driving the light transmitter array unit 803. In another embodiment the spatial light modulator may be a deformable mirror. Each input pixel 806 is controllable to either transmit or not transmit a portion of the light received from the light transmitter array unit 803. In this way the light modulator array unit 804 may indicate a binary pattern on its output side. For example a binary '1' may be indicated by light being allowed to pass through an input pixel 806, and a binary '0' may be indicated by light not be allowed to pass through an input pixel 806, or vice-versa. The control of each input pixel is performed by a first computer processor 808 in conjunction with a first memory 810 (such as RAM and/or non-volatile memory). The first computer processor 808 and first memory 810 may be in the form of an ASIC, system-on-a-chip or photonic-integrated circuit.

The computer processor 808 and memory 810 are adapted to cause a binary input pattern 812 to be displayed on the output side of the light modulator array unit 806. The binary input pattern 812 shown in FIG. 8 is merely exemplary. The binary input pattern 812 may also be a pattern indicating a sequence of binary data.

Light from the light modulator array unit 804 passes to a first lens 814 that focuses the light to the input of a first objective lens 816. The first objective lens 816 focuses the light onto the proximal end 817 of an optically disordered medium 818. The optically disordered medium 818 may be a multi-mode optical fibre, such as a step-index multi-mode optical fibre. The light passes through the optically disordered medium 818 and out of a distal end 819. The light is scattered as it passes through the optically disordered medium 818.

The light passes through a second objective lens 820 that collimates the light leaving the optically disordered medium 818. A second lens 822 may further collimate the light before it arrives at a plurality of electromagnetic radiation detectors. In this embodiment a plurality of electromagnetic radiation detectors may be a light detector array unit 824. The light detector array unit 824 may be a focal plane array. The light detector unit may be an array of optical fibres arranged such that light is collected at the ends of the fibres nearest the second lens 822 and is delivered to a photodetector, such as a photodiode. The light detector array unit 824 may comprise a plurality of output pixels 825. Each output pixel may be a photodetector, such as a photodiode. The light detector array unit 824 may be an avalanche photodiode (APD) array, such as an 8×4 Si APD array available from Hamamatsu (product code S8550-02). An analogue-to-digital converter (ADC array unit 826 for readout of output signals from the output pixels 825. The ADC array unit may also digitize the output signals and make the digitized signals available to a second computer processor 828. The computer processor 828 may store the digitized signals in a second memory 830. The digitized output signals represent an output speckle pattern 832 received at the light detector array unit 824 resulting from the scattering of the light as it passes through the optically disordered medium 818. The second computer processor 828 and second memory 830 may be in the form of an ASIC, system-on-a-chip or photonic-integrated circuit.

In order to implement the characterisation process to obtain image intensity constants of the ITM for the optically disordered medium 818, the first memory 818 may stow computer executable instructions for implementing the input image transmission steps of the characterisation process steps described above in conjunction with FIG. 1D. In particular steps S1-1 and S1-2 may be stored as computer executable instructions in the controller 129. Furthermore, the second computer processor 828 and second memory 830 may store computer executable instructions for implementing the receiver steps of the characterisation process described with reference to FIG. 1D. In particular, steps S1-3, S1-4, S1-S and S1-6 be stored in the memory 126 and executed by the processor 125.

In order that the second computer processor 828 may determine the image intensity constants, the second memory 830 may have stored the set of input images transmitted under control of the first computer processor 808. The set of input images may be transferred from the first memory 810 to the second memory 830 by a separate transmission method (not shown), such as use of the Internet, at some point during the characterisation process or beforehand.

Once the image intensity constants have been determined for the optically disordered medium 818, these may be stored by the second processor 828 in the second memory 830, and the apparatus 800 may be used for parallel communication of binary data. In order to implement the image reconstruction process described above in conjunction with FIG. 1E, the second memory 830 may store computer-executable instructions for implementing the steps of the reconstruction process.

The first computer processor 808 and first computer memory 810 may be adapted to transmit a sequence of input images representing binary data. For example, each input image may comprise a 2×2, 4×4, 8×8, etc. image of binary data using the light modulator array unit 814. The second computer processor 828 and second memory 830 may receive each output speckle pattern corresponding to the input image and use the image reconstruction process to recover a reconstructed image. The reconstructed image may be binarized to recover the binary data of the input image.

In some embodiments, input images may be displayed by the light modulator array unit 804 at a rate of 22,000 frames per second. However, higher or lower speeds are envisaged. The light detector array unit 824 may be able to capture the output images at a rate of 250 frames per second. However, higher or lower speeds are envisaged. The display and detection rates may be matched.

It may be desirable to repeat the characterisation process from time-to-time. In this way a new set of RVITCs (or any computer-processable equivalent) is generated and stored by the second memory 830 for use in the next image reconstruction process. The repetition of the characterisation process may take place periodically (for example every 30 mins, although other time periods are envisaged which may be dependent on the length of the fibre—a longer fibre may require more frequent characterisation), or as often as necessary desired. It may be that known input images are transmitted at certain time intervals or every nth input image. In this way the second computer processor 828 and second memory 830 may check reconstructed images remain accurate (for example with a correlation coefficient above a certain threshold, e.g. 99%). If the accuracy has degraded, the characterisation process may be triggered.

Figure 9:
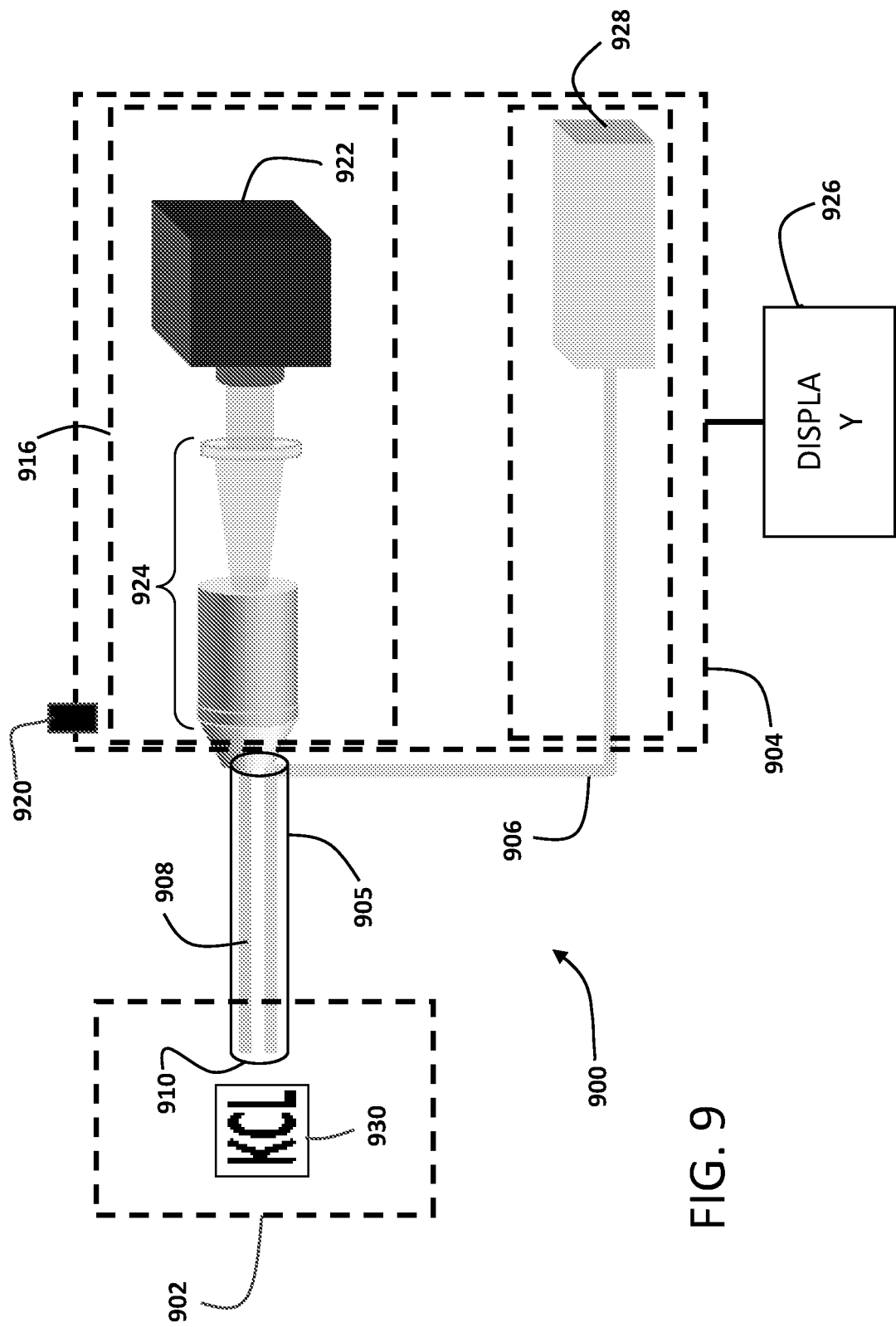
FIG. 9 is a schematic diagram of another apparatus according to an embodiment of the present invention.

Referring to FIG. 9 an apparatus for obtaining an image inside a body is generally identified by reference numeral 900. The apparatus 900 comprises an endoscope 902 and a control console 904. The endoscope 902 comprises a tube 905. The tube 905 may be substantially rigid or substantially flexible. The tube 905 contains a single-mode optical fibre 906 and multi-mode optical fibre 908, both of which terminate at a distal end 910 of the tube 904. The endoscope 902 may comprise a grip (not shown) via which an operator may support the weight of the endoscope and assist its entry into a body 912. The fibres 906 and 908 extend from a proximal end 914 of the tube 905 and into the control console 904. Mounted inside the control console 904 is a transmitter 914, a receiver 916 and an illuminator 918. The transmitter 914 is similar to the transmitter part of the apparatus 800 described above. That is the transmitter 914 comprises a laser, spatial light modulator, and a computer processor and memory (not shown in FIG. 9) for controlling the spatial light modulator to display known input images. However, in this embodiment the transmitter 914 is used only for the characterisation process. In particular, the control console 904 comprises a port 920 for receiving the distal end 910 of the tube 905. When the distal end 905 is connected to the port 920, the end of the fibre 908 is brought to a position where it may receive input light from the transmitter 914 as will be described in greater detail below.

The receiver 916 is similar to the receiver part of the apparatus 800 described above. That is the receiver comprises a light detector array unit 922, and optics 924 for receiving a computer processor and memory for processing received light intensity data and reconstructing images using the image reconstruction process. The control console 904 may be connected for a display 926 so that reconstructed images may be displayed to a used as the endoscope 902 is in use.

The illuminator comprises a laser 928 arranged to transmit light into the fibre 906. In use, light travels along the fibre 906 and leaves the distal end 910 of the tube 905 to illuminate inside the body 921.

Before the endoscope 902 can be used to view an internal part of the body 912, the multi-mode optic fibre 908 may be characterised in order to determine and store an ITM containing the RVITCs. To do that, the distal end 910 of the tube 905 is inserted into the port 920. That brings the end of the fibre 908 into alignment with the transmitter 914. Once in place, the characterisation process can be performed on the fibre 908 and the RVITCs stored by the receiver 916.

It is noted that, since the transmitter 914 and receiver 916 are in the same location (in the control console 904), they may share computing resources. For example, the transmitter 914 and receive 916 may share one or more computer processors. In another embodiment, the transmitter 914 and 916 may have dedicated computing resources. For example, the transmitter 914 and receiver 916 may have one or more dedicated computer processor (e.g. in the form of an ASIC or ASIP).

After the characterisation process is completed, the endoscope 902 is ready for use. If the endoscope is being used to look inside a patient (e.g. inside the human or animal body), the distal end 910 of the endoscope 902 is inserted through an opening or cavity in the body. Light from the laser 912 illuminates an interior portion of the body, for example an imaging target 930. Light is scattered and reflected by the imaging target 930 and a portion of the light is received by the end of the multi-mode fibre 908 at the distal end 910. This light is an input image into the multi-mode fibre 908, in a similar way to input images generated by the digital micromirror device described in embodiments above.

The input image is scattered inside the fibre 909 as it travels toward the receiver 916. At the receiver 916 the input image has become an output speckle pattern, as described above. The receiver 916 may take samples of output speckle pattern (e.g. at a certain number of frames per second), and may use the image reconstruction process described above to generated a reconstructed image for each sample of the output speckle pattern. The number of frames per second may be high enough so that a video may be displayed on the display 926.

Focusing Light at a Target Via a Disordered Medium

Figure 10:
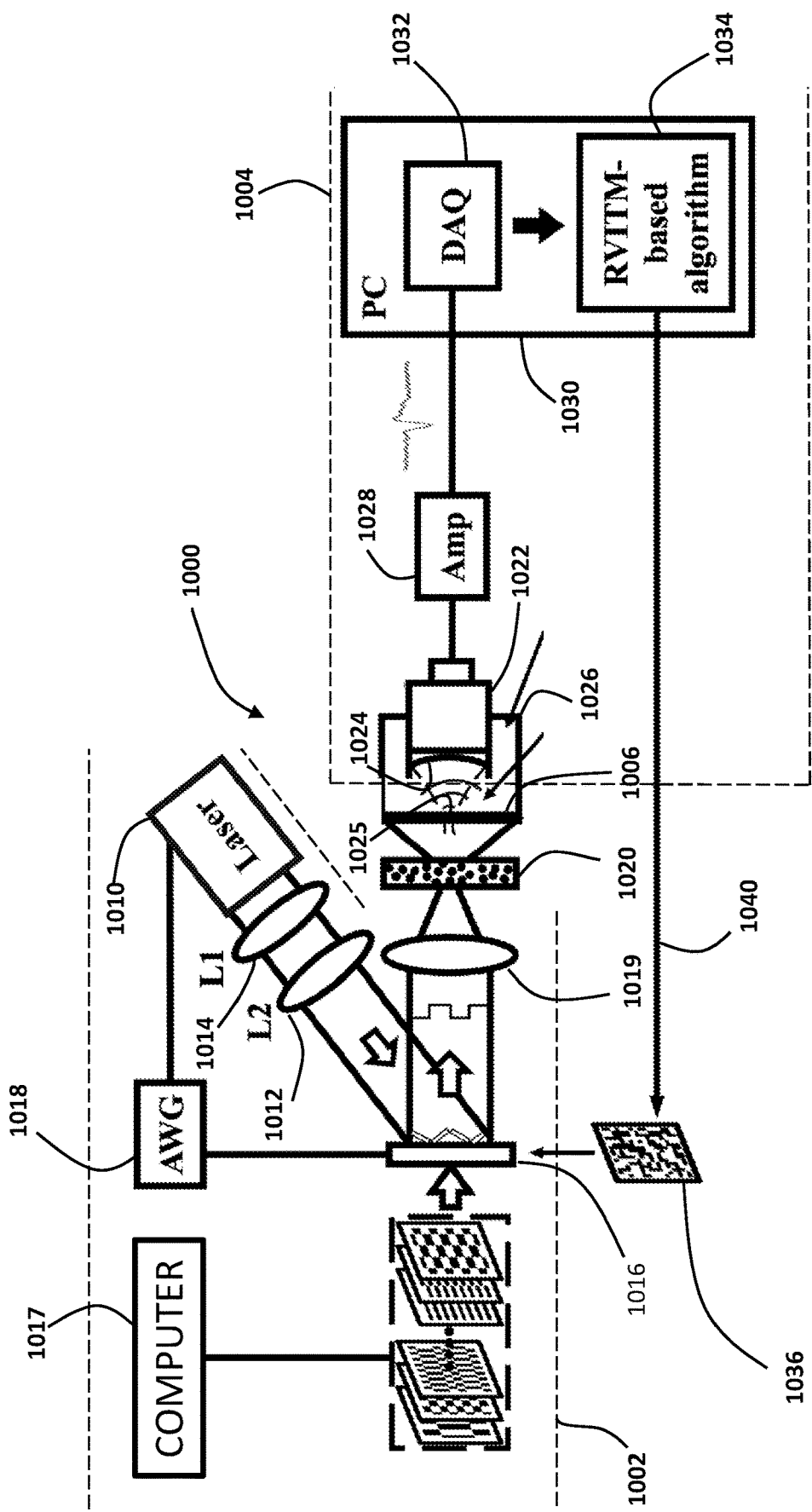
FIG. 10 is a schematic diagram of an apparatus according to an embodiment of the present invention.

Referring to FIG. 10 an apparatus for focusing electromagnetic radiation (e.g. laser light) at a target via a disordered medium is generally identified by reference numeral 1000. As used herein the phrase "focusing light at a target via a disordered medium" is intended to include a number of different scenarios including, but not limited to: (a) light transmitted from a first side to a second side of the disordered medium with focusing taking place beyond the second side; (b) light transmitted into the first side, scattered inside the disordered medium and then focused inside the disordered medium; and (c) light transmitted toward the first side, diffusely reflected from the first side, and then focused after that diffuse reflection. In all cases, including (a), (b) and (c), the focusing is achieved by controlling transmission of the light before it enters or is reflected from the disordered medium.

The electromagnetic radiation may be collimated, substantially spatially and temporally coherent light (e.g. laser light). The electromagnetic radiation may be at optical wavelengths, for example between about 100 nm and about 1000 nm. The electromagnetic radiation used by the apparatus 1000 may be pulsed or may be intensity-modulated continuous wave.

The disordered medium may be any disordered medium as described anywhere in this document. Examples of such disordered media include, but are not limited to, in vitro and in vivo biological tissue belonging to a human or other animal, an optical waveguide such as a multi-mode optical fibre, a surface from which optical light is reflected such as a wall, floor or ceiling in a building, and any aerosol such as fog, mist or dust.

The apparatus 1000 comprises a transmitter 1002 and a receiver 1004. The transmitter may be adapted for inputting, or projecting, collimated and spatially and temporally coherent electromagnetic radiation at optical wavelengths into an optical system and may be adapted to cause the light to be focused onto a target 1006 even though it passes via a disordered medium 1008 before reaching the target. As such the transmitter 1002 may comprise a plurality of electromagnetic radiation sources. The receiver 1004 may be adapted for receiving a direct or indirect indication of the intensity of electromagnetic radiation at the target. In one embodiment the receiver 1004 receives an indirect indication in the form of ultrasound waves generated by the photoacoustic effect, generates signals representing those ultrasound waves and then processes those signals, as described in greater detail below.

The transmitter 1002 may comprise a laser 1010. The laser 1010 may be an actively Q switched diode pumped solid state laser such as the SPOT-10-200-532 laser available from Elforlight. The SPOT-10-200-532 is adapted to produce a collimated beam of spatially coherent light at 532 nm with a minimum pulse width of <1.8 ns and a maximum pulse energy of 10 μJ (at ≤10 kHz). The spatial mode of the laser is $TEM_{00}$, with a beam diameter ~1 mm.

The laser 1010 is positioned so that, in use, the beam may be directed onto an achromatic doublet comprising a first convex lens 1012 (f=30 mm) and a second convex lens 1014 (f=50 mm). In an embodiment the achromatic doublet may be model AC254-030-A-ML available from Thorlabs, Inc. Similarly to the apparatus 100, the apparatus 1000 comprises a digital micromirror device (DMD) 1016. The DMD 1016 is identical to the DMD 108 and all details of the DMD 108 described above are incorporated into this embodiment. The purpose of the achromatic doublet is to expand the beam diameter to cover the DMD 1016. A first computer 1017 may be provided for generating and storing DMD patterns, and for sending those DMD patterns and instructions to the DMD 1016.

The transmitter 1002 may comprise a synchronization device 1018 for synchronizing intensity variation (e.g. as individual pulses, or as intensity modulation of a continuous wave) of the laser beam with the operation of the DMD 1016 as described in greater detail below. In this embodiment the synchronization device 1018 is an arbitrary waveform generator ('AWG') such as a model 33600A available from Keysight Technologies, Inc.

The transmitter 1002 may comprise a third convex lens 1019 (f=30 mm, AC254-030-A-ML available from Thorlabs) positioned to received spatially modulated light from the DMD 1016 and to direct that light onto a diffuser 1020. The diffuser 1020 may be a ground glass diffuser such as model N-BK7 with a 220-grit polish available from Thorlabs. The purpose of the diffuser 1020 is to act as a disordered medium and provide an effect on the spatially modulated light similar to scattering by biological tissue for example, or diffuse reflection from a surface such as a wall, floor or ceiling.

The target 1006 may be placed about 5 mm behind the diffuser 1020 to receive light that has passed through it. The target 1006 acts as an optical absorber and may be a piece of black insulation tape, although any other material that is capable of absorbing laser light and generating ultrasound can be used. These materials include absorbing tissue chromophors including, but not limited to, haemoglobin, myoglobin, melanin, bile, collagen, deoxyribonucleic acid, ribonucleic acid, lipid and water. The purpose of the target is to absorb at least a portion of the incident light from the diffuser 1020 so that it may be detected by a detector 1022. The detector 1022 may be an ultrasonic transducer such as a flat single-element piezoelectric ultrasonic transducer. In the present embodiment, the ultrasonic transducer is model V358 from Olympus, which has a central frequency of 50 MHz and a diameter of 6.4 mm (0.25 inches). A focusing element 1024 may be provided in the ultrasonic detector to provide a receiver focus 1025. In one embodiment the focusing element 1024 may be silica piano-concave lens attached on the active surface of the ultrasonic transducer, such as model LC4210 from Thorlabs which has a focal length of −25 mm. Both the target 1006 and the detector 1022 were immersed in a water bath 1026 to provide acoustic coupling between them. The distance between the detector 1022 and the target 1006 was adjusted to maximise received ultrasound signals so that the target was situated at the receiver focus 1025 of the detector 1022. In use, the detector 1022 receives ultrasound signals from the target 1006 and provides an output electrical signal representing the detected ultrasound.

An amplifier 1028 may be provided to receive and amplify the electrical signal from the ultrasonic detector. The amplifier may be a model SPA.1411 available from Spectrum Instrumentation. A second computer 1030 (e.g. a personal computer having a processor such as an Intel® i7, 3.2 GHz) may be connected to the amplifier 1028 to receive an amplified electrical signal from the amplifier 1028. The computer 1030 may have a Data Acquisition (DAQ) card 1032, such as model Mi.4420 available from Spectrum Instrumentation, to digitise the amplified electrical signal. The computer 1030 may also comprise a computer memory 1034 for storing digitised ultrasonic data generated by the DAQ 1032. It is noted that in other embodiments the first computer 1017 and the second computer 1030 may take different forms, such as ASIC, ASIP and system on a chip, etc.

The computer memory 1034 also stores a set of computer-executable instructions that, when executed, perform steps to determine a set of real-valued intensity transmission constant ('RVITCs') for the diffuser 1020. The steps are described in greater detail below. However, the purpose of the steps is to characterise the diffuser 1020 and determine and store a focusing spatial modulation pattern 1036 that will achieve an improved focus of the light through the diffuser 1020 onto the target 1006. Once the focusing spatial modulation pattern 1036 has been determined, the second computer 1030 may communicate it to the first computer 1017 for storage by the first computer 1017 and subsequent use. The communication between the second computer 1030 and the first computer 1017 may take place using a data communication system 1040 (shown schematically by an arrow in FIG. 10). The data communication system is not a part of the apparatus 1000, although the transmitter 1002 and receiver 1004 may have one or more interface (not shown) respectively for sending and receiving data over the data communication system 1040. The data communication system may take a number of forms, including by not limited to, wireless systems (e.g. WiFi. Bluetooth, cellular) and wired systems (e.g. Ethernet, power-line), or any combination of these.

In certain aspects, to provide a visual evaluation of the focusing, the target 1006 and detector 1022 were replaced with a CCD camera provided with a convex lens (e.g.

AC254-050-A-ML from Thorlabs) for capturing the output speckle patterns at the focus of the ultrasound transducer.

Operation

In use, light is generated by the laser 1010, spatially modulated by the DMD 1016 and transmitted to the diffuser 1020. The light is scattered by the diffuser 1020 and portion is transmitted toward the target 1006. At least some of the energy of the light which reaches the target 1006 is converted via the photoacoustic effect into ultrasound that is detected by the detector 1022.

A difference between the operation of the apparatus 1000 and operation of the apparatus 100 is that during use of the apparatus 100 there are P output images, with each output image p comprising in output pixels and each pixel representing an intensity value. For each input DMD pattern k there are thus m output intensity values. However, during operation of the apparatus 1000 each output p is a single ultrasonic intensity signal taken by the detector 1022. Since the detector 1022 is arranged to measure intensity of ultrasound at the receiver focus 1025 on the target 1006, each ultrasonic intensity signal represents the degree to which light reaching the target 1006 is focused at the focal point: a higher valued measurement indicates better focus, whereas a lower valued measurement indicates that the light leaving the diffuser 1020 is dispersed over a wider area of the target 1006. In this way it is possible to use the receiver focus 1025 of the detector 1022 as a guide to focus light onto the target 1006.

It is possible for the second computer 1030 to determine the ultrasonic signal intensity by any number of techniques. For example within a given period of time: as the difference between maximum and minimum measured values; as the maximum measured value; as the absolute value of the minimum measured value; integration of the absolute value of the measured signal over time; as the average of the absolute values of the measured values; as the standard deviation of the absolute values of the measured values, to name but a few.

The method of focusing electromagnetic radiation at the target 1006 comprises two steps: a characterisation process step and a focusing process.

Characterisation Process

As explained above with reference to FIG. 1D, the DMD 1016 may be controlled to provide a sequence of spatial modulations, in this embodiment 2N input patterns 1038 to characterise the diffuser 1020. Since there is a single output ultrasonic intensity signal for each input pattern k some adaptation of the characterising process is required, as explained in the following.

As described above a transmission matrix comprising a plurality of real-valued transmission constants ('RVITM') can be used to approximately connect the input and output light intensities of a disordered medium (e.g. multimode optical fibre, diffuser 1020), so that input binary and gray-scale images can be retrieved from measured intensities of the output speckles. We have found that the RVITM can also be used for focusing light scattered by a disordered medium since the RVITM encodes both the phase and amplitude information of the light field changes from the DMD 1016 to the receiver focus 1025. The present method enables a non-iterative and higher speed characterisation of the disordered medium than has been reported previously, and directly determines a preferred light input (e.g. certain DMD pattern) to achieve improved focusing of light scattered by the disordered medium.

Similarly to the characterisation process described above, the first step is to use a Hadamard matrix H ∈ (−1, +1) with dimensions of N×N to construct two binary matrices $H_1=(H+1)/2$ and $H_2=(-H+1)/2$. Each column of the binary matrix, $[H_1, H_2]$ was then converted to a square matrix that was used to spatially modulate the incident laser beam onto the diffuser 1020 using the DMD 1016, whilst the corresponding light-generated ultrasound waves were recorded by the detector 1022.

According to the principles of photoacoustic signal generation, the amplitude of the received ultrasound signal Q with the kth input pattern displayed at the DMD 1016 can be expressed as: $Q^k = aST\mu_a F^k$, where a is a constant account for the attenuation loss during ultrasound propagation, S is the sensitivity of the detector 1022, Γ is the Grüneisen coefficient (a dimensionless constant defining the conversion efficiency of heat energy to pressure), $\mu_a$ is the optical absorption coefficient, and $F^k$ is the local optical fluence at the target 1006. With $F^k = \int I^{k'} dt/A$, where $\int I^{k'} dt$ is the light intensity, $I^{k'}$, at the target 1006 when the kth pattern is displayed and A is the illumination area at the target 1006. Since the pulse duration T is constant, $F^k$ can be further expressed as $$F^k = \frac{I^k T}{A}$$

where $I^k$ is the average light intensity over T, and we have $$Q^k = \frac{aST\mu_a T}{A} I^k \text{ where } \frac{aST\mu_a T}{A}$$

is a constant under the conditions of the experiment, which we define as $$\alpha = \frac{aST\mu_a T}{A}.$$

As $I^k$ is linearly proportional to $Q^k$ increasing the amplitude of $Q^k$ is equivalent to improving the focusing of light on the target 1006. For example if the amplitude of $Q^k$ can be maximised the light would be focused on the target 1006. By 'focused' it may be meant that the intensity of the light at the target 1006 is increased over the light intensity at the target 1006 when a random DMD pattern is displayed on the DMD 1016. In some embodiments, 'focused' may mean that the light intensity at the target 1006 is at a maximum or close to a maximum over the light intensity at the target 1006 when a random DMD pattern is displayed on the DMD 1016

As explained above the approximate relationship between the intensities of the input and output light field through a disordered medium can be connected by the 24) RVITCs of the RVITM. Accordingly it is also possible to approximately connect the light intensity $I_k$ at the target 1006 and the input patterns 1038 (represented by the matrix $[H_1, H_2]$) by a row of the RVITCs. RVITM$_r$, in the intensity transmission matrix RTITM. The reason there is a single row of RVITCs is that each input pattern A is represented as a single column in the matrix $[H_1, H_2]$. The row of elements RVITM$_r$ corresponds to the light transport from all the DMD input positions to the target 1006, and may be expressed as:

$$[I^1, I^2, \ldots, I^{2N}] = \frac{1}{\alpha}[Q^1, Q^2, \ldots, Q^{2N}] \quad (15)$$
$$= RVITM_r \cdot [H_1, H_2]$$

Equation (15) can be re-arranged as follows:

$$2 \times \frac{1}{\alpha}[Q^1, Q^2, \ldots, Q^{2N}] = 2 \times RVITM_r \cdot [H_1, H_2]$$

$$\frac{1}{\alpha}[2Q^1, 2Q^2, \ldots, 2Q^{2N}] = 2 \times RVITM_r \cdot [H_1, H_2]$$

$$\frac{1}{\alpha}[2Q^1, 2Q^2, \ldots, 2Q^{2N}] - RVITM_r \cdot [D_1, D_1 \ldots D_1]$$

$$= 2 \times RVITM_r \cdot [H_1, H_2] - RVITM_r \cdot [D_1, D_1 \ldots D_1]$$

where $D_1$ is a column matrix of dimension N×1 with all elements having a value of 1. With further re-arrangement:

$$\frac{1}{\alpha}[2Q^1, 2Q^2, \ldots, 2Q^{2N}] - RVITM_r \cdot [D_1, D_1 \ldots D_1]$$
$$= RVITM_r \cdot \{2[H_1, H_2] - [D_1, D_1 \ldots D_1]\}$$

The part of this expression $\{2[H_1, H_2] - [D_1, D_1 \ldots D_1]\}$ is equivalent to [H, −H], so that:

$$\frac{1}{\alpha}[2Q^1, 2Q^2, \ldots, 2Q^{2N}] - RVITM_r \cdot [D_1, D_1 \ldots D_1] = RVITM_r \cdot [H, -H]$$

Recalling that $Q^k = \alpha I^k$ we can also relate the real-valued intensity transmission matrix constants as $RVITM_{PA} = \alpha RVITM_r$ where $RVITM_{PA}$ is a row of matrix elements for the output photoacoustic signal (PA). Further re-arrangement of the equation yields:

$$\frac{1}{\alpha}[2Q^1, 2Q^2, \ldots, 2Q^{2N}] - \frac{1}{\alpha}RVITM_{PA} \cdot [D_1, D_1 \ldots D_1] = \quad (16)$$
$$\frac{1}{\alpha}RVITM_{PA} \cdot [H, -H]$$
$$[2Q^1, 2Q^2, \ldots, 2Q^{2N}] - RVITM_{PA} \cdot [D_1, D_1 \ldots D_1] = RVITM_{PA} \cdot [H, -H]$$

Since the matrix $[D_1, D_1 \ldots D_1]$ represents the input pattern with all micromirrors switched ON, and as that pattern was the first DMD pattern displayed in the experiment, the expression $RVITM_{PA} \cdot [D_1, D_1 \ldots D_1]$ corresponds to the measured output ultrasonic signal is $Q^1$. Equation (16) can be re-written:

$$[2Q^1, 2Q^2, \ldots, 2Q^{2N}] - [Q_1, Q_1 \ldots Q_1] = RVITM_{PA} \cdot [H, -H] \quad (17)$$
$$[2Q^1 - Q_1, 2Q^2 - Q_1, \ldots, 2Q^{2N} - Q_1] = RVITM_{PA} \cdot [H, -H]$$

Recalling that $[H, -H] \cdot [H, -H]^T = [H, -H]^{-1}$, we can multiply equation (17) by $[H, -H]^T$ to yield an expression for $RVITM_{PA}$:

$$RVITM_{PA} = [2Q^1 - Q_1, 2Q^2 - Q_1, \ldots, 2Q_{2N} - Q_1] \cdot [H, -H]^T \quad (18)$$

The dimension of the first matrix on the right hand side of equation (18) is 1×2N and the dimension of the matrix $[H, -H]^T$ is 2N×1. Accordingly the dimension of the matrix $RVITM_{PA}$ is 1×N. i.e. it comprises one row with N elements (recalling that there are N micromirror used by the DMD 1016 to form each input pattern). Thus each micromirror (or group of micromirrors acting as one micromirror) has a corresponding element in the matrix $RVITM_{PA}$.

A positive element in the $RVITM_{PA}$ means that the corresponding micromirror of the DMD 1016 contributes positively (i.e. increases) the output ultrasonic signal, and therefore increases the light intensity at the target 1006. Accordingly the aim of the characterisation step performed by the second computer 1030 is to determine a DMD pattern (which may or may not be not one of the DMD patterns 1038 displayed in the characterising process) that increases the number of elements in $RVITM_{PA}$ that are positive. In some embodiments, the characterisation step may maximise the number of elements in $RVITM_{PA}$ that are positive.

To further understand the physics of how the matrix elements of $RVITM_{PA}$ can be made positive, we investigate below the effect of the nth micromirror of the DMD 1016 on the output ultrasonic signal by considering the contribution of the nth micromirror on the corresponding single element of the matrix $RVITM_{PA}$, denoted $RVITM_{PA}^n$:

$$RVITM_{PA}^n = 2\Sigma_{k=1}^{2N}(Q^k - Q^1)h_n^k = 2\Sigma_{k=1}^{2N}Q^k h_n^k \quad (19)$$

where $h_n^k$ is the element from $[H, -H] \in (-1, +1)$ corresponding to the nth micromirror position (ON or OFF) in the kth DMD input pattern 1038. In equation (19) the term $-Q^1$ can is cancelled out because $[H, -H]$ has the same number of values +1 and −1 in each column. Substituting for $Q^k = \alpha I^k$ equation (19) can be written as:

$$RVITM_{PA}^n = 2\alpha\Sigma_{k=1}^{2N}I^k h_n^k \quad (20)$$

Based on conventional transmission theory the light intensity $I^k$ at the target 1006 corresponding to the kth DMD input pattern 1038 can be expressed at $I^k = |\Sigma_{n=1}^N t_n E_k^n|^2$ where N is the total number of input micromirrors and $t_n$ represents the complex-valued transmission constants. $E_k^n \in (0,1)$ represents the light field at the nth micromirror (either ON or OFF) and is can be expressed in terms of $h_n^k \in (-1, +1)$ as $h_n^k = E_n^k - 1$.

Since the matrix element $RVITM_{PA}^n$ is the sum of the output power over the total number (2N) input DMD patterns 1038, equation (20) can be re-written as:

$$RVITM_{PA}^n = 2\alpha|\Sigma_{n=1}^N t_n E_k^n|^2 h_n^k$$

$$RVITM_{PA}^n = 2\alpha[|t_n|^2 \Sigma_{k=1}^{2N}(E_n^k)^2 h_n^k +$$
$$\Sigma_{i=1, i\neq n}^N |t_i|^2 \Sigma_{k=1}^{2N}|E_i^k|^2 h_n^k + \Sigma_{i=1, i\neq n}^N (t_n t_i^* + t_n^* t_i)$$
$$\Sigma_{k=1}^{2N}(E_n^k E_i^k) h_n^k + E_{i=1, i\neq n}^N \Sigma_{j=2, j\neq n, j>i}^N (t_i t_j^* + t_i^* t_j) \Sigma_{k=1}^{2N}(E_i^k E_j^k) h_n^k] \quad (21)$$

where * denotes the complex conjugate operator.

By noting the structure of the Hadamard matrices and the resulting combinations of mirrors that are ON and/or OFF in the 2N input DMD patterns 1038 it is possible to simplify equation (21). In particular, during the characterisation step (i.e. sequential display of 2N input patterns) the nth micromirror is ON in half of the input patterns, i.e. N times. For the N patterns where the nth micromirror is ON ($h_n^k = 1$, $E_n^k = 1$) the jth micromirror (i≠n) is ON ($E_i^k = 1$) for half of the N patterns, i.e. N/2 times, and the ith and jth micromirrors (i≠j≠n) are simultaneously ON ($E_i^k = 1$, $E_j^k = 1$) half as many times again, i.e., N/4 times. Similarly when the nth micromirror is OFF ($h_n^k = -1$, $E_n^k = 0$), the ith micromirror (i≠n) is switch ON for N/2 times, and the ith and jth micromirrors (i≠j≠n) are simultaneously ON ($E_i^k = 1$, $E_j^k = 1$) N/4 times.

With this in mind, some of the terms in equation (21) reduce as follows:

$$\sum_{k=1}^{2N}(E_n^k)^2 h_n^k = N$$

$$\sum_{k=1}^{2N}|E_i^k|^2 h_n^k = 0$$

$$\sum_{k=1}^{2N}(E_n^k E_i^k)h_n^k = N/2$$

$$\sum_{k=1}^{2N}(E_i^k E_j^k)h_n^k = 0$$

so that equation (21) becomes:

$$RVITM_{PA}^n = 2\alpha\left[N|t_n|^2 + \frac{N}{2}\sum_{i=1,i\neq n}^{N}(t_n t_i^* + t_n^* t_i)\right] \quad (22)$$

$$RVITM_{PA}^n = \alpha N\left[t_n t_n^* + t_n^* t_n + \sum_{i=1,i\neq n}^{N}(t_n t_i^* + t_n^* t_i)\right]$$

$$RVITM_{PA}^n = \alpha N(t_n R^* + t_n^* R)$$

$$RVITM_{PA}^n = \alpha N A_R A_n \cos(\theta_n - \emptyset_R)$$

where R is the output light field at the target 1006 when all of the micromirrors are switched ON. $\emptyset_R$ and $A_R$ are the phase and amplitude of R: $\theta_n$ and $A_n$ are the phase and amplitude of $t_n$, respectively. According to equation (22), when the phase $\theta_n$ of the transmission constant $t_n$ is within the range [$\emptyset_R - \pi/2$, $\emptyset_R + \pi/2$] the value of $RVITM_{PA}^n$ is positive and increases the intensity of ultrasonic signal at the target 1006, which corresponds to an increase in constructive interference of the light field for focusing. If that is so, the nth micromirror corresponding to $RVITM_{PA}^n$ should be switched ON. On the other hand if the phase $\theta_n$ of the transmission constant $t_n$ is outside the range [$\emptyset_R - \pi/2$, $\emptyset_R + \pi/2$] the value of $RVITM_{PA}^n$ is negative and decreases the intensity of the ultrasonic signal at the target 1006, which corresponds to a decrease in constructive interference of the light field. In this case, the nth micromirror corresponding to $RVITM_{PA}^n$ should be switched OFF.

Figure 11:
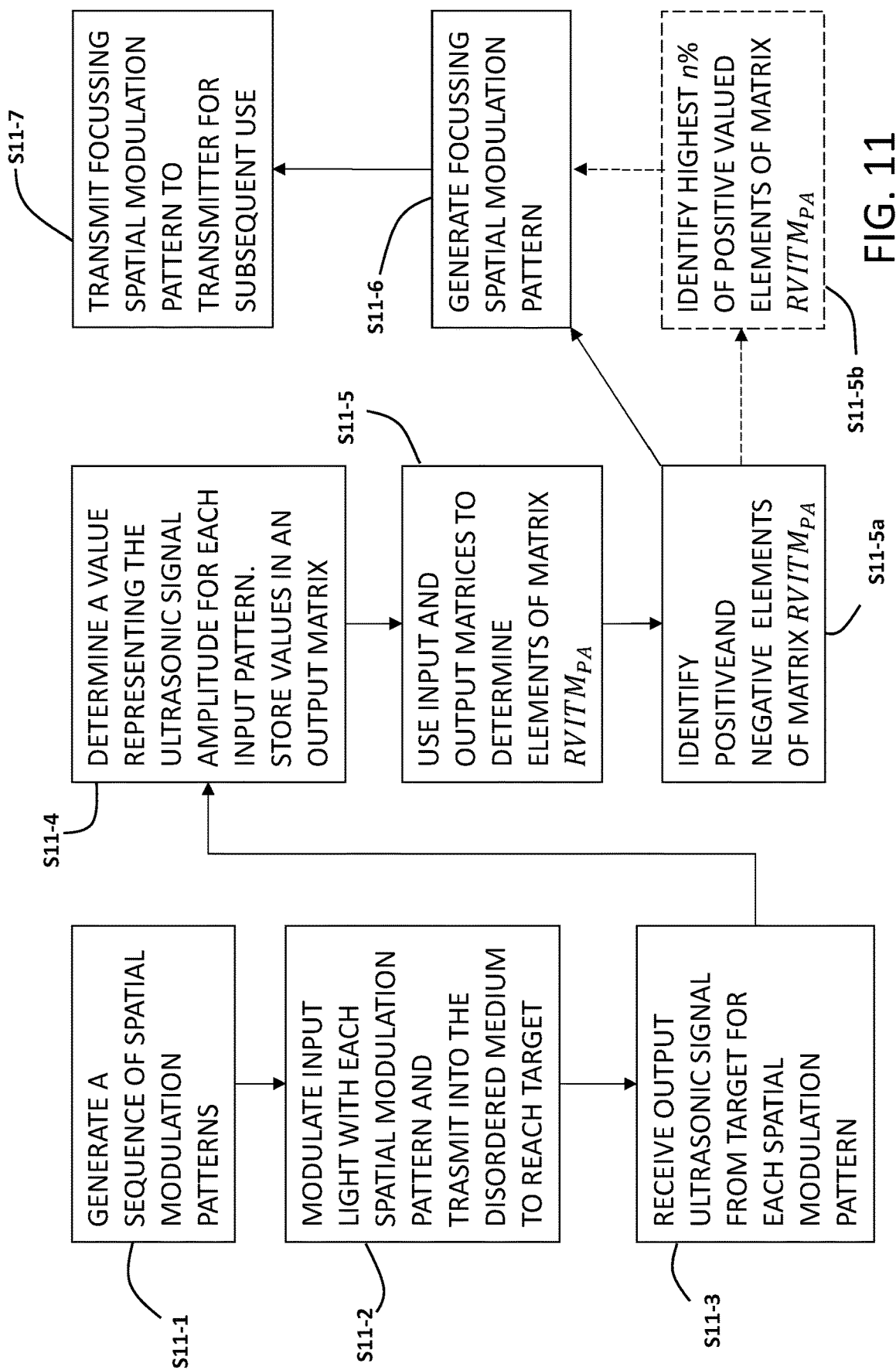
FIG. 11 is a schematic diagram of steps of a characterisation process according to an embodiment of the present invention.

Continuing with the description of the characterisation process, reference is made to FIG. 11. At step S11-1 a sequence of spatial modulations is generated. In this embodiment the sequence of spatial modulation comprises the input patterns 1038, as described above. There may be 2N input patterns 1038. At step S11-2 the 2N input patterns 1038 may be displayed sequentially on the DMD 1016, thereby modulating the intensity of each pulse of laser light. There be one pulse of laser light per input pattern 1038. From the DMD 1016 the pulse of laser light is transmitted into the disordered medium, such as the diffuser 1020. The laser light is scattered within the diffuser 1020, and then reaches the target 1006. By means of the photoacoustic effect a portion of the energy in the pulse of laser light is converted to ultrasound waves. At step 11-3 an output ultrasonic signal may be received by the detector 1022 and a time sequence of digital values may be generated by the DAQ 1032. The output ultrasonic signal represents the amplitude of the ultrasound at the target 1006 and does not include any phase information. At step 1-4 the digital values may be processed by the computer and a single value generated that represents the amplitude of the ultrasound signal at the target 1006. The computer 1030 may store the single value for subsequent use. Following display of the 2N patterns, the computer 1030 will store 2N values representing the ultrasonic signal amplitude measured for each pattern. The 2N values may be stored as an output matrix of dimension 1×2N.

At step S11-5 the computer begins determination of the focusing spatial modulation pattern using the matrix $RVITM_{PA}$ where each element n of the matrix is determined using equation (19):

$$RVITM_{PA}^n = 2\sum_{k=1}^{2N}Q^k h_n^k$$

recalling that $Q^k$ is the ultrasonic signal amplitude stored by the computer 1030 for the kth pattern input by the DMD 1016, and $h_n^k$ is either +1 or −1, i.e. whether the nth mirror is ON or OFF in the kth pattern. In this way, each element of $RVITM_{PA}$ is determined by the following steps:
1. for the mirror n=1:
   a. for input pattern k=1 retrieve the value $h_n^k$, i.e. whether the mirror n was on or off for input pattern k;
   b. retrieve the ultrasonic signal value $Q^k$ and determine and store the product $Q^k h_n^k$;
   c. repeat steps (i) and (ii) for input patterns k=2 . . . 2N;
   d. sum the products $Q^k h_n^k$, and store as element no in the matrix $RVITM_{PA}$ the magnitude of the sum and an indication whether the sum is positive or negative; and
2. set n=2 and repeat steps (i) to (iv).

The outcome of these steps is that the computer stores 1030 the matrix $RVITM_{PA}$ containing N real numbers, each being either positive or negative.

At this point the method of FIG. 1I may proceed in two different ways. In some embodiments, the method proceeds from step S11-5, to step S11-5a and then to step S11-6. In other embodiments (described later in this document), the method proceeds from step S11-5, to step S11-5a, then to step S11-5b and then to step S11-6.

At step 11-5a the computer 1030 identifies whether each element of the matrix $RVITM_{PA}$ holds a positive real number or a negative real number. At step S11-6 the focusing spatial modulation pattern is generated in which the computer 1030 sets state indicators of the focusing spatial modulation pattern according to the determination made in step S11-5. For example, when a positive real number of matrix $RVITM_{PA}$ is identified, a state indicator in the focusing spatial modulation pattern is set so that the corresponding micromirror is to be switched to an 'ON' state. When a negative real number of matrix $RVITM_{PA}$ is identified, a state indicator in the focusing spatial modulation pattern is set so that the corresponding micromirror is to be switched to an 'OFF' state.

The state indicators may be stored in any computer-processable data structure including, but not limited to, a list and an array. The data structure may comprise any suitable data type acting as the state indicator, such as the Boolean data type. For example, the focusing spatial modulation pattern could comprise state indicators in the form of binary values e.g. +1 or −1, or +1 or 0 to indicate whether each mirror of the DMD 1016 should be set to an ON state or an OFF state in the focusing spatial modulation pattern It is recalled that, owing to the properties of Hadamard matrices and the way the input patterns have been constructed from them, each mirror n is ON for half the number of input patterns 1038 and OFF for half the number of input patterns. The function of equation (19) is to compare the sum of the ultrasonic signal amplitude values when the mirror n is ON (directing light to the diffuser 1020 and target 1006) to the sum of the ultrasonic signal amplitude values when the mirror n is OFF (not directing light to the diffuser 1020 and target 1006). If the comparison is positive, this indicates that when the mirror n is ON there is constructive interference of light at the target 1006, indicating that light is focused in the plane of the target. On the other hand if the comparison is negative, this indicates that when the mirror n is ON there is negative interference of light at the target 1006, indicating that light is not focused.

Thus the elements of the matrix $RVITM_{P4}$ enable the focusing spatial modulation pattern 1036 to be determined as described above which will tend to increase focus of light at the target 1006. The focusing spatial modulation pattern 1036 comprises an indication whether each mirror (or a group of mirrors acting in unison) should be set to ON or OFF in order to increase focusing at the target 1006. At step S11-6 the focusing spatial modulation pattern 1036 can be sent to the transmitter 1002 for subsequent use in focusing light onto the target 1006 through the diffuser 1020. A number of different communication mechanisms could be used to send the focusing spatial modulation pattern 1036 to the transmitter 1002, such as any wired or wireless communication system e.g. WiFi, Bluetooth, cellular, electrical cables, etc.

Focusing Process

Figure 12:
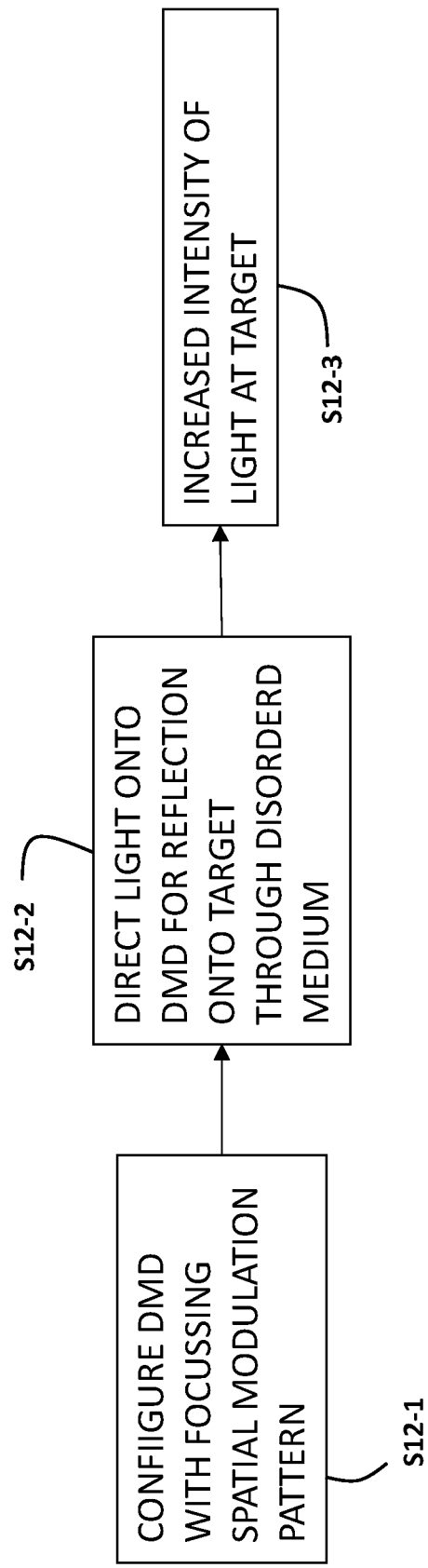
FIG. 12 is a schematic diagram of steps of a focusing process according to an embodiment of the present invention.

Once the focusing spatial modulation pattern 1036 (or any computer-processable equivalent) has been received by the transmitter 1002 it may be stored (in a computer memory remotely or locally accessible to the transmitter 1002) for subsequent use. FIG. 12 shows steps of a focusing method performed by the transmitter 1002. At step S12-1 the transmitter may configure the DMD 1016 with the focusing spatial modulation pattern 1036. In other words, the DMD 1016 is configured so that its mirrors match the focusing spatial modulation pattern 1036. At step S12-2 the transmitter 1002 may cause the laser 1010 to transmit laser light toward the DMD 1016. Mirrors that are ON direct light toward the diffuser 1020 and mirrors that are OFF direct light away from the diffuser 1020. At step S12-3 there is an increased intensity of light at the target 1006 compared to a random pattern on the DMD 1016 for example.

It is noted that the laser light need not be the same as the laser light used to perform the characterising process. For example the laser light used at this step may be a series of individual pulses, an intensity-modulated continuous wave or as a continuous wave. Furthermore the wavelength of light may be slightly different between the characterising process and the focusing process.

In some embodiments, the characterising process may be repeated for different wavelengths, and one or more focusing spatial modulation pattern determined and stored for each wavelength. In use, the different focusing spatial modulation patterns may be used with the respective wavelength to provide a multi-spectral imaging function.

Results

FIG. 13 shows various results obtained when using random patterns on the DMD 1016 compared to a focusing spatial modulation pattern 1036 obtained using the characterisation process described above. FIG. 13A shows a graph of time (μs) versus normalised amplitude for the ultrasonic signal measured by the detector 1022. Trace 1050 shows the average of 64 different ultrasonic signals measured when 64 different random DMD patterns were sequentially displayed on the DMD 1016. Trace 1052 shows the average of 64 different ultrasonic signals measured when the DMD 1016 was configured with a focusing spatial modulation pattern 1036. As can be seen, the trace 1052 (focusing spatial modulation pattern) provides a greater signal amplitude than the trace 1050 (random DMD patterns). This greater signal amplitude corresponds to a greater light intensity at the target 1006, and in this experiment the signal amplitude when using the focusing spatial modulation pattern 1038 was about 6.7 times greater than the signal amplitude when using the random DMD patterns.

Figure 13A:
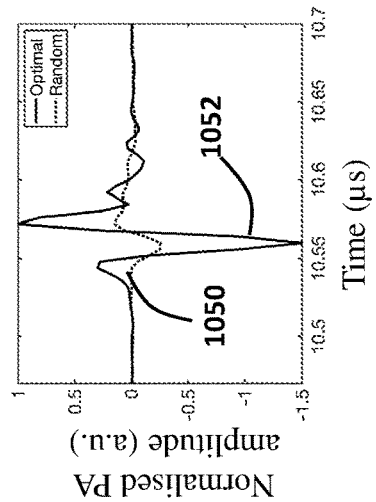
FIG. 13 are various results illustrating effects of random DMD patterns and spatial modulation patterns obtained according to some embodiments of the invention.
Figure 13E:
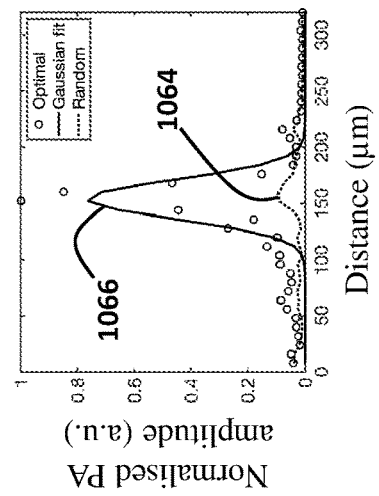
Figure 13F:
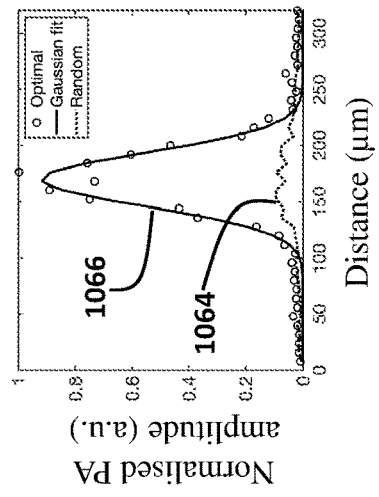
Figure 13B:
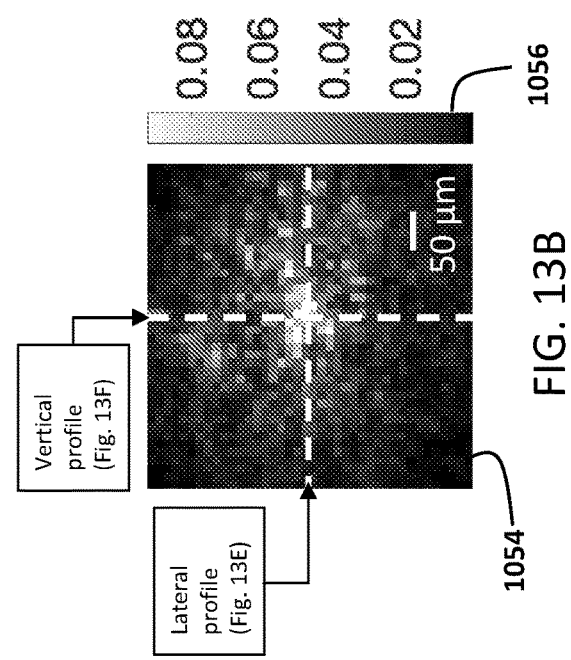
Figure 13C:
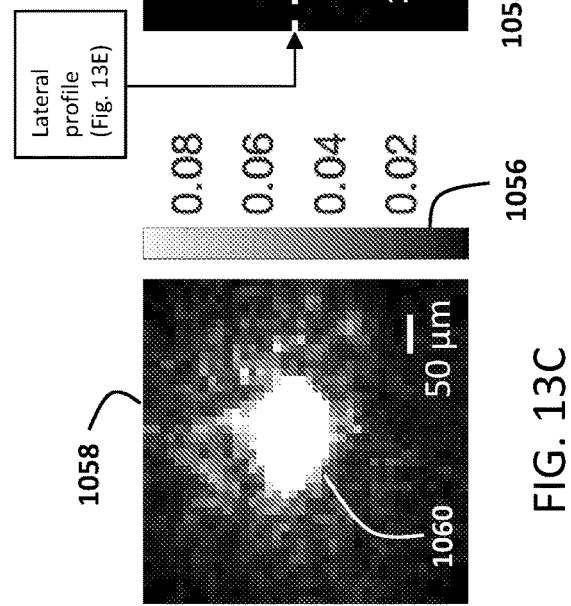
Figure 13D:
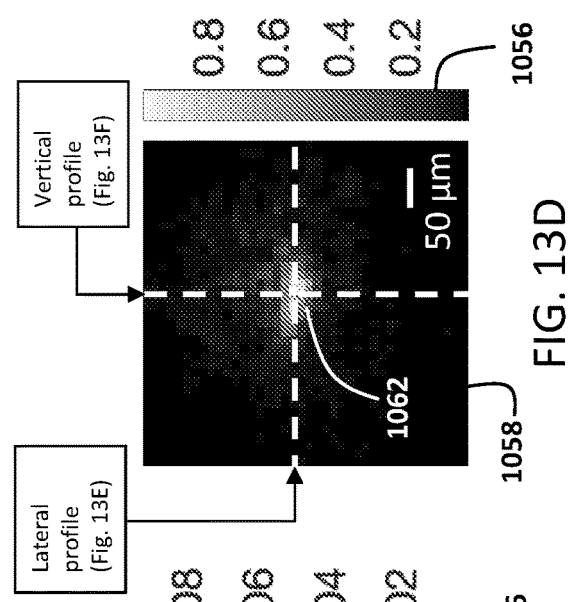

FIG. 13B shows the optical speckle pattern 1054 obtained using one of the 64 different random DMD patterns when the detector 1022 was replaced with a CCD camera. A grayscale key 1056 indicates the scale of the normalised light intensity of the speckle pattern 1054. In FIG. 13B the optical speckle pattern was spread across an area measuring approximately 320 μm by 320 μm at the target 1006. FIG. 13C shows the optical speckle pattern 1058 obtained using the focusing spatial modulation pattern 1036. As can be seen light was concentrated on a smaller area than the optical speckle pattern 1054 and contained a region 1060 of saturated pixels indicating high light intensity in the region 1060. FIG. 13D shows the same optical speckle pattern 1058 but with the use of a neutral density filter to reduce the light intensity reaching the target. The improved light focusing effect when using a focusing spatial modulation pattern 1036 compared to a random DMD pattern (see FIG. 13B) can be clearly seen in FIG. 13D.

FIG. 13E is a graph of distance (in μm) versus normalised ultrasonic signal amplitude (arbitrary units) taken along the 'lateral profile' dashed line shown in FIGS. 13B and 13D, and FIG. 13F is a similar graph but taken along the 'vertical profile' dashed line in FIGS. 13B and 13D. Trace 1064 shows that the ultrasonic signal intensity (the average of the 64 different signals) is generally low across the full width of the CCD camera, with a low peak toward the centre. Traces 1066 are Gaussian fits of the intensity data points (small open circles in the graphs) along the lateral and vertical profiles. The traces 1066 clearly show a pronounced peak in intensity at and near the centre of each profile, indicating the improvement given when using the focusing spatial modulation pattern 1036. The dimensions of the optical focus (indicated by the full width at half maximum of the Gaussian fits (traces 1066) were approximately 56 μm by 40 μm (which is consistent with the ultrasonic transducer focus size of approximately 49 μm diameter). The ratio of the average values of the ultrasonic signal intensity in the focal region 1062 before (FIG. 1313) and after (FIG. 13D) focusing was found to be 6.89, indicating a considerable increase in light intensity in the region 1062.

Figure 14:
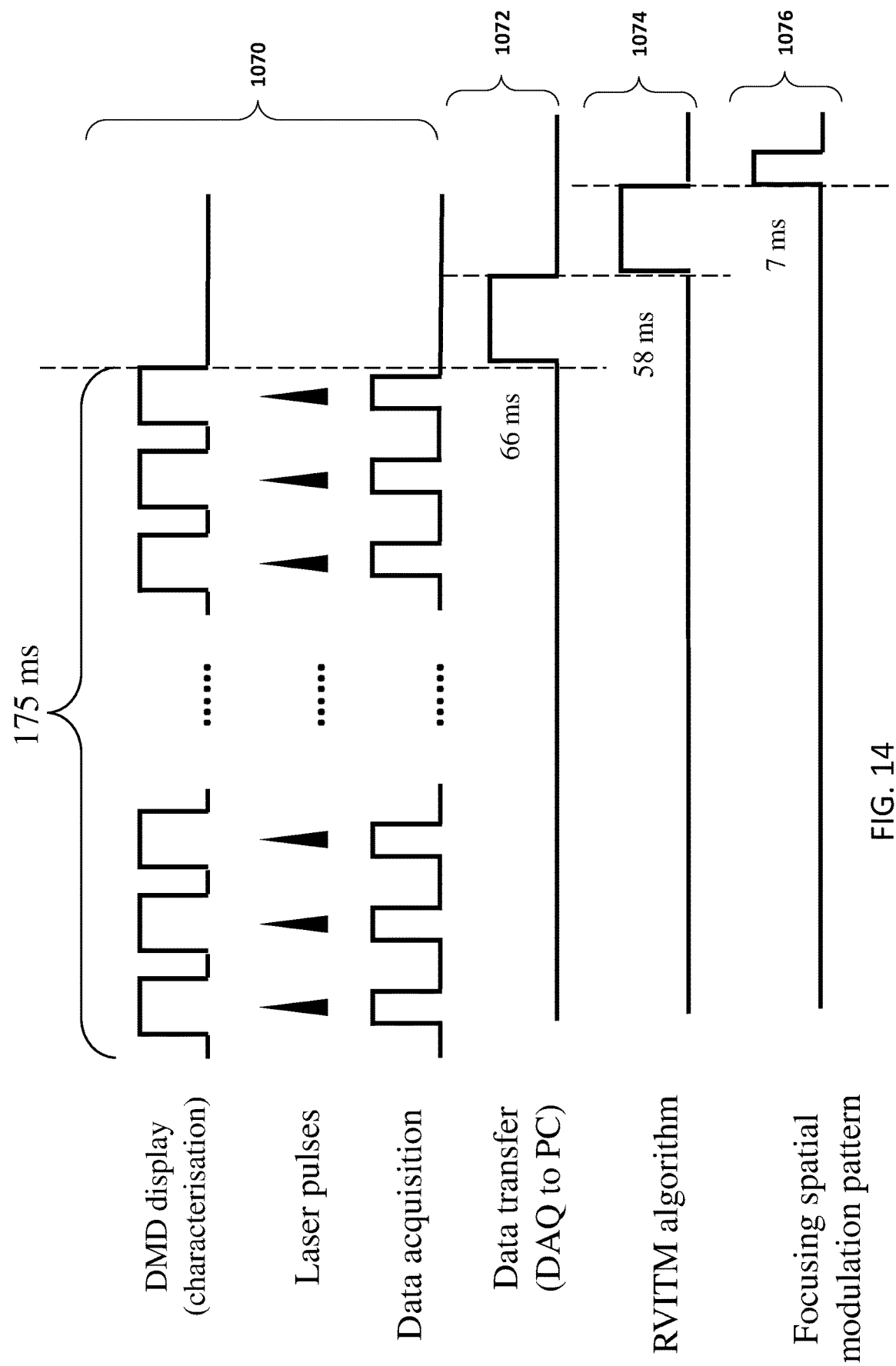
FIG. 14 is an illustration of time taken to perform an embodiment of a method according to the present invention.

FIG. 14 is an illustration of the time taken to perform an embodiment of the method comprising the characterising and focusing process described above. In this embodiment 8.192 input patterns ($[H_1, H_2]$) 1038 were uploaded into the memory of the DMD 1016. This time was not recorded as a cost as, in practice, this step can be completed in advance of the need to characterise a disordered medium and focus light at a target within or beyond the disordered medium. During a first phase 1070 of the method the 8,192 input patterns 1038 were displayed sequentially on the DMD 1016 at a rate of 47 kHz, taking a time of 175 ms. During the same time period the laser 1010 emitted pulses of light at the same rate (synchronised by the synchronisation device 1018), at least a part of each pulse reflected from the DMD 1016, through the diffuser 1020 and onto the target 1006. The detector 1022 measured an ultrasonic signal corresponding to the light intensity received at the target 1006, output an analogue signal which was received and processed by the DAQ 1032 into digital data and stored. During a second phase 1072 the digital data representing all of the ultrasonic signals was sent from the DAQ 1032 to the memory 1034 of the computer 1030, taking approximately 66 ms. During a third phase 1074 the digital data received by the computer was processed as described above to determine the elements of the matrix $RVITM_{P4}$, i.e. the focusing spatial modulation pattern 1036 to achieve improved focusing at the target 1036. The third phase 1074 took approximately 58 ms. During a fourth phase 1076 the focusing spatial modulation pattern 1036 was uploaded to the t) memory of the DMD 1016 and displayed, taking approximately 7 ms. Thus the total time taken by the method to characterise and focus was 306 ms. It is noted that the most significant time cost is the first phase 1070. Time savings could be made here with a spatial light modulator that is able to display the input patterns 1036 faster for example. Another way to speed up the characterising and focusing process would be to reduce the number of mirrors of (or used by) the DMD 1016, although it is expected that lower light intensities would be achieved at the focal spot on the target 1006. The time cost of the second phase 1072 and the third phase 1074 could be reduced by using a field programmable gate array (FPGA) for example.

Example Application: Focusing Light Through Multi-Mode Optic Fibres

Figure 15A:
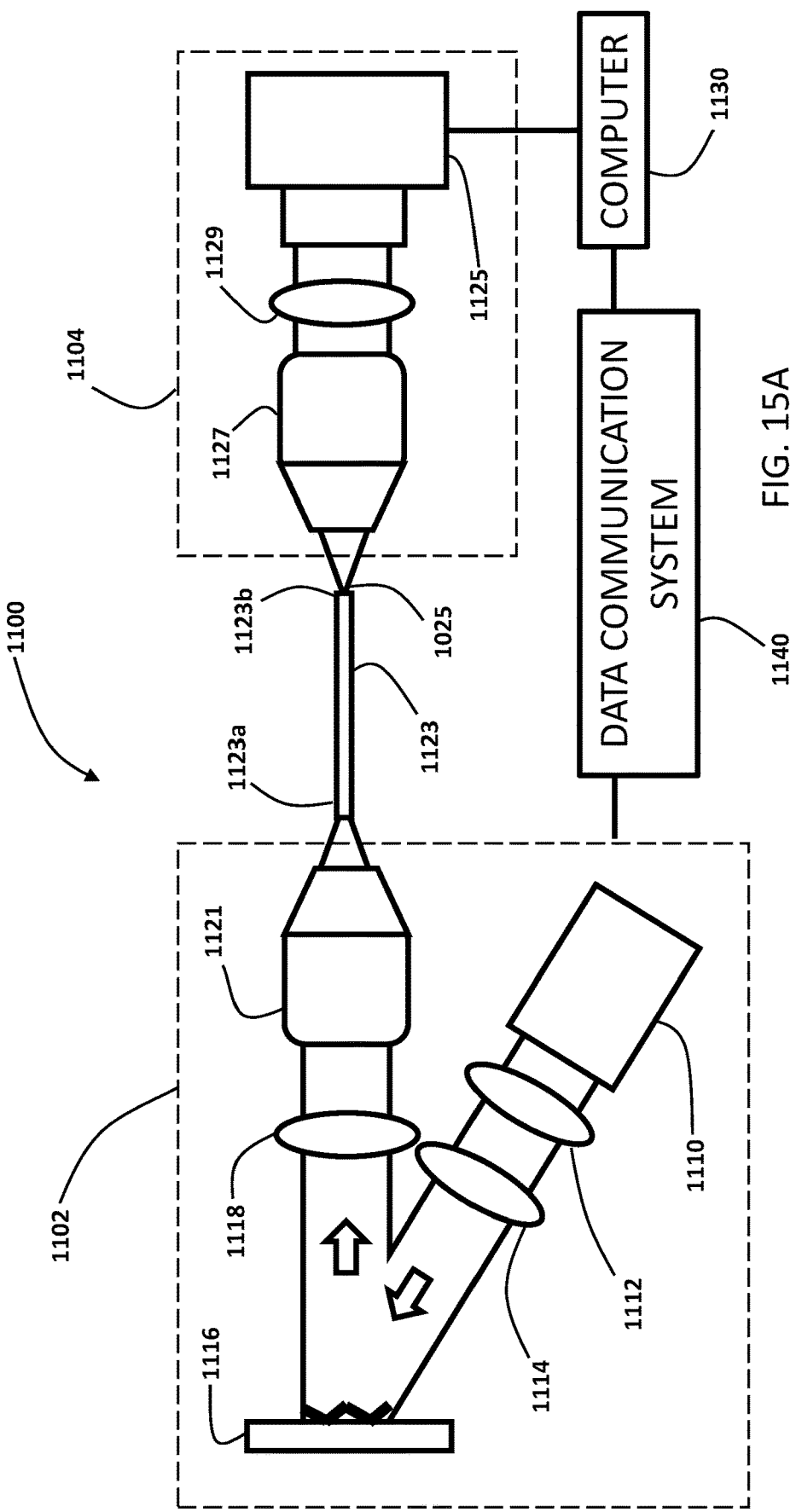
FIG. 15A is a schematic diagram of an embodiment of an apparatus according to the present invention.
Figure 15B:
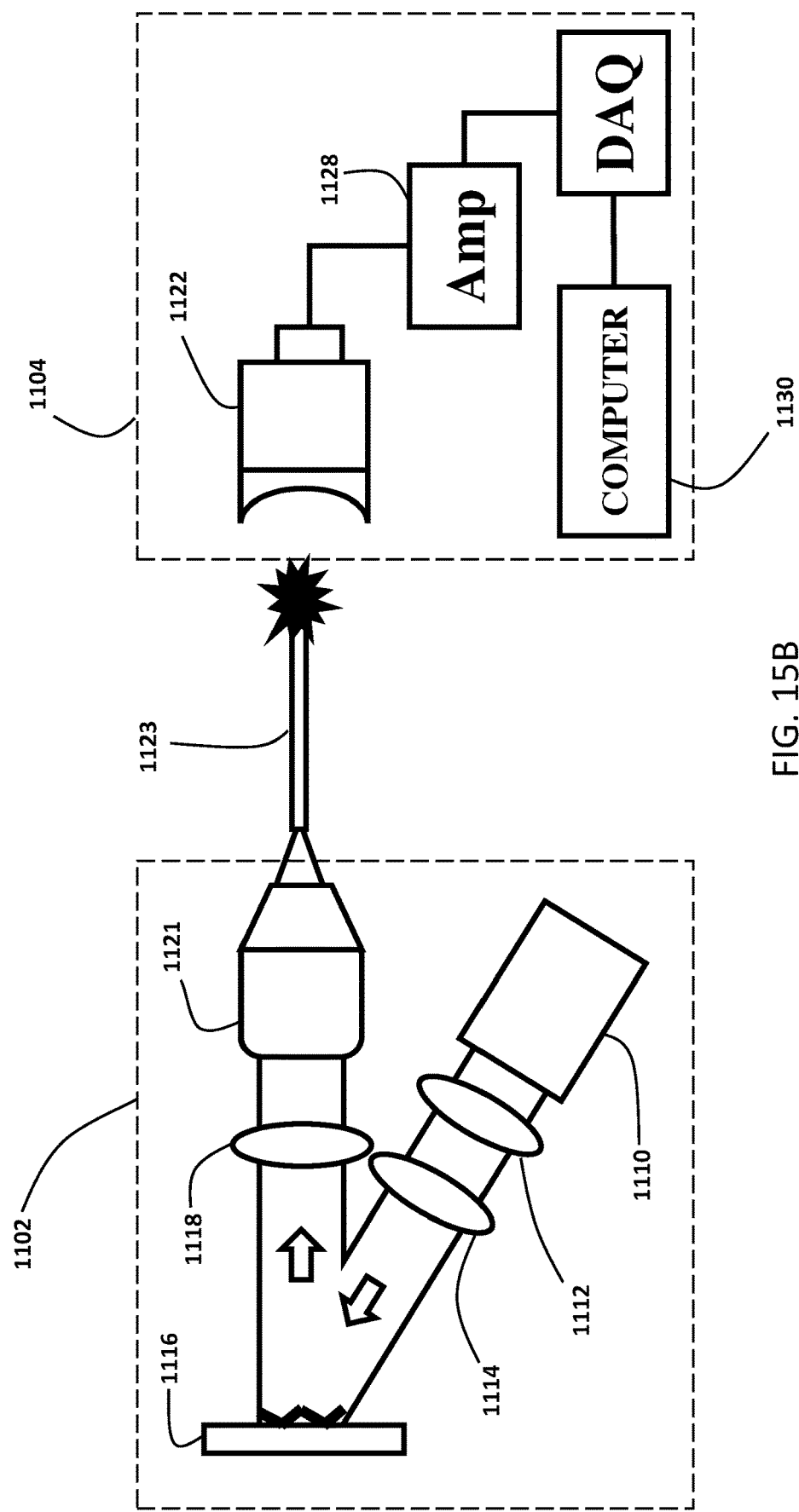
FIG. 15B is a schematic diagram of an embodiment of an apparatus according to the present invention.

Referring to FIGS. 15A and 15B an apparatus generally identified by reference numeral 1100 is like the apparatus 1000 shown in FIG. 10, with like reference numerals indicating like parts. For the sake of brevity, the description of these parts will not be repeated, but these features are incorporated into this embodiment by reference to FIG. and the description above.

The transmitter 1102 is like the transmitter 1002 except for the following. The first lens 1112 may be a tube lens with a focal length of 30 mm, the second lens 1114 may be a tube lens with a focal length of 75 mm, and the third lens 1118 may be a tube lens with a focal length of 50 mm. Furthermore an objective lens 1121 may be positioned after the third convex lens 1118. The purpose of the objective lens 1121 is to direct light from the laser 1110 into a first end 1123a of a multi-mode optic fibre 1123. The multi-mode optic fibre is a disordered medium, and may be like any multi-mode optic fibre described herein. In some embodiments the multi-mode optic fibre has a diameter in the range several tens of micrometres to several millimetres. In some embodiments the length of the multi-mode optic fibre is such that the speckle decorrelation time is longer than the time taken to characterise and generate the focusing spatial modulation pattern. It is expected that such length may be anywhere in the range several millimetres to several tens of kilometres. In use the multi-mode fibre 1123 scatters light from the laser 1110, generating an output speckle pattern (i.e. unfocused light) at a second end 1123b of the multi-mode optic fibre 1123.

In order to characterise the multi-mode optic fibre 1123 for focusing at or near the second end 1123b, the receiver 1104 of the apparatus 1110 may comprise a CCD camera 1125 for receiving light from the laser 1110 through a second objective lens 1127 and a fourth tube lens 1129 (which may have a focal length of 100 mm). A purpose of the objective lens 1127 is to provide the receiver focus 1025 in front of the CCD camera 1125 at the second end 1123b of the multi-mode optic fibre 1123 where light is emitted. Accordingly the objective lens 1127 is positioned so that its focal point at the second end 1123b of the fibre 1123

In use, the characterisation process is repeated as described above in conjunction with the apparatus 1000. However instead of a single ultrasonic signal (which provides an indirect measurement of light intensity at the target 1006) the receiver 1104 provides an image indicating a plurality of light intensity values at the second end 1123b of the fibre over the field of view of the CCD camera 1125. In particular the CCD camera 1125 comprises a plurality of output pixels, each of which provides a signal indicating the intensity of light received by that output pixel and this data is provided to the computer 1130 in the form of an image, or as a dataset comprising a time series of intensity data values for each output pixel. For each input pattern 1038 displayed on the DMD 1116 the computer stores the image (or the time series of intensity data values) taken by the CCD detector 1125.

So instead of a single ultrasonic signal intensity value ($Q^k$) determined for each input pattern 1038 (e.g. in the embodiment of FIG. 10), there is now a plurality of light intensity values recorded for each input pattern 1038, with a single intensity value determined for each output pixel. In particular, once all of the input patterns 1038 have been displayed, the second computer 1130 has a set of k images (or k datasets), and determines k light intensity values for each output pixel. For each output pixel the computer 1130 uses the k intensity values in equation (19) to determine a focusing spatial modulation pattern 1036 for that output pixel. After processing the data, the second computer 1130 will have generated and stored a plurality of focusing spatial modulation patterns 1036 (in this embodiment there would be N focusing spatial modulation patterns). These focusing spatial modulation patterns 1036 are sent to the transmitter 1102 using the data communication network 1140. The number of focusing spatial modulation patterns 1036 may or may not be the same as the number of output pixels of the CCD camera 1125. For example, if the field of view of the second objective lens 1127 is circular, the number of output pixels may corresponding to the circular are of light reaching the CCD camera 1125 from the second objective lens 1127. In another example, output pixels could be treated in groups by the second computer 1130 with a single light intensity value for each group being determined based on the light intensity values recorded for each output pixel in the group, per image k.

Once the transmitter 1102 has received the focusing spatial modulation pattern 1036 it can be loaded into the memory of the DMD 1116 for display. When in use (for example as a photoacoustic endoscope) the second end 1123b and a portion of the multi-mode optic fibre 1123 may be inserted into a body cavity for viewing of the interior of the human or animal body. In use, the receiver 1102 of FIG. 15A is replaced with a receiver 1102 as shown in FIG. 15B. The receiver 1102 of FIG. 15 comprises an ultrasonic detector 1122 for receiving pulses of ultrasonic sound generated by the photoacoustic effect as the pulses of laser light leave the second end 1123b of the fibre 1123 and are scattered and absorbed by tissue.

In order to generate an image for viewing by a person, the DMD 1116 is configured to display the particular focusing spatial modulation pattern 1036 for each output pixel in sequence. When displayed, a pulse of laser light (or series of pulses, or an intensity-modulated continuous wave) is transmitted toward the DMD 1116, a portion is reflected into the fibre 1123 (by ON mirrors in the pattern) and a portion directed away from the fibre 1123 (by OFF mirrors in the pattern). The pulse is scattered inside the fibre 1123. An ultrasonic signal is recorded by the detector 1122, sent to the DAQ 1132 and on to the computer 1130. The second computer 1130 may store a value (or a time series of values) representing the ultrasonic signal in such a way that it associated with the corresponding output pixel of the CCD camera 1125 used in the characterising process. This process is repeated using each of the focusing spatial modulation patterns 1136 in sequence so that the computer ends up storing a set of ultrasound signal values, each value (or a time-series of values) associated with a corresponding output pixel of the CCD camera 1125. Since this data represents a 2D array of ultrasound transducers (corresponding to the 2D array of pixels of the CCD camera 1125) it can be processed by the computer 1130 to produce a variety of different image reconstructions, including (but not limited to) a volumetric (3D) image generated using maximum intensity projection with depth-resolved colour map, although other image reconstruction algorithms are possible (such as a 3D rendering algorithm). Image reconstruction may be performed by image reconstruction software on the second computer 1130 or the ultrasonic data stored and transmitted to a remote computer (e.g. accessible over a data communication network) for image reconstruction.

In order to illustrate some of the steps in the process described above, and to show some reconstructed photoacoustic images obtained using this process, reference is made to FIG. 16. FIG. 16A is a speckle pattern 1150 take by CCD camera 1125 before any characterisation of the fibre 1123 has been conducted. As can be seen, the light intensity reaching the CCD camera 1125 from the second end 1123b of the fibre has an approximately random distribution. FIG. 16B is a DMD mirror configuration 1152 of a focusing spatial modulation pattern determined by the characterising process for focusing light onto one pixel of the CCD camera 1125 as described above. White regions 1154 of the display are 'ON' micromirrors and black regions 1156 of the display are 'OFF' micromirrors. FIG. 16C shows an image 1158 taken by the CCD camera 1125 when the focusing spatial modulation pattern of FIG. 16B was displayed by the DMD 1116 and illuminated with continuous wave (CW) laser light. FIG. 16D is a mesh plot 1159 of the pixel array of the CCD camera 1125 in the X and Y axis (horizontal plane) with light intensity along the Z axis (vertical). As can be seen light was focused onto a small region of pixels 1160 and not onto any other pixels. A strong peak 1161 of the light intensity in FIG. 16D shows the degree of focusing achieved. This demonstrates that, by using different focusing spatial modulation patterns, it is possible to focus laser light onto different groups of pixels of the CCD camera 1125 (or even onto to different individual pixels). For example, FIG. 16E shows that by using another focusing spatial modulation pattern light is focused onto a different group of pixels compared to FIG. 16C.

The size of focus is determined by a number of factors including the wavelength of the light, the distance between the focus and the fire distal end, and the numerical aperture (NA) of the fibre. There are different cases: (1) if light is focused at distal fibre tip to a small distance in front of the fibre tip facet so that the NA of the output focusing light is larger than fibre NA, the size of the focus is determined by fibre NA. (2) If the light is focused to a large distance from the fibre tip, so that the actual NA of the output focusing light is smaller than the fibre NA, the size of focus is determined by the actual output NA.

FIG. 16F is a 3D photoacoustic image 1162 obtained using the apparatus of FIG. 15B. It shows a carbon fibre sample placed at the second end 1123b of the fibre 1123 using water or an ultrasonic coupling gel for transmission of ultrasound. The ultrasonic data obtained was processed using a maximum intensity projection reconstruction algorithm to generate a 3D image. It is recalled that a focusing spatial modulation pattern 1036 has been determined for each output pixel of the CCD camera 1125. In this example, the CCD camera 1125 has 400×400 pixels. When the apparatus of FIG. 15B is used to generate an image, it is noted that it is not necessary to use all of the focusing spatial modulation patterns 1036 corresponding to all 400×400 pixels of the CCD camera 1125. In this way it is possible to obtain different fields of view and images with different spatial resolutions and imaging frame rates. In particular it is possible to select a combination of patterns 1036 from all of the patterns 1036 to make up an image. For an image with a lower spatial resolution and a higher imaging frame rate, a combination of non-adjacent patterns 1036 can be selected, for example patterns 1036 corresponding to every $2^{nd}$, $3^{rd}$, $4^{th}$ pixel, etc. are used. For a narrower field of view a combination of patterns 1036 can be selected in which patterns 1036 can be selected corresponding to a block of adjacent pixels of dimension x and y (where both x and y are smaller than then horizontal and vertical numbers of pixels in the CCD respectively). For example FIGS. 16F and 16G show 2D photoacoustic images 1162 and 1164 respectively that were generated using non-adjacent focusing spatial modulation patterns 1036, in this case corresponding to every other pixel of the CCD 1125 thereby generating a 200×200 pixel image. In FIG. 16H a 3D photoacoustic image 1166 was generated using a combination of focusing spatial modulation patterns 1036 corresponding to a block of adjacent pixels of the CCD camera 1125, in this case corresponding to a 200×200 block of pixels in the centre of the CCD. In this way the photoacoustic image 1166 has a narrower field of view than the photoacoustic images 1162 and 1164 in FIGS. 16F and 16G.

Figure 16E:
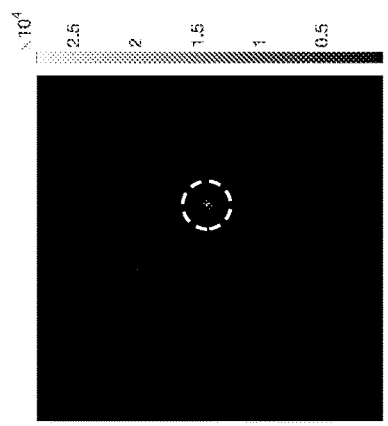
FIG. 16E is an image of light focused onto a second region of a CCD camera when light is spatially modulated using a pattern different to the pattern of FIG. 16B.
Figure 16D:
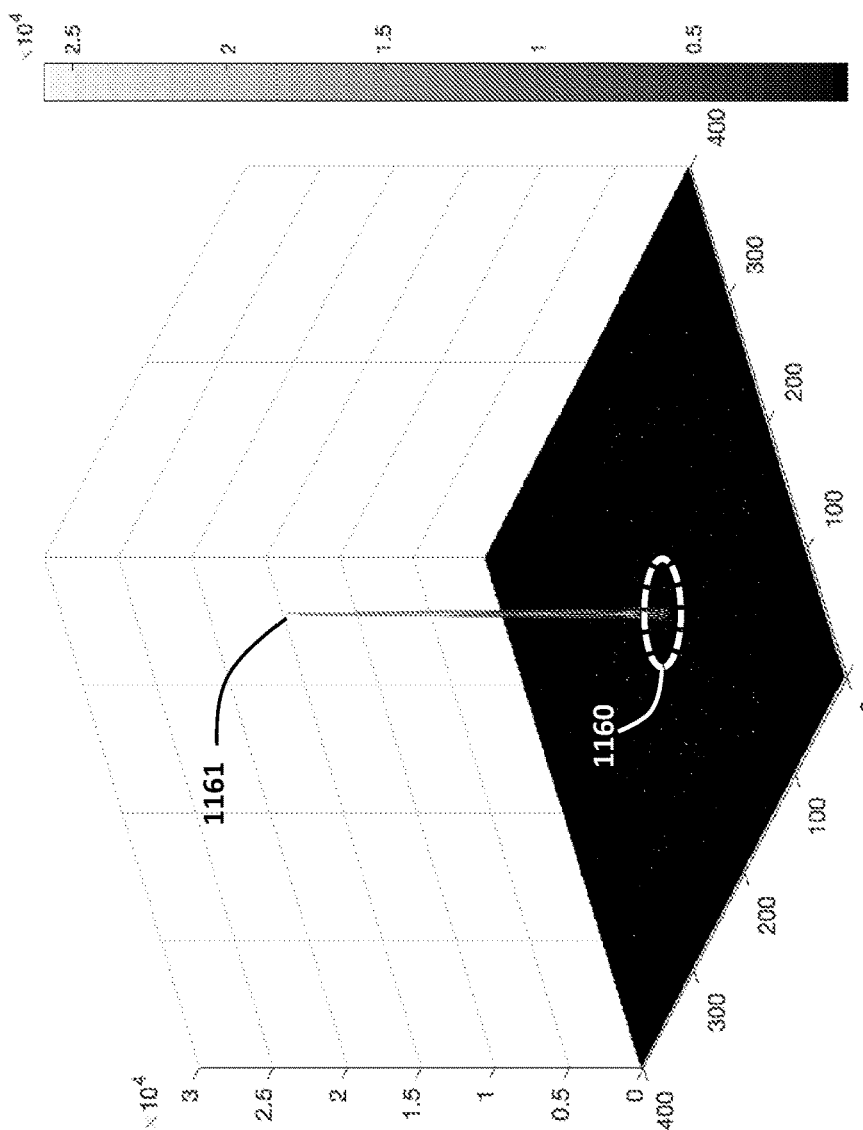
FIG. 16D is a graph illustrating the intensity of the light focus in FIG. 16C.
Figure 16K:
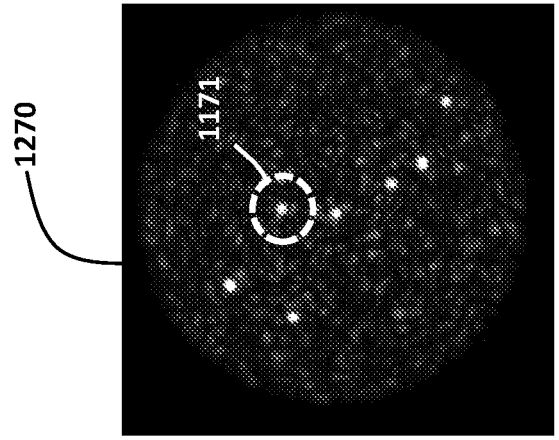
FIGS. 16I-16K are images of light focused onto multiple different regions of a CCD camera.
Figure 16J:
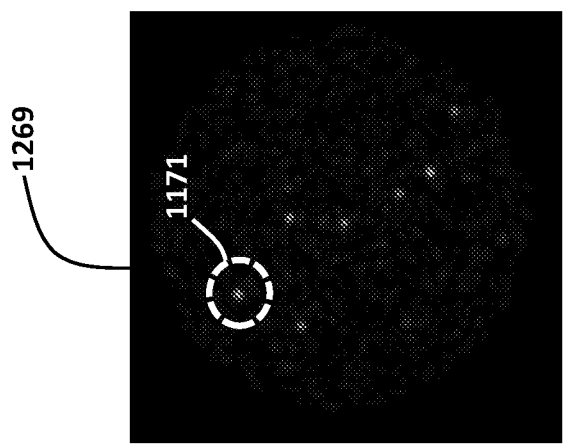
Figure 16I:
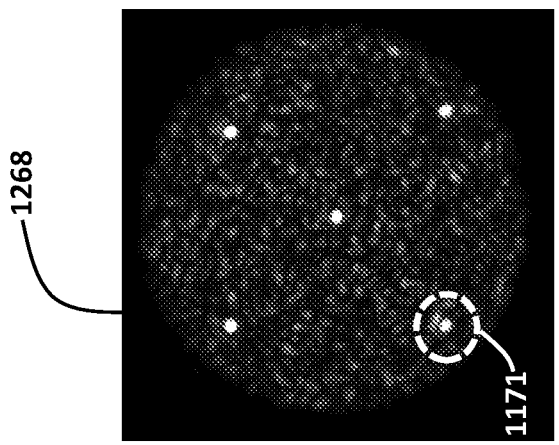

FIGS. 16I-16K speckle patterns 1268, 1269 and 1270 respectively showing focusing of light at a plurality of areas or regions 1271 of the CCD camera simultaneously (note that only one area or region is referenced in each of FIGS. 16I-16K for illustration). FIG. 16K is a longer exposure version of FIG. 16J. To focus light in multiple areas or regions simultaneously, each area or region is characterised as described above to determine a focusing spatial modulation pattern that will improve the focus of light in that area or region. Once a focusing spatial modulation pattern has been determined for each one, the patterns are processed further by computer in order to determine a multi-focusing spatial modulation pattern that will focus light simultaneously in the plurality of areas or regions. In particular, the corresponding state indicators in each pattern are summed (as binary values 0 and 1) and then averaged (mean) to determine a value between 0 and 1. The average value is then subjected to a threshold to determine whether the corresponding state indicator of the multi-focusing binary modulation pattern will set the corresponding micromirror to ON or OFF. For example the threshold could be 0.5, so that if an average value is greater than 0.5 the state indicator of the multi-focusing spatial modulation pattern is set to ON and if an average value is less than 0.5 the state indicator of the multi-focusing spatial modulation pattern is set to OFF. By processing the patterns in this way, a balance is struck between them that permits light to be focused in multiple areas or regions.

FIGS. 17A-17D are schematic drawings showing some example tip embodiments of the second end 1123b of the multi-mode fibre 1123 that can be used in FIGS. 15A and 15B. In FIGS. 17A-17D a region of biological tissue is generally indicated by reference numeral 1172. The biological tissue 1172 may be a tissue sample taken from a human or animal (for example for histology) or may represent some part of the body of the human or animal in vivo. Generally, when the apparatus is used in vivo, the second end 1123b would be inserted into a cavity or passage of the human/animal body for internal examination. The second end 1123b would be moved into contact with a target such as tissue. Laser light suitable for causing a photoacoustic effect (e.g. pulsed or intensity-modulated continuous wave) is sent along the fibre 1123 to reach the second end 1123b (utilising the focusing process described above). Light is scattered and absorbed by the target, with a portion of the light generating ultrasonic waves 1174 by the photoacoustic effect (shown schematically at 1176). The ultrasonic waves propagate 1174 in all directions from the target, and so the ultrasonic detector 1122 can be positioned anywhere in or on the biological tissue 1172 providing the ultrasound waves can be detected. In FIG. 17 a first tip embodiment 1170 comprises a separate fibre 1123 (which, as in any embodiment described herein, may be a bundle of multi-mode fibres or a single multi-mode fibre) and ultrasonic detector 1122. As shown the fibre 1123 is within the biological tissue 1172 and the ultrasonic detector 1122 is external of the biological tissue 1172, but sonically coupled with it to facilitate detection ultrasonic waves.

In FIG. 17B a second tip embodiment 1180 comprises a fibre 1123 similar to FIG. 17A. However, in this embodiment, the ultrasonic detector 1122 comprises a piezoelectric transducer of diameter 12.7 mm that is mounted at the distal end of an electrical cable 1182, and adjacent the second end 1123b. The electrical cable 1182 is moveable in unison with the fibre 1123 (for example they may be provided within the same housing (not shown), or otherwise attached to one another) so that both the second end 1123b and the ultrasonic detector 1122 may be brought into proximity of the part of the biological tissue 1172 to be inspected. In use, the generation and processing of ultrasonic signals is the same as embodiments described above.

In FIG. 17C a third tip embodiment 1190 comprises a fibre 1123 similar to FIGS. 17A and 17B. However, in this embodiment, the ultrasonic detector 1122 comprises an optically transparent piezoelectric transducer having the same diameter as the optic fibre mounted at the second end 1123b of the fibre 1123. In some embodiments, this optically transparent piezoelectric transducer may comprise an active layer of polyvinylidene difluoride or lithium niobate with a transparent electrical conductive material coated on both sides served as the electrodes. An example of a suitable optically transparent piezoelectric transducer is described in Chen. H et al, "Optical-Resolution Photoacoustic Microscopy Using Transparent Ultrasound Transducer" 20 Sensors (2019) 19, no. 24: 5470, the contents of which is incorporated herein by reference. Electrical connections for the detector 1122 may be routed around the outside of the fibre 1123 and contained withing a sleeve (not shown). In use, the generation and processing of ultrasonic signals is the same as embodiments described above.

In FIG. 17D a fourth tip embodiment 1200 is similar to the second tip embodiment 1180 except that the electrical cable 1182 and detector 112 are replaced with a fibre optic ultrasound sensor 1202. An example of a suitable fibre optic ultrasound sensor is described in Guggenheim, James A., et al. "Ultrasensitive piano-concave optical microresonators for ultrasound sensing." Nature Photonics 11.11 (2017): 714-719, the contents of which is incorporated herein by reference. In use, the generation and processing of ultrasonic signals is the same as embodiments described above FIG. 18 is an embodiment of an apparatus 1210 which is generally similar to the embodiment of FIG. 15A when using a second end 1123h of the fibre 1123 as shown in FIG. 17. However, this embodiment provides a dual imaging modality: in addition to the photoacoustic imaging modality, there is a light detector 1212 (e.g. photodetector, photodiode, CCD camera) and a dichromatic beam splitter 1214 (or a beam splitter and wavelength filter) for provision of fluorescence microscopy. After characterising the fibre 1123 as described above, laser light can be focused 'pixel-by-pixel' over a particular area the biological tissue 1172 into which fluorophores (e.g. fluorescent dye) have been introduced (e.g. by injection). Longer wavelength photons produced by the fluorescence are directed by the dichromatic beam splitter 1214 to the photodetector 1212. By recording the fluorescence signal indicated by the photodetector 1212 at each pixel, an array of data can be compiled and this data processed to produce a fluorescence image of the target. At the same time, the ultrasonic detector 1122 can measure the ultrasound waves produced by the photoacoustic effect at the target, and be processed to produce an ultrasound image as described above. Different laser light may be used for photoacoustic and fluorescent signal excitation respectively.

Example Application: Optical Wireless Communication

Another application of the characterising and focusing process described above is optical wireless communication in free space which there is no line of sight between a transmitter and receiver, such as indoor optical wireless communication. In this application, data is transmitted using laser light at optical wavelengths in free space (e.g. through the air). In many situations there is no line of sight between the transmitter and receiver. If the light is directed at a surface (e.g. wall, ceiling) for reflection toward the receiver, reflection is diffuse and only a small portion of the transmitted laser light reaches the receiver. Furthermore, light that reaches the receiver has a time-varying speckle intensity pattern making high speed data transmission difficult or impossible owing to a poor signal to noise ratio.

Laser light may be reflected from one or more existing surface within buildings (e.g. walls, floors, ceilings, furniture) but, as mentioned above, these surfaces are types of disordered media and cause a high degree of scattering and diffuse reflection. By treating the communication link between the transmitter and receiver as the disordered media (similar to the diffuser 1020 in FIG. 10 and the multi-mode optical fibre 1123 in FIGS. 15A and B) the characterising process and focusing process may be performed to determine a focusing spatial modulation pattern to be used for that communication link. In this way, there is improved focus of light at the receiver with an increase in signal to noise ratio.

Figure 19:
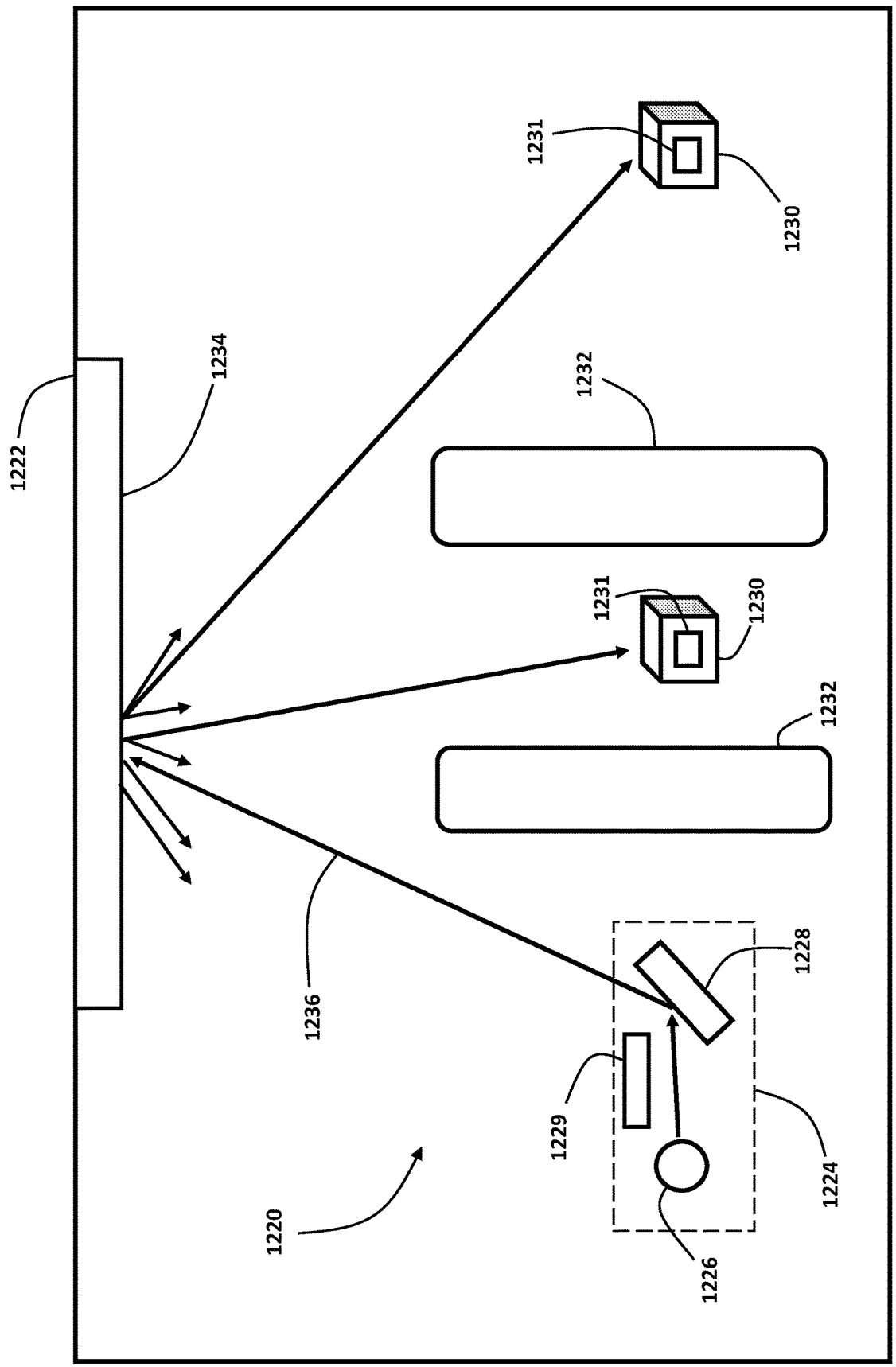
FIG. 19 is a schematic diagram of an apparatus for optical wireless communication according to the present invention.

FIG. 19 is a schematic diagram of an embodiment of a non-line-of-sight optical wireless communication system ('OWS') 1220 installed inside a building 1222. The building 1222 may be any structure in which a data communication system is useful. e.g. home, office, school, factory, shopping mall, airport, stadium, station, etc. The OWS 1220 may comprise a transmitter 1224 having a laser 1226, such as an external cavity laser, and a spatial light modulator ('SLM') 1228 such as a DMD, like the DMD described in embodiments above. Control of the laser 1226 and the SLM 1228 may be performed by a first computer 1229 (e.g. in the form of an ASIC). The OWS 1220 may further comprise one or more receiver 1230 which may be in the form of a CCD camera. CMOS or array of photodiodes. The receiver may comprise (or may be adapted to communicate with) a second computer 1231 for performing functions like the functions of the computer 1130 described above. Objects 1232 (e.g. furniture, building structures) within the building 1222 block line of sight communication between the transmitter 1224 and one or more of the receivers 1230. To overcome that, the SLM 1228 may be arranged to direct laser light toward a reflecting surface 1234 within the building. Generally the reflecting surface 1234 is a part of the building structure (such as a wall, floor or ceiling) is not a dedicated reflection device (e.g. mirror). As described above most such reflecting surfaces tend to produce a diffuse reflection of laser light. By reflecting laser light from an existing surface within the building 1222 fewer component parts are required for the OWS 1220 and it is easier to install and maintain.

Before the OWS 1220 is used to transmit data, the characterisation step (like that described in conjunction with FIG. 10) is performed to determine a focusing spatial modulation pattern for the SLM 1228 in order to improve the focus of light at the receiver 1230. In this case, the laser 1226 and SLM 1228 are controlled by the first computer 1129 to display the sequence of input patterns 1038, thereby characterising the communication link. The second computer 1231 may be adapted to process signals representing the light intensity at the receiver 1230 as each input image is displayed on the SLM 1228, and then utilise equation (19) above to determined the focusing spatial modulation pattern 1036 for the communication link. Once determined, the focusing spatial modulation pattern may be sent by the receiver 1230 to the transmitter using a different communication mechanism, such wireless (e.g WiFi), powerline, wired (e.g. Ethernet), and cellular. Once the transmitter 1024 has received the focusing spatial modulation pattern 1036 it may be stored and then displayed on the SLM 1228 and then data transmitted using the communication link. Once the focusing spatial modulation pattern is in use, there will be an improved focus of light at the receiver giving an increased light intensity and signal to noise ratio, and thereby improved data transmission. Since the characterisation step takes a comparatively short period of time (a few hundred milliseconds) may be that the first computer 1129 and the second computer 1130 are adapted to repeat the characterisation process periodically, non-periodically, under instruction of the user, and/or if the signal to noise ratio drops below a predetermined threshold.

Figure 20C:
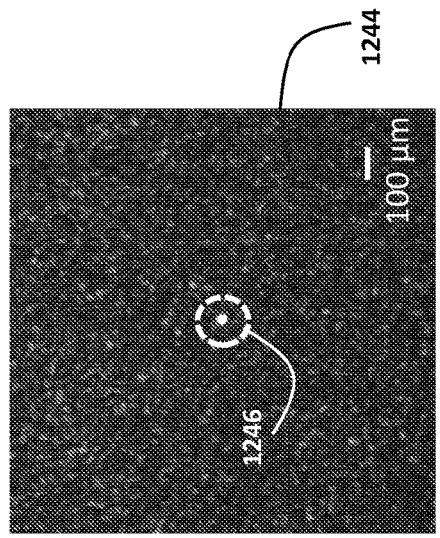
FIGS. 20A-20D are images obtained using the apparatus of FIG. 19, before spatial modulation of light and after spatial modulation of light.
Figure 20D:
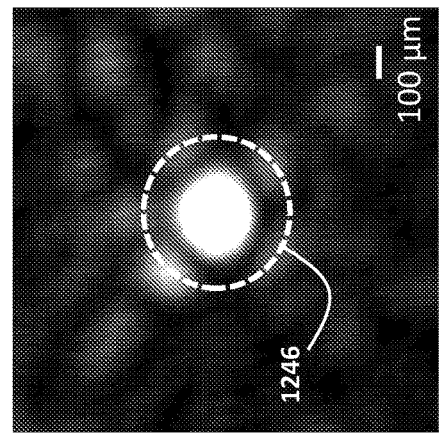
Figure 20A:
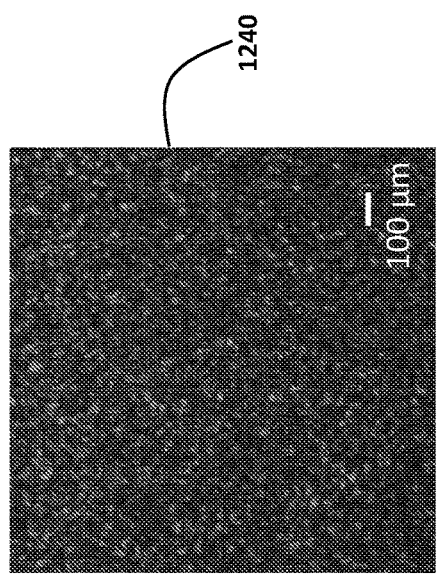
Figure 20B:
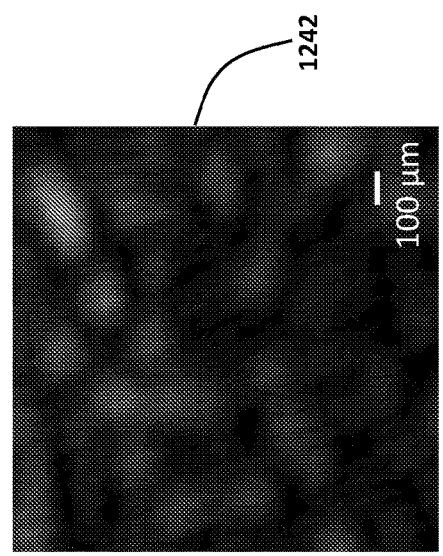

FIGS. 20A to 20D show results obtained in an experimental set up of an OWS like the OWS 1220. FIG. 20A is a reflected speckle pattern 1240 at the receiver 1230 when a random spatial modulation pattern was displayed by the spatial light modulator 1228. FIG. 20B is the light field 1242 captured by the receiver 1230 in free space at a distance of approximate 0.6 m from the reflecting surface, before a focusing spatial modulation pattern is determined (i.e. a random selection of ON/OFF mirrors on the DMD). FIG. 20C is a reflected speckle pattern 1244 showing a spot of light 1246 focused at the receiver 1230. FIG. 20D is the light field captured by the receiver 1230 in free space at a distance of approximate 0.6 m from the reflecting surface, after determination of a focusing spatial modulation pattern. As shown by these results, characterising the communication link enables the transmitter 1024 to improve the focus of light at the receiver 1230. Some advantages of improved focus include increasing the signal to noise ratio at the receiver 1230 and an increase in the length over which the communication link is functional.

Improving Peak to Background Ratio (PBR)

As described above, micromirrors of the DMD 1116 are switched 'ON' when the phase $\theta_n$ of the transmission constant $t_n$ is within the range $[\emptyset_R-\pi/2, \emptyset_R+\pi/2]$, where $\emptyset_R$ is the phase of the light field at the focusing pixel. This increases the intensity of light at the focusing pixel. Although increasing (or even maximising) the intensity at the focusing pixel is desirable, it does not necessarily indicate best performance. An alternative measure of the effectiveness of the focusing of light via a disordered medium in imaging applications is the so-called Peak to Background Ratio (PBR). PBR may be defined as the ratio of the maximum intensity of light at a focusing pixel to the average light intensity of the background (i.e. light received by pixels other than the focusing pixel). This measure takes account of both the light intensity at the focusing pixel and the background light intensity, so that maximum PBR does not necessarily coincide with maximum light intensity at the focusing pixel.

In particular, as each switched 'ON' micromirror also contributes to the background light intensity, some of the 'ON' micromirrors may contribute even more to the light intensity of the background than to that of the focusing pixel. Thus, the highest PBR, which largely determines the achievable signal-noise-ratio (SNR) in imaging applications, is not necessarily achieved by this modulation approach. As such, switching 'OFF' those micromirrors that contribute significantly to the background light intensity can lead to a higher PBR In the paper D. Wang. E. H. Zhou, J. Brake. H. Ruan, M. Jang. and C. Yang. "Focusing through dynamic tissue with millisecond digital optical phase conjugation." Optica 2, 728-735 (2015), it was shown that the ensemble average of the peak output intensity with binary modulations using a DMD can be expressed as:

$$I_p = 2NA^2\sigma^2\left(\frac{\sin\left(\frac{2\varphi}{2}\right)+\varphi}{2\pi}\right) + \frac{\pi}{2}N(N-1)A^2\sigma^2\left(\frac{\sin\varphi}{\pi}\right)^2 \quad (23)$$

in which the transmission constants $t_{mn}$ are assumed to obey a Rayleigh distribution and $|t_{mn}|^2$ follows an exponential distribution $|t_{mn}|^2 \sim e^{-1/2\sigma^2}$ with $2\sigma^2$ as the ensemble average intensity of each element, $\varphi$ is the upper bound of the absolute phase difference: $0 \leq \Delta 527 \leq \varphi$, and N is the total number of input micromirrors, and A is the amplitude of the incident light field at each DMD mirror. The average background light intensity is expressed as:

$$I_p = 2NA^2\sigma^2\frac{\varphi}{\pi} \quad (24)$$

It can be shown that PBR can be determined as follows:

$$PBR = \frac{I_p}{I_b} \approx \frac{N\sin^2\varphi}{4\varphi} \quad (25)$$

Equation (23) indicates that the maximum light intensity at the focusing pixel occurs when $\varphi=\pi/2$, whilst equation (25) indicates that PBR is a function of the absolute phase difference $\varphi$. In fact it was shown in the Wang paper that PBR can be maximised when $\varphi=0.371\pi$, although the Wang paper only considered phase information for producing a DMD pattern that maximised the PBR.

We have discovered that in some embodiments the PBR of the focusing spatial modulation pattern may be further improved by identifying those transmission constants $t_n$ from the matrix $RVITM_{PA}$ with the highest real number values, and then switching ON the corresponding mirrors of the DMD (and leaving all other mirrors OFF). Furthermore, we have discovered that in some embodiments transmission constants $t_n$ meeting this criterion can be identified as a top percentage or a top fraction of the all the transmission constants in the matrix $RVITM_{PA}$. For example, it may be that the transmission constants $t_n$ in the matrix $RVITM_{PA}$ with real number values lying within the top 30% are identified and the corresponding mirrors switched ON. Not only is there an improvement in the PBR, but the improvement may be achieved quickly compared to other methods, as will be explained below.

Referring again to FIG. 11, in order to implement this aspect of the invention optional step S11-5b may be performed. Once the matrix $RVITM_{PA}$ has been generated at step 11-5, the computer 1030 proceeds to step S11-5b in which the matrix $RVITM_{PA}$ is processed to identify n % of transmission constants with the highest real number values in the matrix (the percentage being of all the transmission constants in the matrix including positive and negative values, and where positive values are considered higher or greater than negative values). In one embodiment n % may be about 30% (although other percentages are envisaged as described below) Once those transmission constants have been identified the computer 1030 proceeds to step S11-6 in which the focusing spatial modulation pattern is generated. To do that, the computer 1030 takes the top n % of transmission constants and may generate a new matrix which represents all of the ON/OFF state of the mirrors of the DMD 1016. The matrix values are set so that mirrors are ON corresponding to the top n % of transmission constants, and OFF otherwise. This new matrix could contain only binary values e.g. +1 or −1, or +1 or 0 for that purpose. The new matrix is then used as the focusing spatial modulation pattern to be sent to the transmitter in step S11-7. It should be clear that the two methods that can be performed by the computer 1030 as illustrated in FIG. 11 will result in different focusing spatial modulation patterns sent to the transmitter. In particular, performing step S11-5 then S11-6 will generate a different focusing spatial modulation pattern than performing step S11-5, step S11-5b and then step S11-6.

In order to demonstrate the improvement in PBR by generating the focusing spatial modulation pattern in this way, it was compared to a number of other DMD-based non-holographic algorithms that function to improve PBR. These other techniques, and an explanation of their implementation (both numerical simulation and experiment), are as follows:

(A) Real-Valued Intensity Transmission Matric (RVITM) Algorithm

This algorithm is as described herein, for example with reference to FIG. 11. Results are presented below covering the two options in FIG. 11, i.e. without step S11-5b and with step S11-5b.

(B) Estimated TM-Based Algorithm (ETA) This algorithm is described in A. Drémeau. A. Liutkus, D. Martina, O. Katz, C. Schülke, F. Krzakala, S. Gigan, and L. Daudet. "Reference-less measurement of the transmission matrix of a highly scattering material using a dmd and phase retrieval techniques," Opt. express 23, 11898-11911 (2015), and the algorithm. The algorithm was used for transmission matrix (TM) estimation and light focusing through a MMF. A total number of 6N random binary patterns with 50% micromirrors 'ON' were displayed on a DMD whilst the speckle intensities behind the MMF were captured by a camera. A Bayesian phase retrieval algorithm (described in A. Drémeau and F. Krzakala. "Phase recovery from a bayesian point of view: the variational approach," in 2015 *IEEE International Conference on Acoustics, Speech and Signal Processing (ICASSP)*. (IEEE, 2015). pp. 3661-3665)] was then used to calculate the complex-valued TM from intensity-only input and output pairs via iterative optimizations. This algorithm was chosen as it benefits from a moderate computational cost. An open-source script of the phase retrieval algorithm described in the Drémeau paper was used in this work. As this algorithm provides phase values of a row of the TM corresponding to the $m_{th}$ output mode, optimal DMD patterns with both $Re(t_{mn}>0)$ and $|arg(t_{mn})|<0.371\pi$ were used for focusing and their performance were compared.

(C) Conditional Probability-Based Algorithm (CPA)

The CPA is described in detail in T. Zhao. L. Deng, W. Wang, D. S. Elson, and L. Su, "Bayes' theorem-based binary algorithm for fast reference-less calibration of a multimode fiber," Opt. express 26.20368-20378 (2018). Like the ETA, a total number of 6N random binary patterns were used as inputs, whilst the intensities of speckles at output of a MMF were captured. There were three steps involved in the generation of an input DMD pattern for focusing. First, an intensity threshold was used to divide the output intensities into two groups: a 'focusing' and a 'non-focusing' group. Second, Bayes' theorem was used to calculate the conditional probability that switching 'ON' each micromirror leads to light focusing at the target output position ('focusing' group). Finally, a threshold was used to produce the optimal DMD pattern for light focusing through the MMF by switching 'ON' micromirrors a conditional probability higher than a threshold. As reported in the Zhao paper to maximise the PBR a first threshold was set as the 80 percentile of all intensities at the target position, while a second threshold was set as the median value of all probability values.

(D) Genetic Algorithm (GA)

The method for implementing the GA for light focusing through a diffuser was described in D. B. Conkey, A. N. Brown, A. M. Caravaca-Aguirre, and R. Piestun, "Genetic algorithm optimization for focusing through turbid media in noisy environments." Opt. express 20, 48404849 (2012) and in X. Zhang and P. Kner, "Binary wavefront optimization using a genetic algorithm," J. Opt. 16, 125704 (2014). We used the same process but employ the PBR of the output light field as the feedback to be maximised. First, a total number of 20 random binary patterns with approximate 50% micromirrors 'ON' were used as the 1BC generation population. Each DMD pattern is considered as the chromosome of an individual, and the status of a micromirror was considered to be a chromosome code ('1' for 'ON' and '0' for 'OFF'). Output speckles intensities were recorded when displaying these binary patterns on a DMD and their PBR values were compared. Individuals in the 1BC generation population were ranked according to their corresponding PBRs in the outputs. Then individuals with larger PBRs were assigned larger probabilities to be selected as parents to produce the next generation population by crossing the parent chromosomes with a constant cross rate. Mutation was also introduced by randomly switching a small number of chromosome codes with a mutate rate to avoid locally optimal solutions. In the next step, the new generation was ranked according to the resulting PBRs and produced the next generation patterns through the aforementioned progress. After a large number of iterations, the chromosome codes leading to a high PBR were saved in a DMD pattern. In our numerical simulations, 30,000 generations were implemented with the cross rate setting to be 0.6 and the mutate rate 0.02. In our experiments, 4.000 generations were implemented, the mutate rate was set to be $0.1*e^{-G/600}+0.02$ to speed up the optimisation, where G is the index of the generation.

Numerical simulations were implemented in MATLAB to investigate the performance of different algorithms (A)-(D). A complex-valued simulated TM was generated with random phases and amplitudes following a uniform and a Rayleigh probability density function between 0 and $2\pi$, and 0 and 1, respectively. The number of input micromirrors (N) was set to be 32×32 while the number of output pixels M was set to be 64×64. Output light intensities were calculated based on the simulated TM via $E_m = |\Sigma_{n=1}^{N} t_{mn} E_n|^2$, which were fed to those algorithms for comparison. The resulting PBR was calculated as the ratio of the intensity at the focusing pixel over the average intensity in the background, for the evaluation and comparison of the focusing performance with different algorithms.

Numerical Simulation

Numerical simulations were performed with a MATLAB program. In order to generate the output speckle patterns 134, a complex-valued transmission matrix (TM) with 8192 output pixels and 1024 input pixels was generated. The phases and amplitudes of the TM were randomly generated to obey uniform and Gaussian distributions between 0 and $2\pi$, and 0 and 1, respectively. The TM can be used as a ground truth (or reference TM) for comparison with results achieved with DMD-based algorithms. As the TM elements follow a circular Gaussian distribution with phases obeying a uniform distribution in $[-\pi, \pi]$, modulating phases of output light fields coming from all input modes to an ideal phase $\emptyset=0$ or to $\emptyset=\emptyset_R$ leads to approximately the same constructive interference at the output position. For the case of comparison with the RVITM algorithm which employs $\emptyset_R$ as the ideal phase, the focusing condition was chosen as $\theta_{mn}-\emptyset_R<\varphi$ rather than $|\theta_{mn}|<\varphi$. Both $\varphi=\pi/2$ and $\varphi=0.371\pi$ were used as the upper boundary for producing the DMD pattern to focus light in the complex-valued TM-based approaches.

Experimental Setup

The experimental setup was very similar to the apparatus of FIG. 15A (except a data communication system 1140 was not required). The light source was a collimated diode-pumped solid-state laser module (532 nm, 4.5 mW, CPS532. Thorlabs. New Jersey. USA). After beam expansion through two tube lenses (AC254-030-A-ML; AC254-075-A-ML, Thorlabs, New Jersey. USA), the light was spatially modulated using a DMD (DLP7000, 768×1080 pixels, Texas Instruments. Texas. USA) and then projected onto the proximal tip of a MMF (105 µm, 0.22 NA, 1 m. M43L01, Thorlabs, New Jersey. USA) via a tube lens (AC254-050-A-ML. Thorlabs. New Jersey. USA) and an objective (20×, 0.4 NA. RMS20X, Thorlabs, New Jersey. USA). The light illuminated area on the DMD included 32×32 independent micromirrors. An objective (20×, 0.4 NA. RMS20X. Thorlabs. New Jersey, USA) and a tube lens (AC254-0100-A-ML. Thorlabs. New Jersey. USA) were used to magnify the output light beam before it was captured by a complementary metal-oxide-semiconductor (CMOS) camera (C11440-22CU01. Hamamatsu Photonics. Shizuoka. Japan) with a frame rate of 200 frames per second (fps) for MMF characterisation.

Results

Figure 21A:
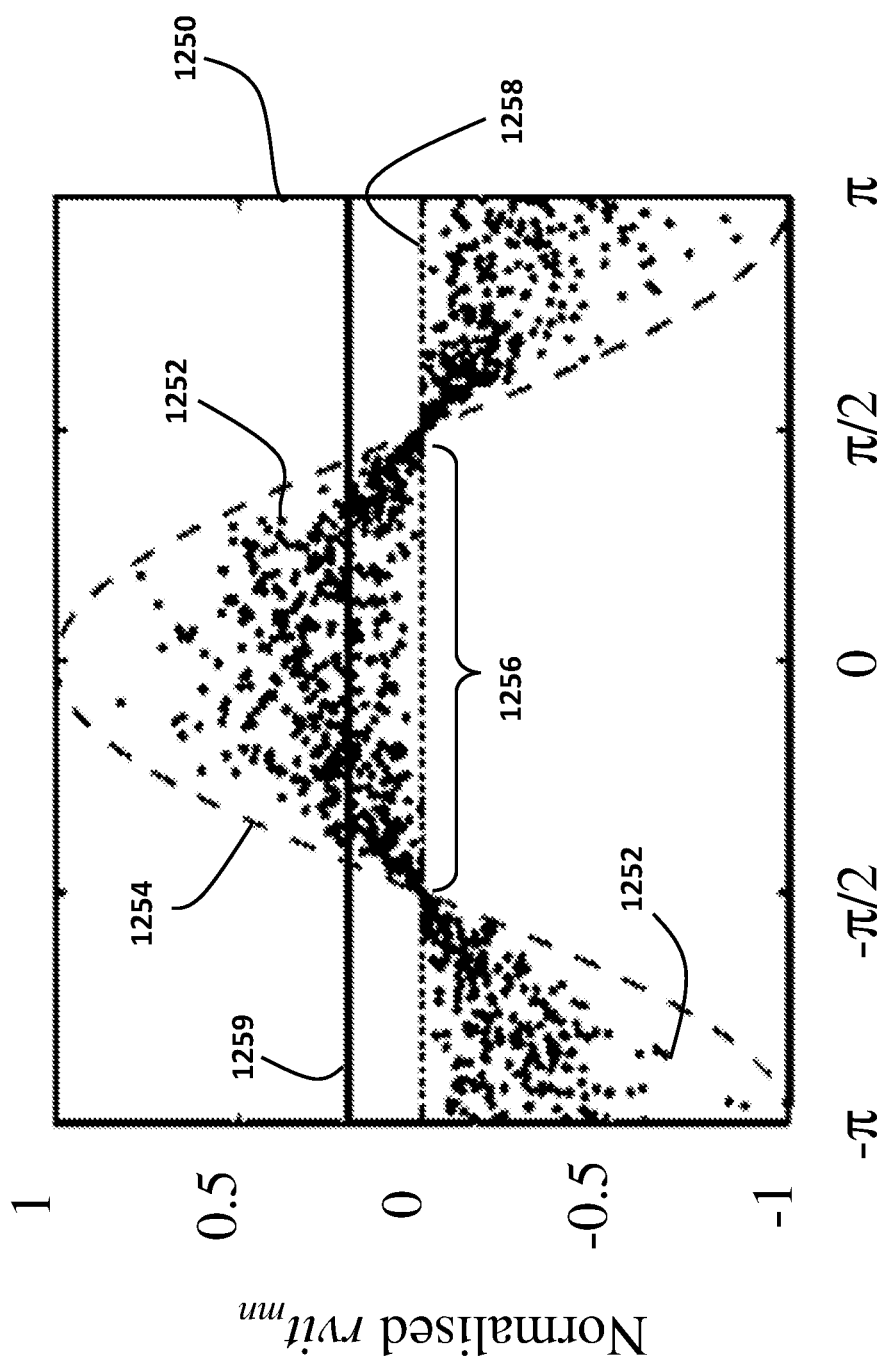
FIG. 21A is a graph of phase difference versus real number value of transmission constants determined by a method according to the present invention.

In the RVITM-based algorithm (A), each micromirror has a respective phase difference ($\theta_{mn}-\emptyset_R$) and a transmission constant ($rvit_{mn}$). FIG. 21A shows a graph 1250 of phase difference versus the normalised value of the transmission constants $rvit_{mn}$ 1252 obtained via equation (22) for each micromirror in the numerical simulations. The distribution of the transmission constants $rvit_{mn}$ for different phases differences has an envelope of a cosine function 1254. As the phases of the transmission constants $rvit_{mn}$ obey a uniform distribution in $[-\pi, \pi]$, half of the transmission constants $rvit_{mn}$ 1256 have positive values and their corresponding phase differences ($\theta_{mn}-\emptyset_R$) are in the range of $[-\pi/2, \pi/2]$. So, switching 'ON' the corresponding micromirrors leads to a linear sum of the transmission constants $rvit_{mn}$ 1256 with the constructive interference at the target output position and hence produces the light focusing. To further improve the PBR (FIG. 11, step S11-5b), all values of the transmission constants $rvit_{mn}$ 1252 were ranked in descending order according to real number value, different proportions (P) of total number of the transmission constants $rvit_{mn}$ with larger values were selected, the corresponding micromirrors were switched 'ON', and then the resulting PBR determined. By selecting a group of micromirrors with the highest real number values of the transmission constants $rvit_{mn}$ 1252, not only is the phase difference of each micromirror taken into account, but also the amplitude contributed to the PBR by each micromirror at the target. In some embodiments this may result in a different selection of micromirrors than using phase difference only, the different selection producing an improved PBR compared to the selection by phase only.

Figure 21B:
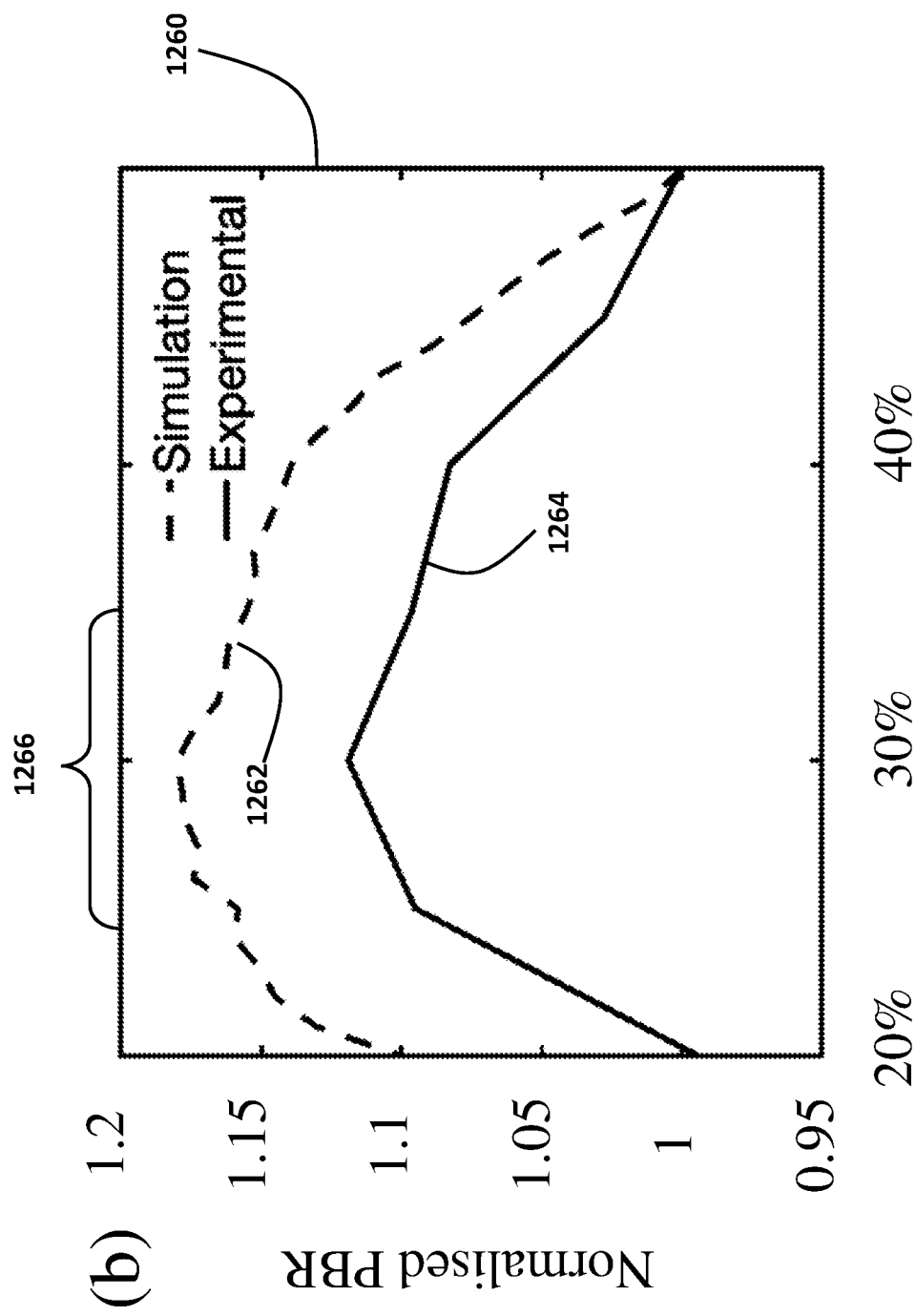
FIG. 21B is a graph of simulation and experimental results of percentage of ON mirrors of a DMD versus normalised peak-to-background ratio (PBR), focused on a small percentage range of ON mirrors near maximum PBR.

FIG. 21B shows a graph 1260 of the proportion of ON micromirrors P versus normalised PBR. A first line 1262 shows the results obtained by simulation and a second line 1264 shows the results obtained by experiment. For example, when P=50% the micromirrors with transmission constants $rvit_{mn}$ above a first threshold 1258 (see FIG. 21A) of $rvit_{mn}=0$ are switched 'ON'. When P=30% the micromirrors with transmission constants $rvit_{mn}$ above a second threshold 1259 (see FIG. 21A) of $rvit_{mn}=0$ are switched 'ON'.

Figure 21C:
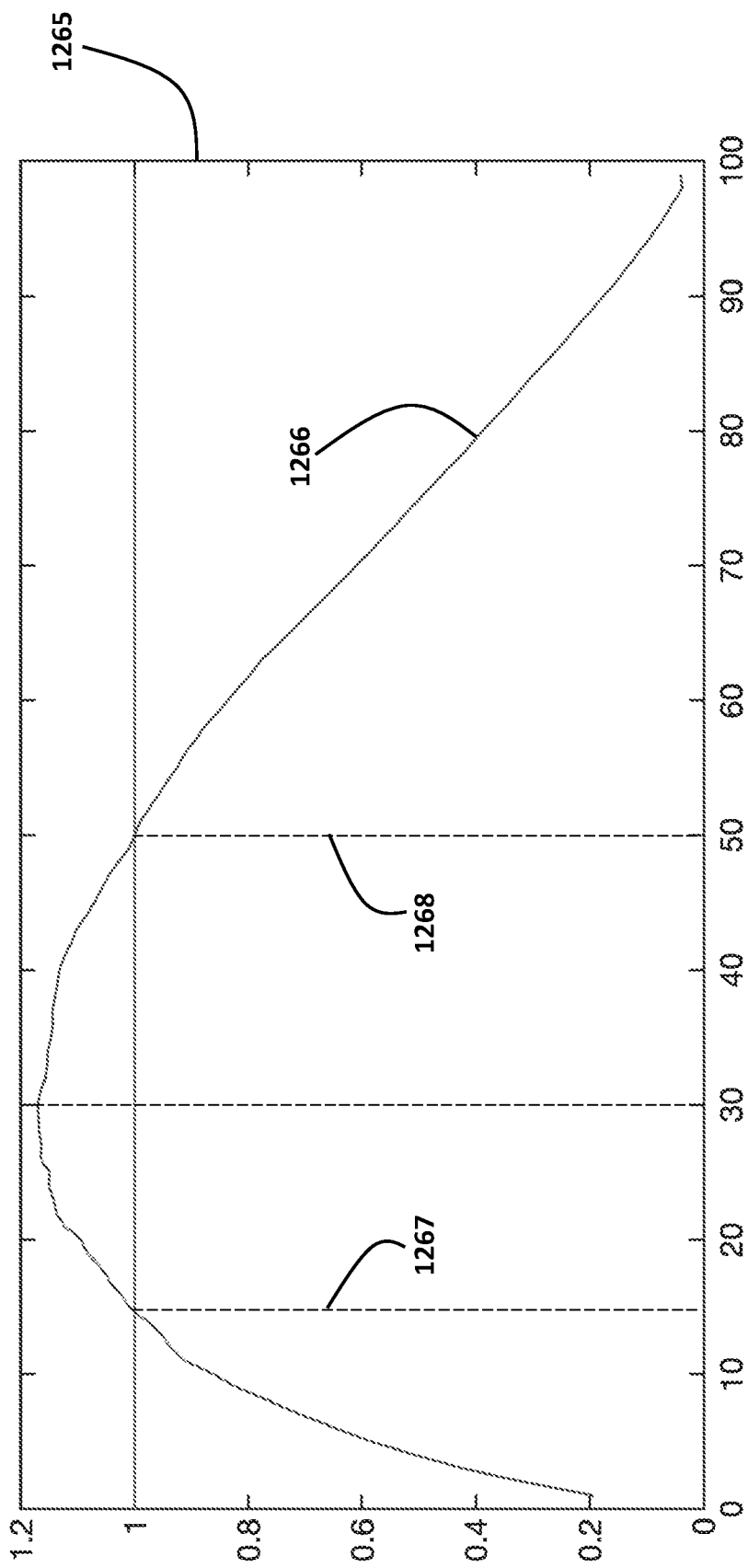
FIG. 21C is a graph of simulation results of percentage of ON mirrors of a DMD versus normalised PBR, showing the full percentage range.

As seen in FIG. 21B with both experiments and simulations the PBR was greater than one over the approximate range 20%≤P≤50%. In other words, switching 'ON' micromirrors with transmission constants $rvit_{mn}$ distributed in the dome region above the second threshold 1259 and below the cosine function 1254 in FIG. 21A produced the maximum PBR with the RVITM-based algorithm. To investigate the maximum range of P for which the PBR is greater than one, reference is made to FIG. 21C which shows the results of numerical simulations. In particular a graph 1265 shows a line 1266 indicating variation of PBR with P. Lines 1267 and 1268 show the values of P for which PBR is greater than one, namely about 15%≤P≤50% (all figures ±1%). In practice it may be that the precise percentage range is slightly different to this range, but the experimental data of FIG. 21B indicates this range is broadly justified. In some embodiments it is envisaged that the number of ON micromirrors having the greatest real-valued transmission constants $rvit_{mn}$ may be selected to fall within any one of the following ranges: 15%≤P≤50%, 20%≤P≤45%, 22%≤P≤40%, 25%≤P≤35%, 25%≤P≤33%, and 29%≤P≤31%. In some embodiments maximum PBR can be obtained by switching ON the 30% of micromirrors having the highest real-numbered transmission constants. In some embodiments, it may be desirable to increase both intensity of light at the target and improve the PBR. That can be achieved by selecting a percentage of ON micromirrors between the peak PBR value (indicated by line 1269) and highest percentage of micromirrors where PBR is equal to one (indicated by line 1268). In an embodiment that range is 30%≤P≤50%. In other embodiments it is envisaged that the number of ON micromirrors having the greatest real-valued transmission constants $rvit_{mn}$ may be selected to fall within any one of the following ranges: 30%≤P≤45%, 30%≤P≤40%, 30%≤P≤35%, 30%≤P≤33%, and 30%≤P≤31%.

One advantage of at least some methods according to the invention is that selecting micromirrors to switch ON according to the real number value of a real-valued transmission constant means that micromirrors are selected based on both amplitude and phase difference (of the corresponding complex-valued transmission matrix), rather than just phase difference only. This produces a different percentage of ON micromirrors than the same percentage of ON micromirror selected by phase difference only for example.

FIG. 22 is a table showing a performance comparison of the algorithms (A)-(D). The notes to the table are as follows:
 a, b with reference TM and estimated TM, the PBR refers to two different conditions for determining the patterns for focusing: |arg $(t_{mn})$|<π/2 (top) and |arg $(t_{mn})$|<0.371π(bottom).
 c in RVITM (D), the PBR refers to P=50% (top) and P=30% (bottom).
 S simulations
 E experiments
 d in experiments, the time cost includes the time for DMD pattern display during the fibre characterisation and the computation time for producing the optimal DMD patterns, while in simulations, only the latter was included in the time cost.

Figures 23A, 23B:
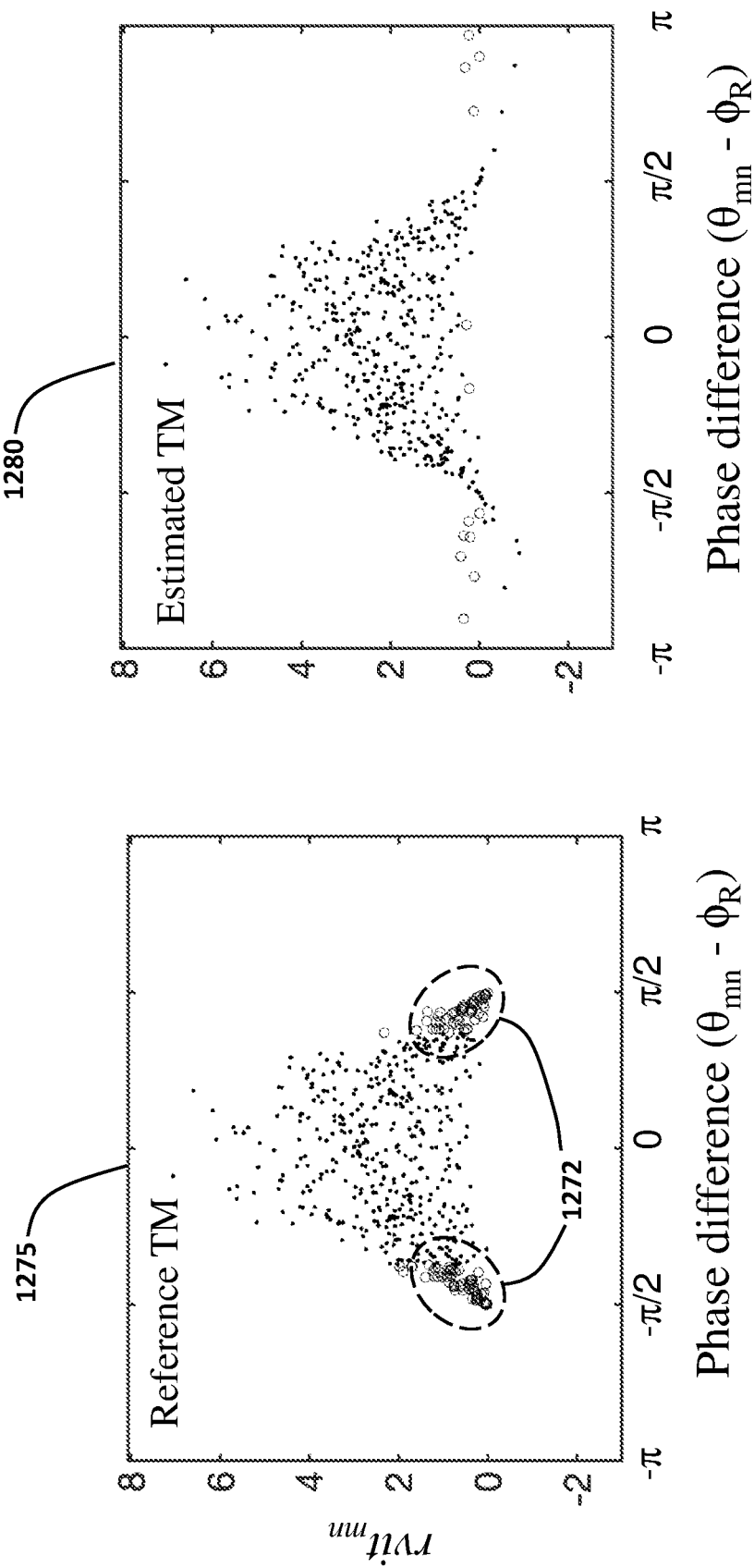
FIGS. 23A-23E are graph of phase difference versus real number value of transmission constants determined according to the different algorithms of FIG. 22.
Figures 23C, 23D:
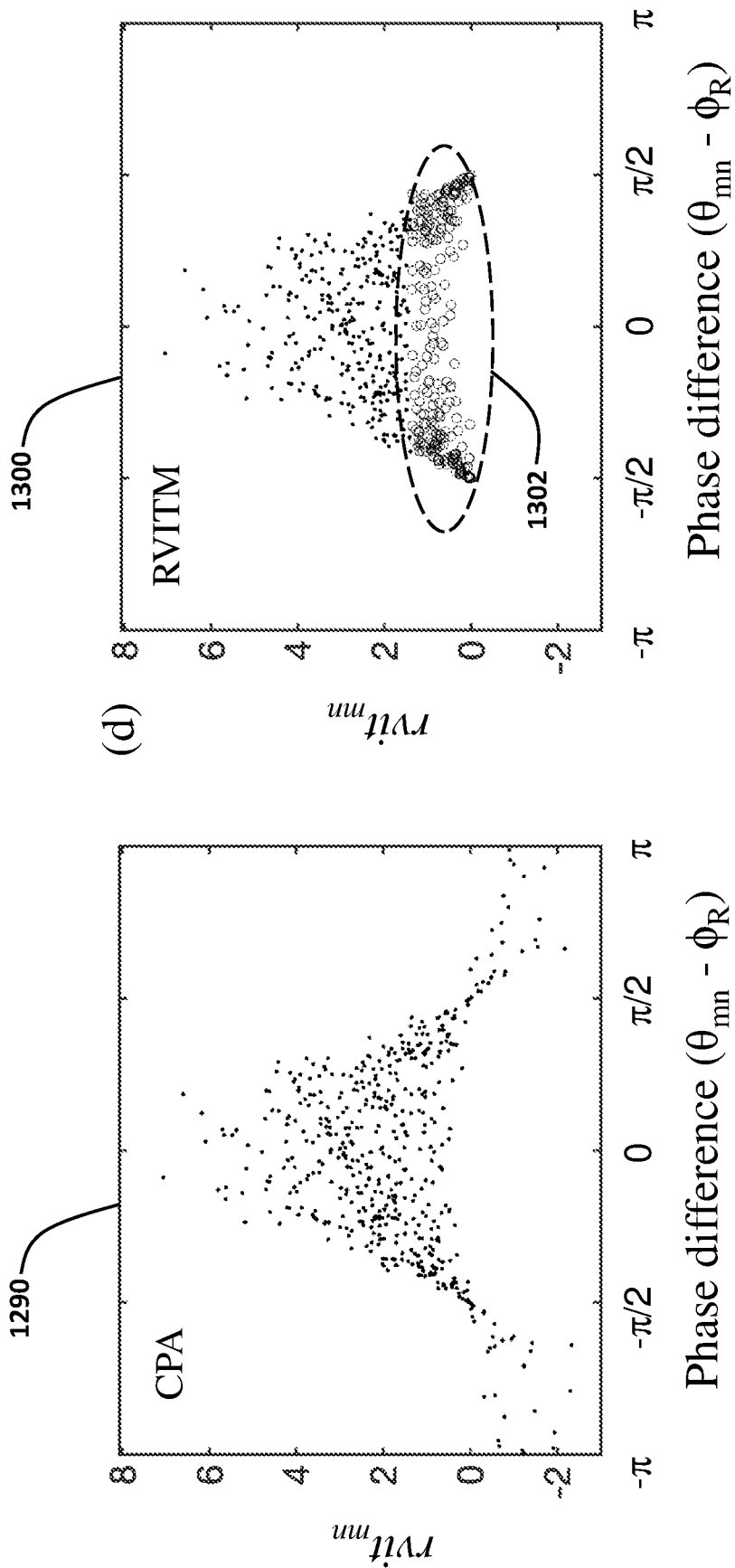
Figure 23F:
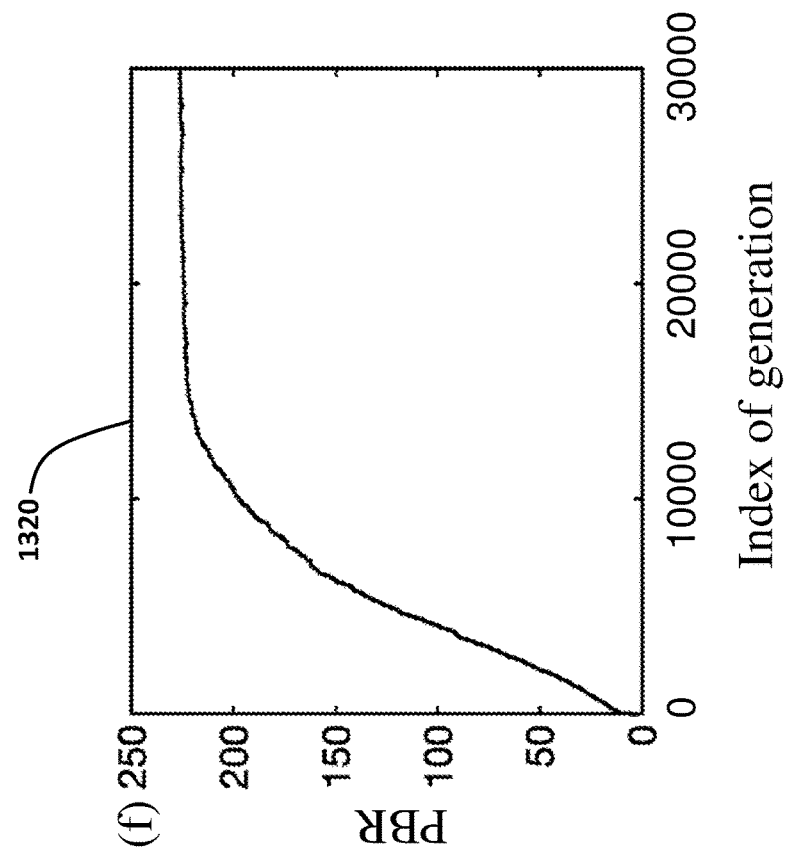
FIG. 23F is a graph of index of generation versus PBR for the genetic algorithm (GA) of FIG. 22.

For the ease of comparison, the $rvit_{mn}$ and $θ_{mn}-Ø_R$ values were calculated for all micromirrors using the ground truth TM (described above in conjunction with the numerical simulation), whilst those corresponding to the switched 'ON' micromirrors determined by the different algorithms am shown in FIGS. 23A-23F. FIGS. 23A-23E shows a graphs 1275, 1280, 1290, 1300 and 1310 respectively of phase difference versus the values of the transmission constants $rvit_{mn}$. FIG. 23F is a graph 1320 of index of generation versus PBR for the genetic algorithm (D) as will described in the following. In the case of the ground truth (or reference) TM graph 1275, all of the data points represent micromirrors that were switched 'ON' corresponding to values of $rvit_{mn}$ above the first threshold 1258 of $rvit_{mn}$=0. i.e. a phase difference φ in the range [−π/2, +π/2]. Data points shown with open circle symbols in regions 1272 represent additional micromirrors that were switched 'OFF' when the second threshold 1259 was used. i.e. the phase difference φ in the range [−0.371π, +0.371π]. Referring to the table shown in FIG. 22 a PBR value of 208.4 was achieved in the latter case, which is 13.9% higher than a PBR value of 183.0 achieved in the former case.

Still referring to the table in FIG. 22 the PBR values achieved with the ETA (B) were slightly smaller than that achieved with the reference TM (170.4 for phase difference φ in the range [−π/2, +π/2] and 190.3 for phase difference φ in the range [−0.371π, +0.371π], respectively). This slight reduction of PBR values can be attributed to the errors of the TM calculation, which is indicated by the different micromirrors chosen as shown by the $rvit_{mn}$ values in FIG. 23B.

The CPA (C) produced lower PBR of 156.7 compared to the estimated TM method (see also FIG. 23C).

With the RVITM algorithm (A), the first scenario with $rvit_{mn}$ values above the first threshold 1258 (i.e. P=50% and a phase difference φ in the range [−π/2, +π/2]) resulted in the same DMD pattern (as represented by all of the data points in FIG. 23D) for light focusing as that obtained from the reference TM and hence the same PBR value of 183.0. In the second scenario when the second threshold 1259 was applied (i.e. P=30% and phase difference φ in the range [−0.371π, +0.371π]), those micromirrors that are represented by lighter shaded data points in the region 1302 were switched 'OFF', and the PBR value increased to 228.2, which is even higher than that achieved with the reference TM with phase difference φ in the range [−0.371π, +0.371π] (PBR=208.4).

Figure 23E:
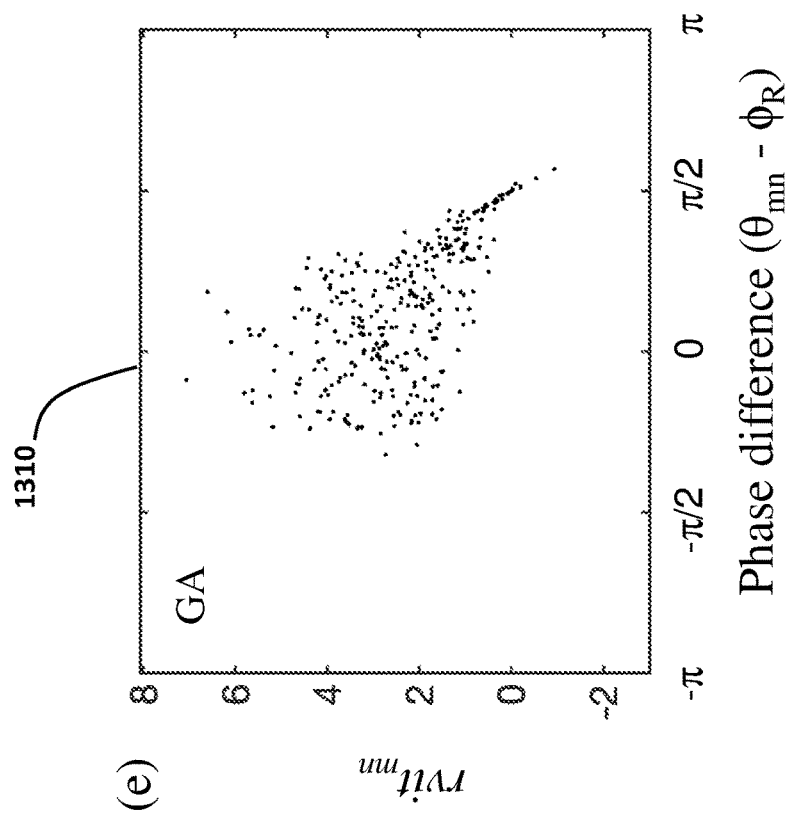

The PBR value achieved with the GA (D) reached the highest value of 239.7 among all the algorithms but after the evolution of 30,000 iterations (see FIGS. 23E and 23F).

To compare the focusing speed of different methods, the average times taken for different methods to compute an optimal DMD pattern for focusing over 100 output locations (e.g. different pixels of a CCD) were obtained on a PC with 2.3 GHz Dual-Core Intel Core 15 (see the table in FIG. 22). Although providing the highest PBR, the GA (D) had the longest computation time of 400 s. In comparison, with 200 iterations the computation time for the ETA (B) and the CPA (C) was 15 s and 4 s, respectively. The RVITM-based algorithm (A) calculated the $rvit_{mn}$ values for all output positions at the same time (i.e. in parallel), while for each output position the computation time for focusing was 7.5 ms.

Performance Comparison in Experiments

Figure 24A:
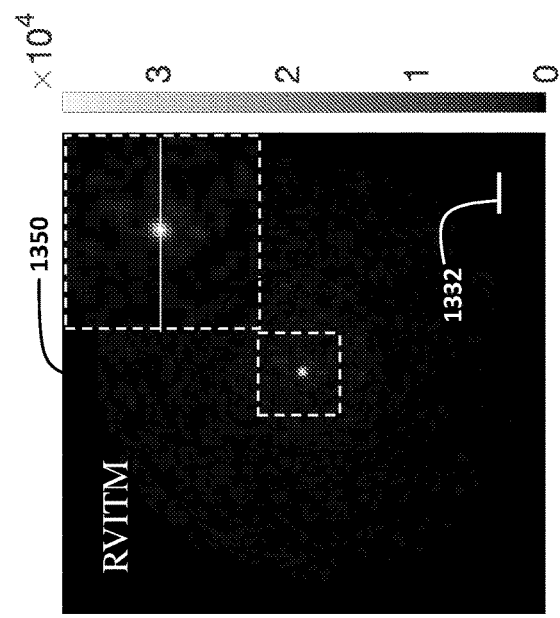
FIGS. 24A-24D are images of focal spots obtained by the algorithms of FIG. 22.
Figure 24C:
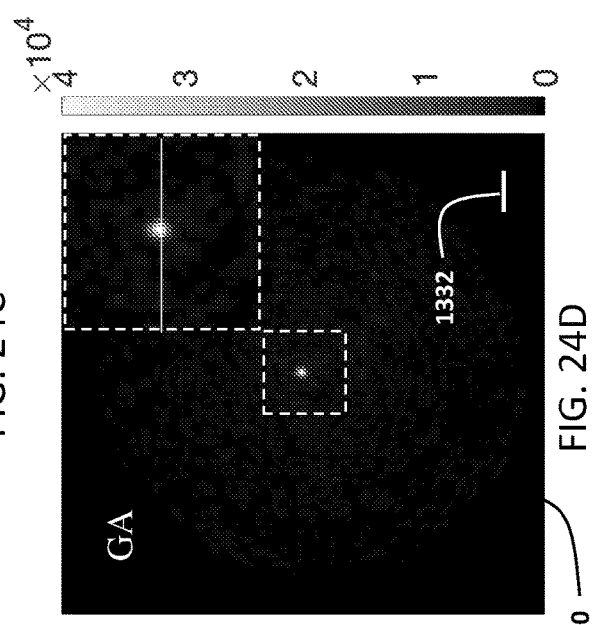
Figure 24B:
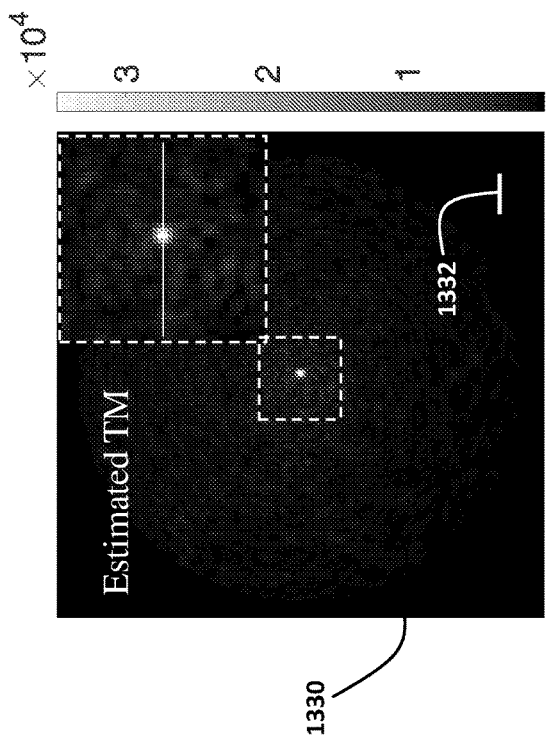
Figure 24D:
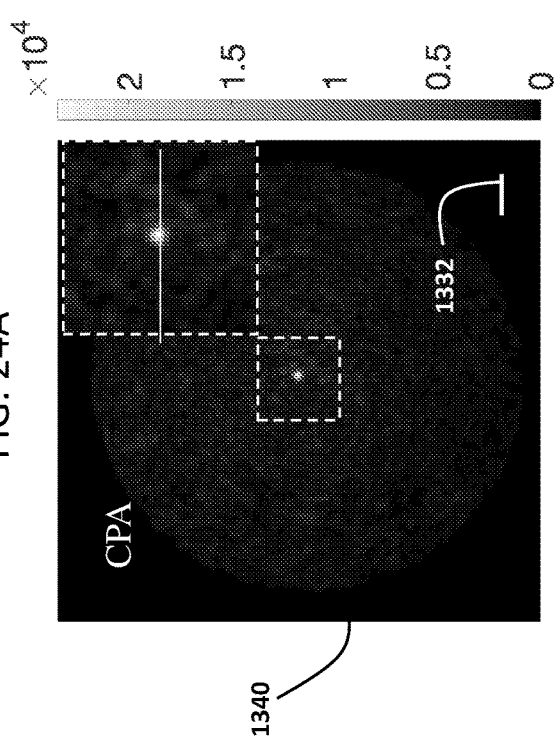
Figure 24F:
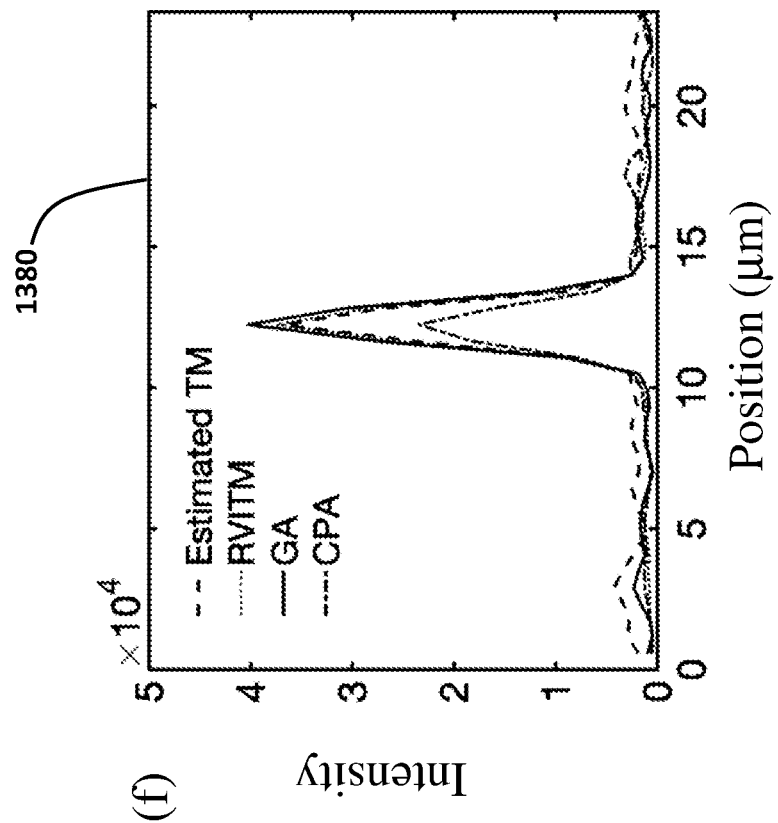
FIG. 24F is a graph of position versus intensity for the focal spots of FIGS. 24A-24D.
Figure 24E:
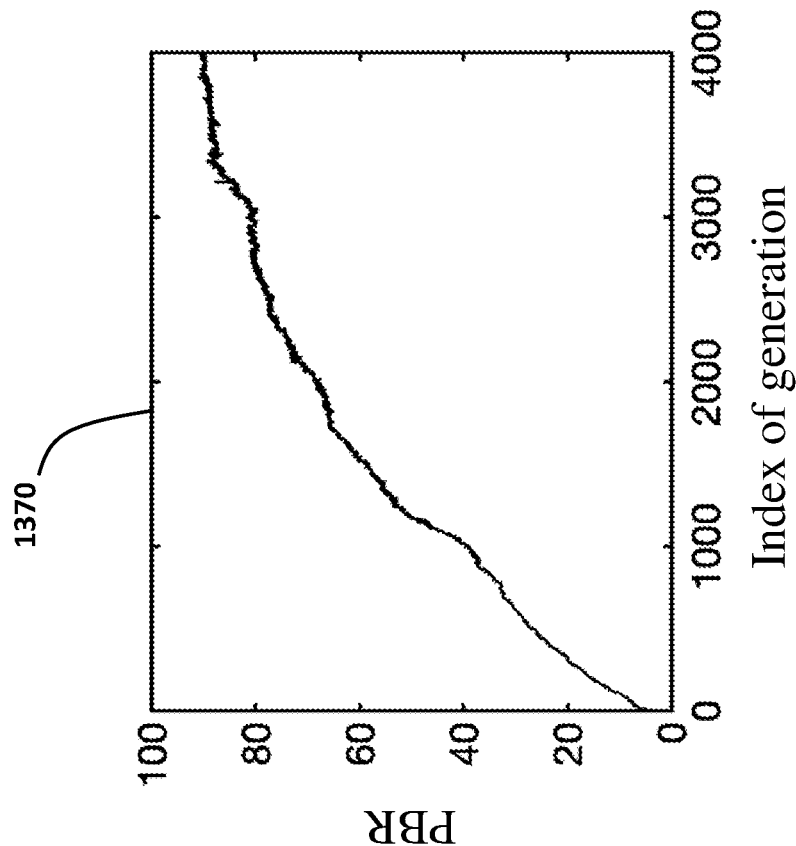
FIG. 24E is a graph of index of generation versus PBR for the genetic algorithm (GA) of FIG. 22.

FIGS. 24A-24D FIG. 5 are plots 1330, 1340, 1350 and 1360 respectively of the output light intensity patterns of an optical focus generated at the distal end of the MMF using algorithms (A)-(D). The scale bars 1332 represent a dimension of 10 µm. Referring again to FIG. 22 the PBR of the ETA (B) was estimated to be 58.5 when switching 'ON' micromirrors with $Re(t_{mn})$ >0, and increased to 64.2 with |arg$(t_{mn})$|>0.371π. The PBR achieved with the CPA (C) was the lowest, the GA (D) produced the largest PBR of 91 among all the algorithms after 4000 iterations (see FIGS. 24D and 24E, the latter being a graph 1370 showing index of generation versus PBR). The relationship between the achieved PBR and the proportion of micromirrors P with the RVITM-based algorithm (A) is shown and described above with reference to FIG. 21B. The highest PBR value of 89.4 was reached at P=30% (with the output light intensity shown in FIG. 24C) compared to a PBR of 79.9 at P=50%. The profiles of foci are shown in FIG. 24F which is a graph of position (or distance) versus intensity (in arbitrary units). The focus achieved with different methods has a uniform diameter of 1.7 µm. Unlike the results obtained in the numerical simulation, the time cost in experiments includes the time for DMD pattern display. As a result, the GA (D) had the longest time of 2.2 h, while the time cost was 46 s, 36 s and 10.3 s for the ETA (B). CPA (C) and the RVITM (A) algorithms, including both input pattern display and data processing run-times.

In summary embodiments of the invention can improve the PBR obtained with the ETA (B) by switching 'ON' a group of micromirrors for which the corresponding real-valued transmission constants have the highest real number values and leaving 'OFF' the remaining micromirrors (i.e. those with lower values). The PBR in such embodiments is improved compared to PBR achieved with the commonly used criteria |arg($t_{mn}$)|>π/2 for DMD-based waveform shaping. With the RVITM-based algorithm (A), the maximum PBR was achieved at P=30%, although it is noted that various ranges of P around this value are expected to produce similar results. Although the precise phase values are not achievable with RVITM (A), we have found that the transmission constants $rvit_{mn}$ encode (or represent) phase and amplitude information. This enables a higher PBR than that of the ETA (B). Similarly, the higher PBR achieved with the RVITM algorithm (A) also suggests that the amplitude information should be considered for achieving the maximum PBR with a DMD. The GA (D), which does not require the phase and amplitude information of the TM as prior knowledge, achieved the highest PBR via a large number of iterations as expected but with a high time cost. Interestingly, a small number of micromirrors with negative $rvit_{mn}$ were switched 'ON' with the GA for focusing (see FIG. 23E). This indicates that although these micromirrors had negative contributions to light intensity at the focusing position, they have substantially reduced the intensity of the background, leading to a higher PBR compared to those methods considering only micromirrors with positive $rvit_{mn}$ (see FIGS. 23A, 23B, 23D). To further increase the PBR, more independent micromirrors could be used in the future, however, at the expense of the focusing time.

Embodiments of the invention using employing improved PBR may be used in (but not limited to) any of the embodiments and applications described with reference to FIGS. 10, 15A, 15B, 17A-D, 18, 19 and 25 (described below).

Figure 25B:
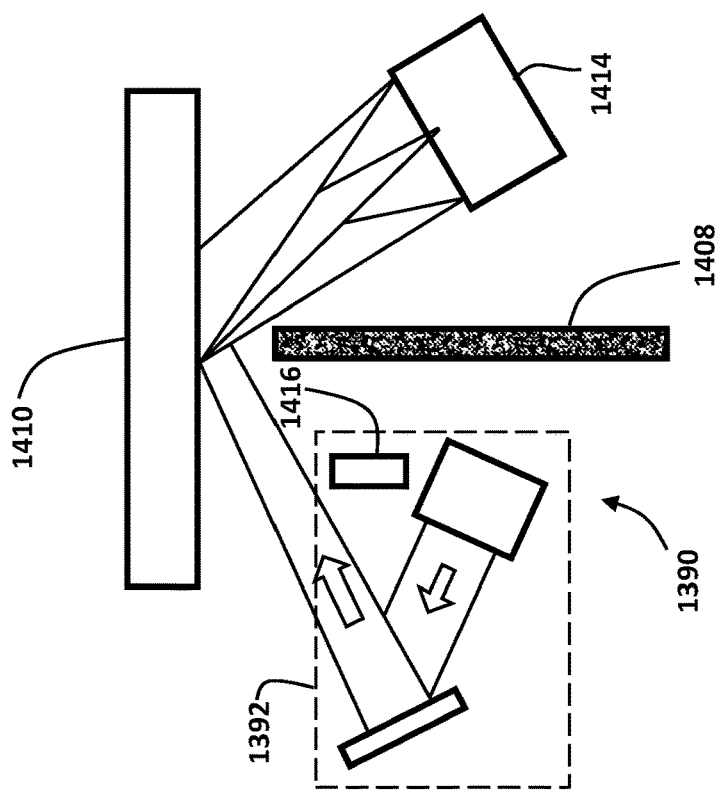
FIGS. 25A and 25B is schematic diagram of an embodiment of the invention useful for seeing or detecting an object behind an obstruction.
Figure 25A:
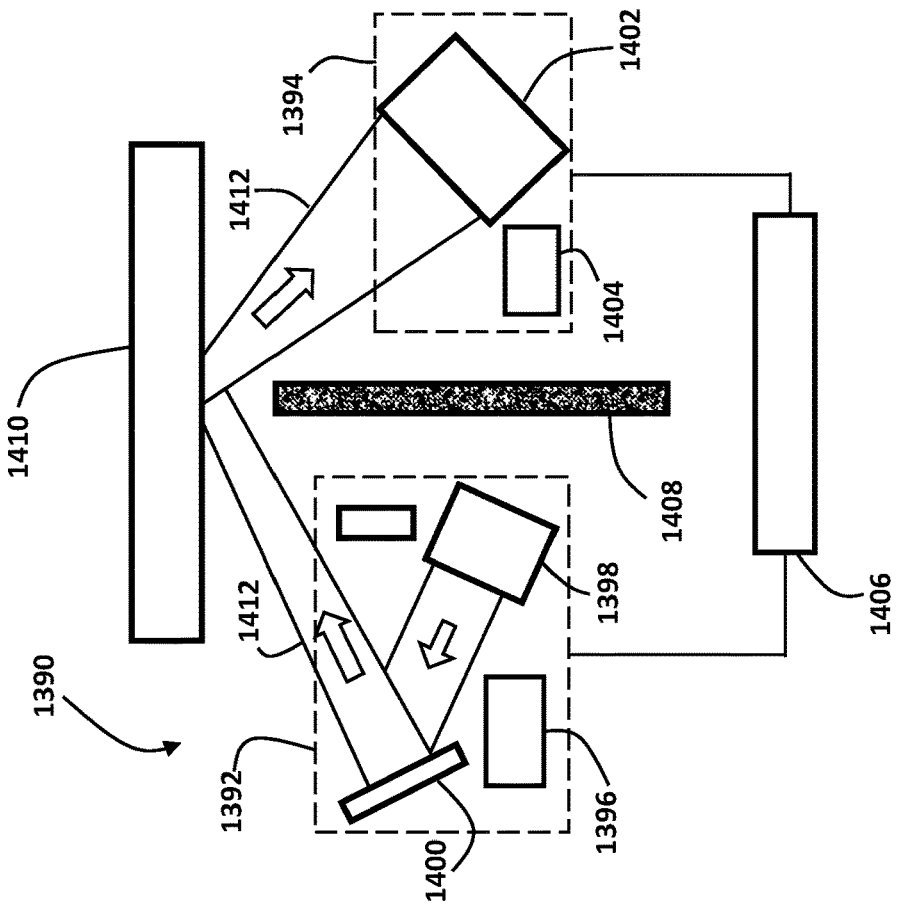

Referring to FIG. 25A an apparatus for discovering an out of sight object is generally identified by reference numeral 1390. The apparatus 1390 comprises a transmitter 1392 and a receiver 1394. The transmitter 1392 may comprise a first computer 1396, laser 1398 and a spatial modulator 1400, similar for example to the transmitter 1102 described with reference to FIG. 15A. The receiver 1394 may comprise a camera 1402 (e.g. CCD camera, CMOS or array of photodiodes) and a second computer 1402 for receiving and processing data from the camera 1402. The transmitter 1392 and receiver 1394 may have access to a data communication network 1406 so that they may exchange data with one another. The data communication network 1406 is not a part of the apparatus 1000, although the transmitter 1002 and receiver 1004 may have one or more interface (not shown) respectively for sending and receiving data over the data communication network 1406. The data communication network may take a number of forms, including by not limited to, wireless systems (e.g. WiFi, Bluetooth, cellular) and wired systems (e.g. Ethernet, power-line), or any combination of these.

It is noted that the apparatus 1390 is shown in use in FIG. 25A with a obstruction 1408 and a reflecting surface 1410, all shown in plan view. The obstruction 1408 may be any temporary or permanent object or structure that prevents or obscures a direct line of sight between the transmitter 1392 and receiver 1394. The reflecting surface may by a disordered medium that produces diffuse scattering and reflection of light, such as a surface of a building. In one embodiment the transmitter 1392 may be part of a vehicle (such as a car, van or truck), the obstruction may be the corner of building, and the reflecting surface may be another building on the opposite side of the street.

In a first step (shown in FIG. 25A), a transmission path 1412 between the transmitter 1392 and receiver 1394 may be characterised in the same way as described with reference to FIG. 15A for example, to determine a focusing spatial modulation pattern for the spatial light modulator 1400 for each pixel or group of pixels of the camera 1402. For the sake of brevity the description of these steps is not repeated here, but the steps from the description of FIG. 15A are incorporated into the present embodiment. It may be necessary to temporarily place the camera 1402 behind the blocking object 1408 for the purposes of characterisation. Once the characterisation process is complete, the receiver 1392 may transmit the plurality of spatial modulation patterns (or any computer processable equivalent of them) to the transmitter 1392 for storage (either locally or remotely. e.g. a remote server accessible via the internet) and subsequent use. The camera 1402 may be removed at this point.

Referring to FIG. 25B the transmitter (mounted on or part of the vehicle) may return to the same location at a future point in time. Once at the location, the vehicle may establish whether them is an object 1414 out of direct line of sight, obscured by the obstruction 1408. The object 1414 could be another vehicle (stationary or moving), a cyclist or pedestrian, i.e. any object that could temporarily occupy the same location or a location close to the location of the camera 1402 during the characterising process. The transmitter may use the first computer 1396 to retrieve the plurality of focusing spatial modulation patterns for the transmission path 1412. These focusing spatial modulation patterns may be used in a similar way as described with reference to FIG. 15B to generate an image, i.e. each focusing spatial modulation pattern is applied to laser light from the transmitter and spatially modulated light sent toward the object 1414 by reflection from the reflecting surface 1410 and focusing in an imaging plane previously occupied by the camera 1402 during the characterisation process. If the object 1414 is present, light is scattered and reflected by it. Some of the light will be reflected back towards the reflecting surface 1410. The reflecting surface 1410 will scatter that reflected light and a small portion may reach a photodetector 1416. All that is required is for the photodetector 1416 to detect some light reflected by the object 1414 and the reflecting surface 1410, and for the first computer 1410 to store the reflected light intensity In some embodiments, the wavelength of the laser light from the transmitter may have a wavelength greater than about 800 nm and may be within, but not limited to, the near-infrared portion of the electromagnetic spectrum (e.g. about 900 nm to about 2,000 nm). A wavelength filter may be used to reduce the light intensity within a certain range (e.g. 400-800 nm) to distinguish the ambient light from the reflected light from the object.

This process is repeated for each focusing spatially modulating pattern (each one corresponding to a pixel of the camera 1402). If an image is to be displayed to human (or otherwise required by an image analysis algorithm), the recorded intensity values from the photodetector can be used to generate an image in a way similar to that described in conjunction with FIG. 15B. Alternatively the first computer 1410 may process the recorded intensity values to determine if the object 1414 is present in the location obscured by the obstruction 1408. Once the first computer 1410 has made the determination, this may be used to cause a subsequent action or a further decision. For example, the first computer 1410 could cause a warning to be communicated to a user of the vehicle that an object is present behind the obstruction 1408. Alternatively, the first computer 1410 could cause the vehicle to wait until the object 1414 has gone, or to turn around the corner if no object is detected. This may be useful in embodiments where the vehicle is an autonomous vehicle for example: the outcome of the determination may be used by the vehicle to make further control decisions (e.g. go, wait, etc.).

Whilst the embodiments above have been described with reference to silicon-based computer processors, it is envisaged that one or more of these may be replaced with an optical computing processor. For example, it may be that the process of matrix inversion may be performed using an optical network. One such example is described in Wu, K., et al. "Computing matrix inversion with optical networks" (see Wu K, Soci C, Shum P P. Zheludev N I. Computing matrix inversion with optical networks. Optics express, 2014 Jan. 13; 22(1):295-304, which is incorporated herein by reference).

Some embodiments have been described with reference to electromagnetic radiation at visible wavelengths. The invention is not limited to one or more wavelength in this band. Other embodiments may use electromagnetic radiation in other portions of the spectrum, for example, but not limited to ultraviolet and near-infrared.

The invention claimed is:

1. A computer-implemented method of focusing electromagnetic radiation at a target, the electromagnetic radiation travelling to the target via a disordered medium, which method comprises a characterising process and a focusing process:

the characterising process comprising the steps of:
(a) controlling a transmitter to:
generate first input coherent electromagnetic radiation using a plurality of electromagnetic radiation sources;
apply a sequence of spatial modulation patterns to said first input coherent electromagnetic radiation, each spatial modulation pattern setting each one of plurality of electromagnetic radiation sources to an on state or to an off state; and
direct the first input coherent electromagnetic radiation toward the target via the disordered medium;
(b) controlling a receiver to:
receive a signal representing an intensity of output electromagnetic radiation at the target, and generate a corresponding total output signal;
store output data representing each total output signal whereby, once the sequence of spatial modulation patterns has concluded, said output data comprises a plurality of particular spatial modulation output signals, each particular spatial modulation output signal corresponding to one of the spatial modulation patterns;
wherein a complex-valued transmission matrix comprising a plurality of complex-valued transmission constants approximates a relationship between the first input coherent electromagnetic radiation and the output electromagnetic radiation, the characterising process determining a real-valued transmission matrix comprising a plurality of real-valued transmission constants which approximate a relationship between the intensities of the first input coherent electromagnetic radiation and the output electromagnetic radiation, each real-valued transmission constant associated with one of said plurality of electromagnetic radiation sources, the method further comprising the steps of:
(c) for each electromagnetic radiation source of the plurality of electromagnetic radiation sources determining the associated real-valued transmission constant as a function of said output data and the on and off states of that electromagnetic radiation source over the sequence of spatial modulation patterns;
(d) storing said plurality of real-valued transmissions constants, each real-valued transmission constant comprising a real number;
(e) determining a focusing spatial modulation pattern of said plurality of electromagnetic radiation sources by:
determining a group of real-valued transmission constants from the plurality of real-valued transmission constants by examining the real number of each real-valued transmission constant and including the real-valued transmission constant in the group so that the group comprises real-valued transmission constants which have real numbers greater than the real numbers of real-valued transmission constants not in said group; and
setting a state indicator for each electromagnetic radiation source for causing the electromagnetic radiation source to be in said on state if the associated real-valued transmission constant is in said group and in said off state if not, the state indicators for said plurality of electromagnetic sources forming said focusing spatial modulation pattern;
the focusing process comprising the steps of:
(f) generating second input coherent electromagnetic radiation and applying a spatial modulation to said second input coherent electromagnetic radiation using said focusing spatial modulation pattern; and
(g) directing said second input coherent electromagnetic radiation toward the target via the disordered medium.

2. A computer-implemented method as claimed in claim 1, wherein said group comprises: real-valued transmission constants which cause a peak-to-background ratio of said second electromagnetic radiation at said target to be greater than one and/or a predetermined percentage of the real-valued transmission constants when ranked by the real numbers.

3. A computer-implemented method as claimed in claim 2, wherein said predetermined percentage comprises the top n % of the real-valued transmission constants.

4. A computer-implemented method as claimed in claim 3, wherein n is within one of the following ranges: $15\% \le n \le 50\%$, $20\% \le n \le 45\%$, $22\% < n \le 40\%$, $25\% \le n \le 35\%$, $25\% \le n \le 33\%$, and $29\% \le n \le 31\%$ or n is within one of the following ranges: $30\% \le n \le 50\%$, $30\% \le n \le 45\%$, $30\% \le n \le 40\%$, $30\% \le n \le 35\%$, $30\% < n \le 33\%$, $30 \le n \le 31\%$ and/or wherein n is approximately 30%.

5. A computer-implemented method as claimed in claim 1, wherein in step (c) said determining of the associated real-valued transmission constant comprises performing a computer-implemented operation that represents a product of the output data of each particular spatial modulation output signal and the corresponding on or off state of the electromagnetic radiation source of the spatial modulation associated with that particular spatial modulation output signal respectively.

6. A computer-implemented method as claimed in claim 1, wherein in step (b) said receiving the signal representing an intensity of output electromagnetic radiation at the receiver comprises a direct detection of the electromagnetic radiation intensity at the receiver.

7. A computer-implemented method as claimed in claim 6, wherein said direct detection comprises the steps of:
providing a plurality of electromagnetic radiation detectors at said receiver;
performing steps (a) to (e) for each electromagnetic radiation detector, whereby a respective focusing spatial modulation pattern is generated for each electromagnetic radiation detector; and performing steps (f) and (g) for each electromagnetic radiation detector using the respective focusing spatial modulation pattern and recording an output intensity signal for each electromagnetic radiation detector.

8. A computer-implemented method as claimed in claim 1, wherein in step (b) said receiving the signal representing an intensity of output electromagnetic radiation at the receiver comprises an indirect detection of the electromagnetic radiation intensity at the receiver; wherein said indirect detection comprises the steps of:
providing a plurality of electromagnetic radiation detectors at said receiver;
performing steps (a) to (e) for each electromagnetic radiation detector, whereby a respective focusing spatial modulation pattern is generated for each electromagnetic radiation detector; and
performing steps (f) and (g) for each electromagnetic radiation detector using the respective focusing spatial modulation pattern and recording an output intensity signal for each electromagnetic radiation detector;
wherein said step of recording said output intensity signals comprises recording with a single receiver and wherein said single receiver indirectly detects said electromagnetic radiation at said target, said receiver generating said output intensity signals for each respective focusing spatial modulation pattern.

9. A computer-implemented method as claimed in claim 8, wherein said indirect detection comprises detection of ultrasound waves generated by the photoacoustic effect when said output electromagnetic radiation reaches said target.

10. A computer-implemented method as claim in claim 1, wherein in step (b) said receiving the signal representing an intensity of output electromagnetic radiation at the receiver comprises an indirect detection of the electromagnetic radiation intensity and wherein said indirect detection comprises detection of ultrasound waves generated by the photoacoustic effect when said output electromagnetic radiation reaches said target and/or detection of fluorescence generated by said output electromagnetic radiation when it reaches said target.

11. A computer-implemented method as claimed in claim 1, wherein in step (a) each electromagnetic radiation source is on within said sequence of spatial modulations the same number of times that it is off and/or the number of electromagnetic radiation sources that are on within each spatial modulation of said sequence of spatial modulation patterns is the same as the number of electromagnetic radiation sources that are off.

12. A computer-implemented method as claimed in claim 1, wherein said plurality of electromagnetic radiation sources comprises a plurality of individually controllable electromagnetic radiation sources.

13. A computer-implemented method as claimed in claim 1, wherein in step (a) said first coherent electromagnetic radiation has a first wavelength and in said step (f) said second coherent electromagnetic radiation has a second wavelength, and wherein:
(i) said first wavelength is the same as said second wavelength; or
(ii) said first wavelength is different than said second wavelength.

14. A computer-implemented method as claimed in claim 13, wherein said first input coherent electromagnetic radiation has a wavelength between about 100 nm and about 10,000 nm and/or said second input coherent electromagnetic radiation has a wavelength between about 100 nm and about 10,000 nm.

15. A computer-implemented method as claimed in claim 1, wherein in step (a) said first input coherent electromagnetic radiation is one of pulsed and intensity-modulated continuous wave to cause the photoacoustic effect at said target and/or wherein said second input coherent electromagnetic radiation is one of continuous wave, pulsed and intensity-modulated.

16. A computer-implemented method of transmitting through a disordered medium from a transmitter to a receiver an image represented as input coherent electromagnetic radiation, the disordered medium represented by a transmission matrix comprising a plurality of complex-valued transmission constants that relate said input coherent electromagnetic radiation to output electromagnetic radiation at said receiver, which method comprises the steps of:
performing a characterising process on said disordered medium to determine said transmission matrix;
using said transmitter to transmit said image through said disordered medium;
performing a reconstruction process using said transmission matrix to generate a reconstructed image from the output electromagnetic radiation at said receiver;
wherein in said characterisation process the step of determining said transmission matrix comprises:
determining said complex-valued transmission constants as real-valued transmission constants by using an approximately linear relationship between said input electromagnetic radiation and said output electromagnetic radiation; and
using said real-valued transmission constants to generate and store a version of the transmission matrix;
and said reconstruction process comprises the steps of:
generating a plurality of output images comprising intensity or amplitude values of said output electromagnetic radiation;
generating said reconstructed image by combining said plurality of output images and said version of the transmission matrix in a way that effects a matrix multiplication of an inverse of said transmission matrix and said plurality of output images; and
outputting said reconstructed image from said receiver;
wherein said step of determining said transmission matrix comprises the step of using data processing technique having a forward model that links the image to the plurality of output images with a series of linear equations, and using an algorithm to obtain the real-valued transmission constants of the transmission matrix by solving the series of linear of equations;
wherein said characterising process comprises the steps of:
at said transmitter:
providing a plurality of controllable electromagnetic radiation sources for transmitting said image and/or
at said receiver:
providing a plurality of electromagnetic radiation detectors;
receiving said plurality of output images from said disordered medium with said plurality of electromagnetic radiation detectors, each output image of said plurality of output images comprising said output electromagnetic radiation field in the form of an intensity speckle pattern corresponding to one of said plurality of known input images; and processing said known input images and said output images to determine said real-valued transmission constants;

wherein the step of determining said real-valued transmission constants comprises:

for a first pair, mn, of electromagnetic radiation detector m (m=1, 2, . . . m) and electromagnetic radiation source n (n=1, 2, . . . , N):

(a) take the first input and output image pair (p=1) and determine the product of (i) the measured output electromagnetic intensity or amplitude at electromagnetic radiation detector m, (Im p), and (ii) a binary value, (hn p), indicating whether the corresponding electromagnetic radiation source n of the pair mn was on or off for that input and output image pair p (p=1);

(b) repeat step (a) for each input and output image pair p (p=2, 3, . . . , P);

(c) sum the products obtained in steps (a) and (b); and (d) divide said sum by the number of electromagnetic radiation sources N and store the result as the mnth real-valued transmission constant in said transmission matrix; and repeat steps (a) to (d) for each other pair of electromagnetic radiation detector m and electromagnetic radiation source n to generate m×n real-valued transmission constants and store as the transmission matrix.

* * * * *